US007198900B2

(12) United States Patent
Woudenberg et al.

(10) Patent No.: US 7,198,900 B2
(45) Date of Patent: Apr. 3, 2007

(54) MULTIPLEX DETECTION COMPOSITIONS, METHODS, AND KITS

(75) Inventors: Timothy M. Woudenberg, Moss Beach, CA (US); Dar Bahatt, Foster City, CA (US); Muhammad A. Sharaf, Oakland, CA (US); Timothy Z. Liu, Fremont, CA (US); Serguei Ermakov, Hayward, CA (US); Charles R. Connell, Redwood City, CA (US); Jens J. Hyldig-Nielsen, Holliston, MA (US)

(73) Assignee: Applera Corporation, Foster City, CA (US)

( * ) Notice: Subject to any disclaimer, the term of this patent is extended or adjusted under 35 U.S.C. 154(b) by 275 days.

(21) Appl. No.: 10/652,430

(22) Filed: Aug. 29, 2003

(65) Prior Publication Data

US 2005/0074774 A1 Apr. 7, 2005

(51) Int. Cl.
C12Q 1/68 (2006.01)
C07H 21/02 (2006.01)
C07H 21/04 (2006.01)

(52) U.S. Cl. .................. 435/6; 536/23.1; 536/24.3
(58) Field of Classification Search .................. 435/6; 536/23.1, 24.3
See application file for complete search history.

(56) References Cited

U.S. PATENT DOCUMENTS

| | | | |
|---|---|---|---|
| 5,494,810 A * | 2/1996 | Barany et al. | 435/91.52 |
| 5,853,984 A | 12/1998 | Davis et al. | |
| 5,856,174 A * | 1/1999 | Lipshutz et al. | 435/286.5 |
| 5,871,917 A | 2/1999 | Duffy | |
| 5,888,731 A * | 3/1999 | Yager et al. | 435/6 |
| 6,137,584 A | 10/2000 | Seidel et al. | |
| 6,200,756 B1 | 3/2001 | Herman et al. | |
| 6,208,815 B1 | 3/2001 | Seidel et al. | |
| 6,214,556 B1 | 4/2001 | Olek et al. | |
| 6,221,592 B1 | 4/2001 | Schwartz et al. | |
| 6,287,765 B1 * | 9/2001 | Cubicciotti | 435/6 |
| 6,287,772 B1 * | 9/2001 | Stefano et al. | 435/6 |
| 6,331,393 B1 | 12/2001 | Laird | |
| 6,340,567 B1 | 1/2002 | Schwartz et al. | |
| 6,355,420 B1 | 3/2002 | Chan | |
| 6,355,421 B1 * | 3/2002 | Coull et al. | 435/6 |
| 6,403,311 B1 | 6/2002 | Chan | |
| 6,448,012 B1 | 9/2002 | Schwartz | |
| 6,509,158 B1 | 1/2003 | Schwartz | |
| 6,713,262 B2 * | 3/2004 | Gellibolian et al. | 435/6 |
| 2002/0086324 A1 | 7/2002 | Laird | |
| 2002/0115091 A1 | 8/2002 | Southern et al. | |
| 2003/0036067 A1 | 2/2003 | Schwartz | |
| 2003/0104464 A1 | 6/2003 | Berlin et al. | |
| 2003/0138831 A1 | 7/2003 | Kwagh et al. | |
| 2006/0078915 A1 * | 4/2006 | Fuchs et al. | 435/6 |

FOREIGN PATENT DOCUMENTS

| | | |
|---|---|---|
| DE | 10145831 A1 | 4/2003 |
| WO | WO 97/46705 | 12/1997 |
| WO | WO 00/70329 | 11/2000 |
| WO | WO 01/20533 A2 | 3/2001 |
| WO | WO 02/22882 A2 | 3/2002 |
| WO | WO 02/34935 A2 | 5/2002 |
| WO | WO 03/042658 A2 | 5/2003 |
| WO | WO 03/066884 A2 | 8/2003 |

OTHER PUBLICATIONS

M. Famulok et al., "Aptamers as Tools in Molecular Biology and Immunology" Current Topics in Microbiology and Immunology, Springer, Berlin DE, vol. 243, 1999, pp. 123-126.
M. Barnes et al., "Fluorescence Imaging of Single Molecules in Polymer Microspheres" Cytometry, vol. 36, 1999, pp. 169-175.
P. Goodwin et al., "Single-molecule Detection in Liquids by Laser-induced Fluorescence" Acc. Chem. Res., vol. 29, 1996, pp. 607-613.
S. Nicewarner-Pena et al., "Submicrometer Metallic Barcodes" Science, Vo. 294, Oct. 5, 2001, pp. 137-141.
S. Matsuura et al., "Real-time Observation of a Single DNA Digestion by λ Exonuclease Under a Fluorescence Microscope Field" Nucleic Acids Research, vol. 29, No. 16, 2001, pp. 1-5.
C. Kung et al., "Confinement and Manipulation of Individual Molecules in Attoliter Volumes" Analytical Chemistry, vol. 70, No. 3, Feb. 1, 1998, pp. 658-661.
J. Fister et al., "Counting Single Chromophore Molecules for Ultrasensitve Analysis and Sensitive Separations on Microchip Devices" Anal. Chem., vol. 70, 1998, pp. 431-437.
Z. Yi et al., "Stretching and Imaging Studies of Single DNA Molecules" Chinese Science Bulletin, vol. 45, No. 15, Aug. 2000, pp. 1365-1368.
L. Grondahl et al., "Encoding Combinatorial Libraries: A Novel Application of Fluorescent Silica Colloids" Langmuir 2000, vol. 16, No. 25, pp. 9709-9715.
F. Eggerding et al., "Fluorescence-Based Oligonucleotide Ligation Assay for Analysis of Cystic Fibrosis Transmembrane Conductance Regulator Gene Mutations" Human Mutation, vol. 5, No. 2, 1995, pp. 153-165.
International Search Report dated Feb. 17, 2005 issued in International Application No. PCT/US2004/028311, filed Aug. 30, 2004, 10 pgs.
I. Braslavsky et al.,"Sequence Information Can Be Obtained From Single DNA Molecules" PNAS, vol. 100, No. 7, Apr. 1, 2003, pp. 3960-3964.

(Continued)

Primary Examiner—Ethan Whisenant
(74) Attorney, Agent, or Firm—John W. Burns

(57) ABSTRACT

The present invention generally relates to the detection of analytes, particularly biomolecules in samples. The invention also relates to compositions, methods, and kits for detecting the presence of analytes, typically in multiplex detection formats. The invention also relates to methods for determining the presence of at least one analyte in a sample, the methods employing employ single molecule detection techniques to individually detect at least one molecular complex or at least part of a molecular complex.

28 Claims, 18 Drawing Sheets

OTHER PUBLICATIONS

M. Wabuyele et al., "Single Molecule Detection of Double-stranded DNA in Poly(methylmethacrylate) and Polycarbonate Microfluidic Devices" Electrophoresis 2001, vol. 22, pp. 3939-3948.

J. P. Knemeyer et al., "Probes for Detection of Specific DNA Sequences at the Single-Molecule Level" Anal. Chem., vol. 72, No. 16, Aug. 15, 2000, pp. 3717-3724.

B. Haab et al., "Single Molecule Fluorescence Burst Detection of DNA Fragments Separated by Capillary Electrophoresis" Anal. Chem., vol. 67, No. 18, Sep. 15, 1995, pp. 3253-3260.

J. Michaelis et al., "Optical Microscopy Using a Single-Molecule Light Source" Nature, vol. 405, May 18, 2000, pp. 325-328.

F. Loscher et al., "Counting of Single Protein Molecules at Interfaces and Application of this Technique in Early-Stage Diagnosis" Anal. Chem., vol. 70, No. 15, Aug. 1, 1998, pp. 3202-3205.

W. P. Ambrose et al., "Single Molecule Fluroescence Spectroscopy at Ambient Temperature" Chem. Rev., vol. 99, No. 10, (1999), pp. 2929-2956.

H. Li et al., "Ultrasensitive Coincidence Fluorescence Detection of Single DNA Molecules" Anal. Chem., vol. 75, No. 7, Apr. 1, 2003, pp. 1664-1670.

Y. Ma et al., "Single-molecule Immunoassay and DNA Diagnosis" Electrophoresis 2001, vol. 22, pp. 421-426.

S. Nie et al., "Optical Detection of Single Molecules" Ann. Rev. Biophys. Biomol. Struct. 1997, vol. 26, pp. 567-596.

D. Twerenbold et al., "Single Molecule Detector for Mass Spectrometry with Mass Independent Detection Efficiency" Proteomics 2001, vol. 1, pp. 66-69.

L. Li et al., "In Situ Single-Molecule Detection of Antibody-Antigen Binding by Tapping-Mode Atomic Force Microscopy" Anal. Chem. vol. 74, Dec. 1, 2002, pp. 6017-6022.

X. Yan et al., "Characteristics of Different Nucleic Acid Staining Dyes for DNA Fragment Sizing by Flow Cytometry" Anal. Chem., vol. 71, No. 24, Dec. 16, 1999, pp. 5470-5480.

K. Weston et al. "Measuring the Number of Independent Emitters in Single-molecule Fluorescence Images and Trajectories Using Coincident Photons" Anal. Chem., vol. 74, No. 20, Oct. 15, 2002, pp. 5342-5349.

M. Prummer et al., "Single-molecule Identification by Spectrally and Time-resolved Fluorescence Detection" Anal. Chem., vol. 72, No. 3, Feb. 1, 2000, pp. 443-447.

T. Anazawa et al., "Electrophoretic Quantitation of Nucleic Acids without Amplification by Single-molecule Imaging" Anal. Chem., vol. 74, No. 19, Oct. 1, 1992, pp. 5033-5038.

G. Segers-Nolten et al., "Scanning Confocal Fluorescence Microscopy for Single Molecule Analysis of Nucleotide Exision Repair Complexes" Nucleic Acids Research, vol. 30, No. 21, (2002), pp. 4720-4727.

M. Medina et al. "Fluorescence Correlation Spectroscopy for the Detection and Study of Single Molecules in Biology" BioEssays, vol. 24, (2002), pp. 758-764.

S. Tetin et al., "Measuring Antibody Affinity and Performing Immunoassay at the Single Molecule Level" Anal. Biochem., vol. 307, (2002), pp. 84-91.

S. Schultz et al., "Single-target Molecule Detection with Nonbleaching Multicolor Optical Immunolabels" PNAS, vol. 97, No. 3, Feb. 1, 2000, pp. 996-1001.

R. Brown et al., "Review of Techniques for Single Molecule Detection in Biological Samples" NPL Report, Sep. 2001, pp. 1-38.

R. Keller et al., "Analytical Applications of Single-Molecule Detection" Anal. Chem., vol. 74, No. 9, Jun. 1, 2002, pp. 316A-324A.

B. Kirk et al., "Single Nucleotide Polymorphism Seeking Long Term Association with Complex Disease" Nucleic Acids Research, vol. 30, No. 15, (2002), pp. 3295-3311.

O. Zelphati et al., "PNA-dependent Gene Chemistry: Stable Coupling of Peptides and Oligonucleotides to Plasmid DNA" BioTechniques, vol. 28, No. 2, Feb. 2000, pp. 304-316.

B. Geron-Landre et al., "Sequence-specific Fluorescent Labeling of Double-stranded DNA Observed at the Single Molecule Level" Nucleic Acids Research, vol. 31, No. 20, Aug. 28, 2003, pp. 1-8.

D. Cherny et al. "Analysis of Various Sequence-specific Triplexes by Electron and Atomic Force Microscopies" Biophysical Journal, vol. 74, Feb. 1998, pp. 1015-1023.

J. Kim et al., "Simultaneous Topographic and Fluorescence Imaging of Single DNA Molecules for DNA Analysis with a Scanning Near-field Optical/Atomic Force Microscope" Anal. Chem., vol. 73, No. 24, Dec. 15, 2001, pp. 5984-5991.

M. Han et al., "Quantum-dot-tagged Microbeads for Multiplexed Optical Coding of Biomolecules" Nature Biotech., vol. 19, Jul. 2001, pp. 631-635.

P. Blier et al., "Binding of Ku Protein to DNA" J. Biol. Chem. vol. 268, No. 10, Apr. 5, 1993, pp. 7594-7601.

V. Namasivayam et al., "Electrostretching DNA Molecules Using Polymer-enhanced Media Within Microfabricated Devices" Anal. Chem., vol. 74, No. 14, Jul. 15, 2002, pp. 3378-3385.

V. Demidov et al., "Duplex DNA Capture" Curr. Issues Mol. Biol., vol. 2, No. 1, (2000), pp. 31-35.

J. Taylor et al., "Probing Specific Sequences on Single DNA Molecules with Bioconjugated Fluorescent Nanoparticles" Anal. Chem., vol. 72, No. 9, May 1, 2000, pp. 1979-1986.

X. Xu et al., "Direct Measurement of Single-molecule Diffusion and Photodecomposition in Free Solution" Science, vol. 275, No. 21, Feb. 1997, pp. 1106-1109.

Z. Foldes-Papp et al., "Ultrasensitive Detection and Identification of Fluorescent Molecules by FCS: Impact for Immunobiology" PNAS, vol. 98, No. 20, Sep. 25, 2001, pp. 11509-11514.

M. Cotlet et al., "Identification of Different Emitting Species in the Red Fluorescent Protein DsRed by Means of Ensemble and Single-Molecule Spectroscopy" PNAS, vol. 98, No. 25, Dec. 4, 2001, pp. 14398-14403.

S. Weiss, "Fluorescence Spectroscopy of Single Biomolecules" Science, vol. 283, Mar. 12, 1999, pp. 1676-1683.

D. Smith et al., "Single-polymer Dynamics in Steady Shear Flow" Science, vol. 283, Mar. 12, 1999, pp. 1724-1727.

U. Landegren et al. "A Ligase-mediated Gene Detection Technique" Science, vol. 241, Aug. 26, 1988, pp. 1077-1080.

K. Heinze et al., "Simultaneous Two-photon Excitation of Distinct Labels for Dual-color Fluorescence Crosscorrelation Analysis" PNAS, vol. 97, No. 19, Sep. 12, 2000, pp. 10377-10382.

N. Dovichi et al., "Laser-induced Fluorescence of Flowing Samples as an Approach to Single-molecule Detection of Liquids" Anal. Chem., vol. 56, No. 3, Mar. 1984, pp. 348-354.

U. Alon et al., "Broad Patterns of Gene Expression Revealed by Clustering Analysis of Tumor and Normal Colon Tissues Probed by Oligonucleotide Arrays" PNAS, vol. 96, Jun. 1999, pp. 6745-6750.

I. Walton et al., "Particles for Mulitplexed Analysis in Solution: Detection and Identification of Striped Metallic Particles Using Optical Microscopy" Anal. Chem., vol. 74, No. 10, May 15, 2002, pp. 2240-2247.

Y. Zhang et al, "Stretching and Imaging Studies of Single DNA Molecules" Chinese Science Bulletin, vol. 45, No. 15, Aug. 2000, pp. 1365-1368.

H. Yan et al., "Directed Nucleation Assembly of DNA Tile Complexes for Barcode-patterned Lattices" PNAS Early Ed., vol. 10, May 15, 2003, pp. 1-6.

M. Merchant et al., "Recent Advancements in Surface-enhanced Laser Desorption/Ionization-time of Flight-mass Spectrometry" Electrophoresis, vol. 21, (2000), pp. 1164-1167.

H. Chou et al., "A Microfabricated Device for Sizing and Sorting DNA Molecules" PNAS, vol. 96, Jan. 1999, pp. 11-13.

S. Nie et al., "Probing Single Molecules and Single Nanoparticles by Surface-enhanced Raman Scattering" Science, vol. 275, Feb. 21, 1997, pp. 1102-1106.

J. Lohse et al., "Double Duplex Invasion by Peptide Nucleic Acid: A General Principle for Sequence-specific Targeting of Double-stranded DNA" PNAS, vol. 96, No. 21, Oct. 12, 1999, pp. 11804-11808.

K. Swinney et al., "Detection in Capillary Electrophoresis" Electrophoresis, vol. 21, (2000), pp. 1239-1250.

H. Cai et al., "Flow Cytometry-based Minisequencing: A New Platform for High-throughput Single-nucleotide Polymorphism Scoring" Genomics, vol. 66, (2000), pp. 135-143.

M. Foquet et al., "DNA Fragment Sizing by Single Molecule Detection in Submicrometer-sized Closed Fluidic Channels" Anal. Chem., vol. 74, No. 6, Mar. 15, 2002, pp. 1415-1422.

H. Li et al., "Selective Detection of Individual DNA Molecules by Capillary Polymerase Chain Reaction" Anal. Chem., vol. 73, No. 7, Apr. 1, 2001, pp. 1537-1543.

Y. Wang et al., "Optical Mapping of Site-directed Cleavages on Single DNA Molecules by the RecA-assisted Restriction Endonuclease Technique" PNAS, vol. 92, Jan. 1995, pp. 165-169.

T. Ha, "Single-molecule Fluorescence Methods for the Study of Nucleic Acids" Current Opinion in Structural Biology, vol. 11, (2001), pp. 287-292.

J. Enderlein, "A Theoretical Investigation of Single-molecule Fluorescence Detection on Thin Metallic Layers" Biophysical Journal, vol. 78, No. 4, Apr. 2000, pp. 2151-2158.

C. Viteri et al., "Probing the Dynamic Guest-Host Interactions in Sol-Gel Films Using Single Molecule Spectroscopy" J. Am. Chem. Soc., vol. 125, No. 7, (2003), pp. 1980-1987.

W. Trabesinger et al., "Detection of Individual Oligonucleotide Pairing by Single-molecule Microscopy" Anal. Chem., vol. 71, No. 1, Jan. 1, 1999, pp. 279-283.

J. Gimzewski et al., "Nanoscale of Single Molecules Using Local Probes" Science, vol. 283, Mar. 12, 1999, pp. 1683-1688.

B. Geron-Landre et al., "Sequence-specific Fluroescent Labeling of Double-stranded DNA Observed at the Single Molecule Level" Nucleic Acids Research, vol. 31, No. 20, Aug. 28, 2003, pp. 1-8.

"Luminex—The Luminex LabMap System" Technical Bulletin, www.luminexcorp.com, pp. 1-3.

Y. Kanyama et al., "Detection of *p16* Promoter Hypermethylation in Serum of Gastric Cancer Patients" Cancer Sci, vol. 94, May 2003, pp. 418-420.

P. Adorjan et al., "Tumour Class Prediction and Discovery by Microarray-based DNA Methylation Analysis" Nucleic Acids Research, vol. 30, No. 5, Jan. 2002, pp. 1-9.

C. Eads et al., "MethyLight: A High-throughput Assay to Measure DNA Methylation" Nucleic Acids Research, vol. 28, No. 8, Mar. 2000, pp. 1-8.

R. Singal et al., "DNA Methylation" Blood, vol. 93, No. 12, Jun. 15, 1999, pp. 4059-4070.

B. Ramsahoye et al., "Non-CpG Methylation is Prevalent in Embryonic Stem Cells and May be Mediated by DNA Methyltransferase 3a" PNAS, vol. 97, No. 10, May 9, 2000, pp. 5237-5242.

R. Sadri et al., "Rapid Analysis of DNA Methylation Using New Restriction Enzyme Sites Created by Bisulfite Modification" Nucleic Acids Research, vol. 24, No. 24, Nov. 1996, pp. 5058-5059.

H. Thomassin et al., "Identification of 5-Methylcytosine in Complex Genomes" Methods, vol. 19 (1999), pp. 465-475.

G. Pfeifer et al., "Genomic Sequencing and Methylation Analysis by Ligation Mediated PCR" Science, New Series, vol. 246, No. 4931, Nov. 10, 1989, pp. 810-813.

\* cited by examiner

SEQUENCE LISTING

```
<160> NUMBER OF SEQ ID NOS: 33

<210> SEQ ID NO 1
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gttgtttatt atttcttctt tgcttaa                                         27

<210> SEQ ID NO 2
<211> LENGTH: 27
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 2
ttaagcaaag aagaaataat aaacaac                                          27

<210> SEQ ID NO 3
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gaaaagaaag                                                             10

<210> SEQ ID NO 4
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
ctttcttttc                                                             10

<210> SEQ ID NO 5

<400> SEQUENCE: 5

000

<210> SEQ ID NO 6
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
agaggaggag                                                             10

<210> SEQ ID NO 7
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
ctcctcctct                                                             10

<210> SEQ ID NO 8

<400> SEQUENCE: 8

000

<210> SEQ ID NO 9
<211> LENGTH: 10
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 9
aaaggaaagg                                                              10

<210> SEQ ID NO 10
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
cctttccttt                                                              10

<210> SEQ ID NO 11

<400> SEQUENCE: 11

000

<210> SEQ ID NO 12
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gggaagagag                                                              10

<210> SEQ ID NO 13
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
ctctcttccc                                                              10

<210> SEQ ID NO 14

<400> SEQUENCE: 14

000

<210> SEQ ID NO 15
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
agaaagggga                                                              10

<210> SEQ ID NO 16
<211> LENGTH: 10
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 16
tcccctttct                                                          10

<210> SEQ ID NO 17

<400> SEQUENCE: 17

000

<210> SEQ ID NO 18
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
aggaagaaaa                                                          10

<210> SEQ ID NO 19
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
ttttcttcct                                                          10

<210> SEQ ID NO 20

<400> SEQUENCE: 20

000

<210> SEQ ID NO 21
<211> LENGTH: 10
<212> TYPE: DNA
<213> ORGANISM: Artificial Sequence
<220> FEATURE:
<223> OTHER INFORMATION: Description of Artificial Sequence: Linker
      oligonucleotide

<400> SEQUENCE: 21
ccggcctgca                                                          10

<210> SEQ ID NO 22
<211> LENGTH: 14
<212> TYPE: DNA
<213> ORGANISM: Artificial Sequence
<220> FEATURE:
<223> OTHER INFORMATION: Description of Artificial Sequence: Primer

<400> SEQUENCE: 22
atagacacag gaaa                                                     14

<210> SEQ ID NO 23
<211> LENGTH: 20
<212> TYPE: DNA
<213> ORGANISM: Artificial Sequence
```

```
<220> FEATURE:
<223> OTHER INFORMATION: Description of Artificial Sequence: Primer

<400> SEQUENCE: 23
ggggaaaccc gtactatacg                                              20

<210> SEQ ID NO 24
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
gcatctccta caagtg                                                  16

<210> SEQ ID NO 25
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
gcatctccta caagta                                                  16

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence: Probe

<400> SEQUENCE: 26
ggtctgcgat ggatggcc                                                18

<210> SEQ ID NO 27
<211> LENGTH: 10
<212> TYPE: PRT
<213> ORGANISM: Artificial Sequence
<220> FEATURE:
<223> OTHER INFORMATION: Description of Artificial Sequence: Epitope tag

<400> SEQUENCE: 27

Glu Gln Lys Leu Ile Ser Glu Glu Asp Leu
 1               5                  10

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence: Epitope tag

<400> SEQUENCE: 28

Tyr Pro Tyr Asp Val Pro Asp Tyr Ala
 1               5

<210> SEQ ID NO 29
<211> LENGTH: 11
<212> TYPE: PRT
<213> ORGANISM: Artificial Sequence
<220> FEATURE:
<223> OTHER INFORMATION: Description of Artificial Sequence: Epitope tag
```

```
<400> SEQUENCE: 29

Tyr Thr Asp Ile Glu Met Asn Arg Leu Gly Lys
  1               5                  10

<210> SEQ ID NO 30
<211> LENGTH: 11
<212> TYPE: PRT
<213> ORGANISM: Artificial Sequence
<220> FEATURE:
<223> OTHER INFORMATION: Description of Artificial Sequence: Epitope tag

<400> SEQUENCE: 30

Gln Pro Glu Leu Ala Pro Glu Asp Pro Glu Asp
  1               5                  10

<210> SEQ ID NO 31
<211> LENGTH: 14
<212> TYPE: PRT
<213> ORGANISM: Artificial Sequence
<220> FEATURE:
<223> OTHER INFORMATION: Description of Artificial Sequence: Epitope tag

<400> SEQUENCE: 31

Gly Lys Pro Ile Pro Asn Pro Leu Leu Gly Leu Asp Ser Thr
  1               5                  10

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Epitope tag

<400> SEQUENCE: 32

Asp Tyr Lys Asp Asp Asp Asp Lys Gly
  1               5

<210> SEQ ID NO 33
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)..(13)
<223> OTHER INFORMATION: a, t, c, g, unknown or other

<400> SEQUENCE: 33
cctggtccnn nnn                                                    13
```

MULTIPLEX DETECTION COMPOSITIONS, METHODS, AND KITS

RELATED APPLICATIONS

This application is related to co-filed patent applications "Compositions, Methods, and Kits for Assembling Probes Comprising Coded Molecular Tags" (U.S. "Express Mail" mail labeling number: EL 897 623 158 US) and "Compositions, Methods, and Kits for Fabricating Coded Molecular Tags" (U.S. "Express Mail" mail labeling number: EL 897 623 161 US).

INTRODUCTION

Disclosed herein are compositions, methods, and kits for detecting the presence of analytes in a sample, typically in multiplex detection formats using single molecule detection techniques (SMDs). Various qualitative and/or quantitative assay methods are currently used for analyte analyses such as genotyping, gene expression profiling, forensic identification, antibody and antigen detection, protein profiling, and other protein and nucleic acid measurements. Such methods typically rely on probes, such as oligonucleotides, antibody molecules or immunoreactive fragments of antibody molecules, peptides, ligands or receptors, and the like. These probes are generally labeled with a single species of label, such as a fluorophore, radioisotope, or enzyme. The label is usually detected in an ensemble measurement, for example, a multitude of labeled molecules are collectively identified and/or quantified.

Multiplex assays typically involve simultaneous or near-simultaneous identification and/or quantitation of multiple targets in a single sample or a single pooled sample. While generally decreasing the time needed to evaluate multiple targets, such multiplex assays can be limited by the number, availability, and cost of differently labeled probes used in the assay. Conventional multiplex assays include, for example, fixed array formats such as nucleic acid microarrays and protein microarrays, and various bead-based formats. Bead-based multiplex assays reportedly provide the benefit of increased hybridization kinetics compared to fixed arrays, but the use of beads significantly increases the cost of these assays.

SUMMARY

Compositions, methods, and kits for determining the presence of at least one analyte in a sample, including multiplex analyses of multiple analyte species in one or more samples, are disclosed herein. In certain embodiments, analytes include, for example but are not limited to, proteins; peptides; nucleic acids, including DNA and/or RNA molecules; small molecules; drugs and drug metabolites.

According to certain methods, molecular complexes, diagnostic for the presence or absence of an analyte in a sample, are formed. Molecular complexes typically comprise at least one coded molecular tag that includes multiple reporter group species in an ordered pattern. Typically, the multiplicity of reporter group species in a molecular complex or at least part of a molecular complex are detected as a coupled assembly, either simultaneously or near-simultaneously, similar in some respects to reading a product identification bar code, but at a molecular level. At least one molecular complex is individually detected using at least one SMD to identify the order of the reporter group species in at least one coded molecular tag. In certain embodiments, only part of the molecular complex is individually detected.

In certain embodiments, methods for determining the presence of at least one analyte in a sample comprise: combining the sample with at least one probe set for the at least one analyte, the probe set comprising (a) at least one first probe comprising at least one first reaction portion and (b) at least one second probe comprising at least one second reaction portion. At least one probe in at least one probe set further comprises at least one identity portion comprising at least one coded molecular tag. In certain embodiments, at least one first probe and at least one corresponding second probe are suitable for forming a molecular complex in the presence of at least one corresponding analyte or at least one corresponding analyte surrogate. When a molecular complex, or at least a part of a molecular complex, is individually detected, the presence of the corresponding analyte can be determined by identifying the order of reporter group species in the molecular complex or at least part of a molecular complex. Conversely, the lack of a particular molecular complex indicates that the corresponding analyte is not present in the sample.

In certain embodiments, at least one analyte is amplified forming at least one amplification product, typically an analyte surrogate. In certain embodiments, at least one molecular complex comprises at least one analyte surrogate or at least a part of at least one analyte surrogate and at least one probe comprising at least one identity portion. In certain embodiments, at least one molecular complex comprises the complement of at least one analyte surrogate or the complement of at least a part of an analyte surrogate and at least one probe comprising at least one identity portion.

In certain embodiments, at least one analyte, at least part of at least one analyte, or their complements, are amplified before, during, or after molecular complex formation. In certain embodiments, the methods and kits further comprise at least one polymerase, at least one ligation agent, or at least one polymerase and at least one ligation agent. In certain embodiments, methods comprise ligation reactions; primer extension or "gap filling" reactions; transcription, including but not limited to reverse transcription; translation; or combinations thereof, including but not limited to, coupled in vitro transcription/translation systems.

In certain embodiments, individually detecting comprises SMD, including, but not limited to, scanning probe microscopy techniques and applied optical spectroscopy techniques. In certain embodiments, at least one molecular complex or at least a part of a molecular complex become tethered or attached, directly or indirectly, to a substrate by one or more attachment points. In certain embodiments, at least one molecular complex or at least part of a molecular complex is individually detected while interacting with, or being tethered or attached directly or indirectly to, a substrate. In certain embodiments, at least one molecular complex or at least one part of a molecular complex is individually detected in solution.

Compositions, methods, and kits for assembling probes are also provided. In certain embodiments, probes comprise at least one reaction portion and at least one identity portion including at least one coded molecular tag. In certain embodiments, probes further comprise at least one capture ligand, at least one cleavable component, at least one crosslinker, at least one adapter, or combinations thereof. In certain embodiments, probes are assembled using coded molecular tags and oligonucleotides comprising sequences complementary to target sequences in at least one analyte, at least one analyte surrogate, or both. In certain embodiments, probe assembly comprises at least template, at least one ligation template, or both. In certain embodiments, probes are assembled using coded molecular tags and antibodies that immuno-specifically react with at least one analyte, at least one analyte surrogate, or both. In certain embodiments, probes are assembled using coded molecular tags and binding proteins or binding peptides that bind to at least one analyte, at least one analyte surrogate, or both. In certain embodiments, probes are assembled using coded molecular tags and aptamers that bind to at least one analyte, at least one analyte surrogate, or both.

In certain embodiments, probes sets comprise at least one first probe comprising at least one first reaction portion and at least one second probe comprising at least one second reaction portion. At least one probe in the probe set further comprises at least one identity portion comprising at least one coded molecular tag. In certain embodiments, probe sets further comprise at least one capture ligand, at least one hybridization tag, at least one aptamer, at least one mobility modifier, at least one analytical portion, or combinations thereof. In certain embodiments, at least one analytical portion comprises at least one reporter group. In certain embodiments, the reaction portion of at least one first probe comprises at least one reporter group, the reaction portion of at least one second probe comprise at least one reporter group, or both. In certain embodiments, the reaction portion of at least one first probe comprises at least one fluorescent reporter group, the reaction portion of at least one corresponding second probe comprises at least one fluorescent reporter group, or both, wherein the fluorescent reporter groups are the same or different.

Compositions, methods, and kits for fabricating coded molecular tags are also provided. In certain embodiments, at least one coded molecular tag is fabricated from subunits, including without limitation, synthetic oligonucleotides, nucleotide fragments, semi-synthetic sequences, or combinations thereof. In certain embodiments, at least one subunit is enzymatically-labeled with at least one reporter group, chemically-labeled with at least one reporter group, synthesized (e.g., solid-phase synthesis or template-directed synthesis) with at least one incorporated reporter group, or combinations thereof. In certain embodiments, compositions, methods, and kits for fabricating at least one coded molecular tag comprise at least one template, at least one ligation template, or both. In certain embodiments, compositions, methods, and kits for fabricating coded molecular tags comprise at least one PNA, at least one pcPNA, or both.

In certain embodiments, coded molecular tags further comprise at least one adapter, at least one crosslinker, or both. In certain embodiments, the coded molecular tag adapter or crosslinker, or both, are cleavable. In certain embodiments, at least one coded molecular tag further comprises at least one capture ligand, at least one hybridization tag, at least one aptamer sequence, or combinations thereof. In certain embodiments, at least one coded molecular tag is used to prepare at least one probe.

Kits for determining the presence of at least one analyte in a sample; kits for assembling at least one probe; and kits for fabricating at least one coded molecular tag; are also provided. Kits serve to expedite the performance of the methods of interest by assembling two or more components required for carrying out the methods. Kits generally contain components in pre-measured unit amounts to minimize the need for measurements by end-users. Kits preferably include instructions for performing one or more methods of the invention. Typically, the kit components are optimized to operate in conjunction with one another. In certain embodiments, kits comprise at least one probe, at least one probe set, or both. In certain embodiments, kits comprise at least one ligation agent; at least one polymerase; at least one nucleotide; at least one amino acid; at least one charged tRNA; at least one substrate; at least one of reporter group; or combinations thereof.

Certain embodiments of the disclosed methods and kits comprise at least one ligation agent. In certain embodiments, the ligation agent comprises at least one ligase, such as DNA ligase or RNA ligase, including, without limitation, the bacteriophage T4 (T4) DNA ligase, T4 RNA ligase, E. coli DNA ligase, or E. coli RNA ligase. In certain embodiments at least one ligase comprises at least one thermostable ligase. Exemplary thermostable ligases include without limitation, Taq ligase, Pfu ligase, Tfl ligase, Tli ligase, Tth ligase, and the like.

In certain embodiments, ligation is performed non-enzymatically. While not limiting, non-enzymatic ligation includes chemical ligation, such as, autoligation and ligation in the presence of an "activating" and/or a reducing agent. Non-enzymatic ligation can utilize specific reactive groups on the respective 3' and 5' ends of the probes to be ligated. Thus, in certain embodiments of the methods and kits of the invention, the ligation agent is an "activating" or reducing agent. In certain embodiments, one or more probes suitable for ligation are provided that comprise appropriate reactive groups for non-enzymatic ligation.

In certain embodiments the disclosed methods and kits further comprise at least one polymerase, including, but not limited to at least one DNA polymerase, at least one RNA polymerase, at least one reverse transcriptase, or combinations thereof. Exemplary polymerases include DNA polymerase I, T4 DNA polymerase, SP6 RNA polymerase, T3 RNA polymerase, T7 RNA polymerase, AMV reverse transcriptase, M-MLV reverse transcriptase, and the like. In certain embodiments, at least one DNA polymerase lacks 5'->3' exonuclease activity, for example, but not limited to Klenow fragment of DNA polymerase, 9°N$_m$™ DNA polymerase, Vent$_R$® (exo⁻) DNA polymerase, Deep Vent$_R$® (exo⁻) DNA polymerase, Therminator™ DNA polymerase, and the like. In certain embodiments, at least one polymerase is thermostable. Exemplary thermostable polymerases include Taq polymerase, Tfl polymerase, Tth polymerase, Tli polymerase, Pfu polymerase, AmpliTaq Gold® polymerase, 9°N$_m$™ DNA polymerase, Vent$_R$® DNA polymerase, Deep Vent$_R$® DNA polymerase, UlTma polymerase, and the like.

The skilled artisan will understand that any of a number of polymerases and ligases could be used in the methods and kits of the invention, including without limitation, those isolated from thermostable or hyperthermostable prokaryotic, eukaryotic, or archael organisms. The skilled artisan will also understand the terms "ligase" and "polymerase" include not only naturally occurring enzymes, but also recombinant enzymes; and enzymatically active fragments, cleavage products, mutants, or variants of such enzymes. Descriptions of ligases and polymerases can be found in, among other places, Twyman, Advanced Molecular Biology, BIOS Scientific Publishers (1999); Enzyme Resource Guide, rev. 092298, Promega (1998); Sambrook and Russell, Molecular Cloning, A Laboratory Manual, Cold Spring Harbor Press, 3d ed. (2001)("Sambrook and Russell"); Sambrook, Fritsch, and Maniatis, Molecular Cloning, A Laboratory Manual, Cold Spring Harbor Press, 2d ed. (1989) ("Sambrook et al."); Ausbel et al., Current Protocols in Molecular Biology, John Wiley & Sons, Inc. (1995, including supplements through the August 2003)("Ausbel et al.").

In certain embodiments, kits comprise at least one coded molecular tag; at least one crosslinker, including without limitation at least one chemical crosslinker, at least one photo-activated crosslinker, at least one cleavable crosslinker; at least one antibody, including without limitation at least one reporter group-labeled antibody; at least one binding protein, at least one binding peptide, or both; at least one capture ligand; at least one capture moiety; at least one hybridization tag; at least one mobility modifier; at least one aptamer; at least one template, at least one ligation template, or both; or combinations thereof.

BRIEF DESCRIPTION OF THE DRAWINGS

FIG. 1: depicts a schematic overview of exemplary embodiments.

FIG. 7: depicts exemplary coded molecular tag fabrication methods.

FIG. 12: depicts exemplary coded molecular tag fabrication methods.

DESCRIPTION OF VARIOUS EMBODIMENTS

Figure 1A:
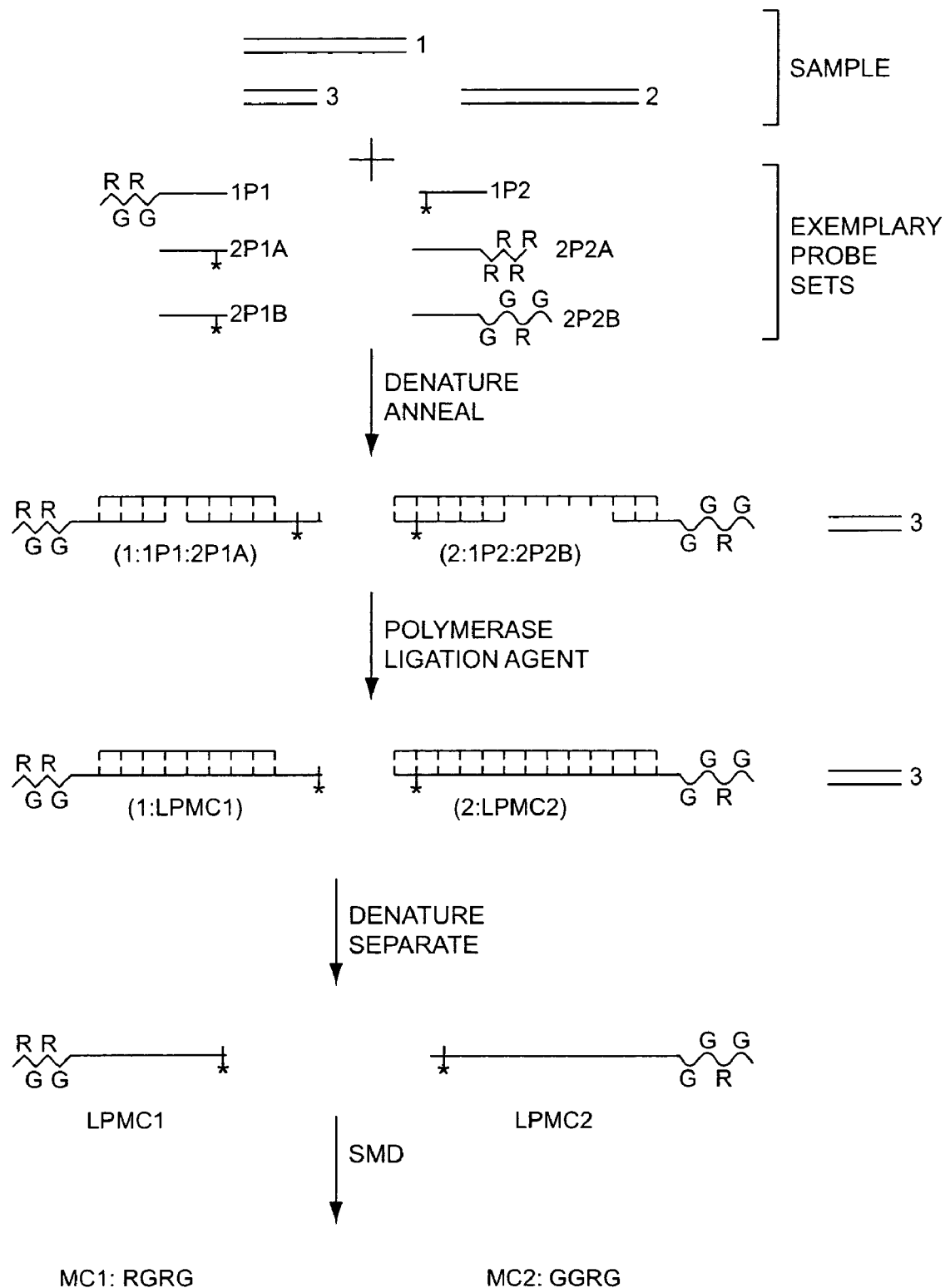
FIG. 1A depicts exemplary probes and methods for determining the presence of nucleic acid analytes.

The section headings used herein are for organizational purposes only and are not to be construed as limiting the subject matter described in any way. All literature and similar materials cited in this application, including but not limited to, patents, patent applications, articles, books, treatises, and internet web pages, regardless of the format of such literature and similar materials, are expressly incorporated by reference in their entirety for any purpose.

Definitions

The term "affinity tag" as used herein refers to at least one component of a multi-component complex, wherein the components of the multi-component complex specifically interact with or bind to each other, for example but not limited to a capture moiety and its corresponding capture ligand. Exemplary multiple-component complexes include without limitation, ligands and their receptors, including but not limited to, avidin-biotin, streptavidin-biotin, and derivatives of biotin, streptavidin and/or avidin, including but not limited to desthiobiotin, NeutrAvidin, CaptAvidin, and the like; binding proteins/peptides, including but not limited to maltose-maltose binding protein (MBP), calcium-calcium binding protein/peptide (CBP); antigen-antibody, including but not limited to epitope tags, including but not limited to c-MYC (e.g., EQKLISEEDL)(SEQ ID NO: 27), HA (e.g., YPYDVPDYA) (SEQ ID NO: 28), VSV-G (e.g., YTDIEMNRLGK) (SEQ ID NO: 29), HSV (e.g., QPELAPEDPED) (SEQ ID NO: 30), V5 (e.g., GKPIPNPLLGLDST) (SEQ ID NO: 31, and FLAG Tag™ (e.g., DYKDDDDKG) (SEQ ID NO: 32), and their corresponding anti-epitope antibodies; haptens, for example but not limited to dinitrophenyl and digoxigenin, and their corresponding antibodies; aptamers and their corresponding targets; hybridization tags and their complements; poly-His tags (e.g., penta-His and hexa-His) and its binding partners, including without limitation, corresponding immobilized metal ion affinity chromatography (IMAC) materials and anti-poly-His antibodies; fluorophores and anti-fluorophore antibodies; and the like. The skilled artisan will understand that at least one affinity tag can be found in one or more molecular complexes, such as in least one identity portion, at least one analytical portion, at least one reaction portion, or combinations thereof.

The term "coded molecular tag" as used herein refers to a molecule, for example but not limited to, a nucleic acid sequence or an amino acid sequence, comprising a multiplicity of reporter group species that are connected, directly or indirectly to the molecule in an ordered pattern, so that the order of reporter group species can be identified when the coded molecular tag is individually detected. In certain embodiments, at least one coded molecular tag comprises at least two locations, referred to as labeling positions, where reporter groups are or can be incorporated, bound or attached by, but without limitation, synthesis techniques, enzymatic incorporation, chemical incorporation, reporter group-labeled antibody binding, or binding of PNAs and/or pcPNAs comprising at least one reporter group. Typically, the occupation of at least some labeling positions by reporter group species results in an ordered pattern. This ordered pattern can be changed by adding reporter group species to additional labeling positions or by removing or quenching reporter groups.

Typically, a coded molecular tag comprises at least one reporter group at a particular labeling position and can comprise a multiplicity of reporter groups at a particular labeling position. In certain embodiments, at least one coded molecular tag comprises at least one labeling position comprising a multiplicity of reporter groups, wherein all of the reporter groups within at least one labeling position are the same. In certain embodiments, at least one coded molecular tag comprises at least one labeling position comprising a multiplicity of reporter groups, wherein the reporter groups within at least one labeling position are from at least two different reporter group species. In certain embodiments, each coded molecular tag labeling position comprises at least one reporter group species. In certain embodiments, at least one coded molecular tag comprises at least one labeling position that do not comprise at least one reporter group species, i.e., at least one of the labeling positions is vacant, but can still serve as part of the ordered reporter group species (see, e.g., FIG. 3F, wherein the illustrative coded molecular tag comprises the ordered pattern Y-R-Ø (i.e., vacant)-B, left to right). In certain embodiments, at least one vacant labeling position is not included in the reporter group order.

In certain embodiments, at least one coded molecular tag comprises at least one template, for example but not limited to, at least one peptide; at least one protein; or at least one nucleic acid sequence, such as at least part of a linear or linearizable viral genome, such as the genomes of adenovirus, hepatitis virus, herpes virus, rotavirus, and the like, or bacteriophages such as lambda, M13, ɸX-174, T-series bacteriophages, and the like, including derivatives thereof comprising cloning cassettes, polylinkers, and the like; plasmids, such as pBR322 and pUC series plasmids, etc., including derivatives thereof comprising cloning cassettes, polylinkers, and the like; synthetic templates; templates comprising artificial sequences; and the like. Suitable nucleic acid templates can be double-stranded, single-stranded, or both. The skilled artisan will understand that virtually any piece of nucleic acid can serve as a template for fabricating a nucleic acid coded molecular tag provided that it is large enough to include at least two distinguishable labeling positions, or it can be combined with at least one other nucleic acid sequence so that the combined sequence is large enough to include at least two labeling positions. In certain embodiments, the restriction map and/or nucleotide sequence is known. Restriction maps and nucleotide sequences for exemplary nucleic acid templates can be found in, among other places, the New England BioLabs 2002–03 Catalog & Technical Reference, New England BioLabs, Inc., Beverly, Mass.; Stratagene 2003/2004 Catalog, La Jolla, Calif.; and at a variety of internet addresses, including the Entrez web site maintained by the National Center for Biotechnology Information, particularly the "Nucleotide" web page located at world wide web address: ncbi.nlm.nih.gov/entrez/query.fcgi?db=Nucleotide; and the Biology WorkBench maintained by the San Diego Supercomputer Center at world wide web address: workbench.sdsc.edu. Expressly excluded from the term coded molecular tag is a sequence comprising a multiplicity of reporter groups that are not in an ordered pattern for individual detection, such as might be used in conventional ensemble detection techniques, for example but not limited to, a sequence labeled with a single fluorescent reporter group species using, for example but not limited to, nick translation or primer extension; or a synthetic oligonucleotide comprising incorporated reporter groups from a single reporter group species.

The skilled artisan understands that the number of labeling positions in a template can vary, depending at least in part on the reporter group species employed, the detection method, and sometimes the reporter group binding method. Generally, coded molecular tags include reporter group species that are incorporated, intercalated, bound, or combinations thereof. Typically, coded molecular tags are fabricated by combining subunits; hybridizing subunits on templates; synthesizing at least one subunit on at least one template using, for example but not limited to, primer extension or PCR; binding reporter groups to templates using, for example but not limited to, at least one reporter group-labeled PNA, at least one reporter group-labeled pcPNA, at least one reporter group-labeled antibody; at least one reporter group-labeled minor groove binder; at least one reporter group-labeled aptamer; or combinations thereof. In certain embodiments, at least one subunit is ligated to at least one other subunit, at least one primer, or both.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, or CAB. Continuing with this example, expressly included are combinations that contain repeats of one or more item or term, such as BB, AAA, MB, BBC, AAABCCCC, CBBAAA, CABABB, and so forth. The skilled artisan will understand that there typically is no limit on the number of items or terms in any combination, unless otherwise apparent from the context.

The term "corresponding" as used herein refers to at least one specific relationship between the elements to which the term refers. For example, at least one first probe of a particular probe set corresponds to at least one second probe of the same probe set, and vice versa. The probes of a particular probe set are designed to hybridize with or bind to at least part of a corresponding analyte, a corresponding analyte surrogate, or both; an antibody immunospecifically binds to its corresponding antigen, or more particularly, to a corresponding epitope of the corresponding antigen, and conversely, a particular epitope is bound by its corresponding antibody; a particular capture moiety binds to its corresponding capture ligand, and vice versa; a particular analyte can be identified when its corresponding molecular complex or at least part of the corresponding molecular complex is individually detected and the order of the corresponding reporter group species are identified; and so forth.

The term "diagnostic indicator" as used herein refers to at least one biomolecule that is used as a predictor of, or is associated with, a disease state, a metabolic disorder, or the like. Exemplary diagnostic indicators include insulin; prostate specific antigen (PSA); alpha-fetal protein (AFP); wild-type and mutant forms of cellular oncogenes and their protein products; wild-type and mutant forms of tumor suppressor genes and their protein products such as p53 and pRB; rheumatoid factor; anti-nuclear antibodies; auto-antibodies; anti-foreign antigen antibodies; and the like. The skilled artisan will appreciate that for certain diagnostic indicators, the quantitative or relative amount of, rather than the mere presence of, a particular indicator may have clinical or biological significance. For example but without limitation, insulin levels above or below appropriate thresholds can serve as a diagnostic indicator for hyperinsulinism (hypersecretion of insulin) or diabetes mellitus (hyposecretion of insulin); relative PSA levels or ratios can serve as a diagnostic indicator for prostate cancer; relative levels or ratios of vascular endothelial growth factor (VEGF) isoforms serve as diagnostic indicators for rheumatoid arthritis, certain malignancies, and tumor progression; and the like. Expressly included within the term diagnostic indicator are hyper- and hypo-methylated forms of disease-related genes.

The terms "fluorophore" and "fluorescent reporter group" are intended to include any compound, label, or moiety that absorbs energy, typically from an illumination source, to reach an electronically excited state, and then emits energy, typically at a characteristic wavelength, to achieve a lower energy state. For example but without limitation, when certain fluorophores are illuminated by an energy source with an appropriate excitation wavelength, typically an incandescent or laser light source, photons in the fluorophore are emitted at a characteristic fluorescent emission wavelength. Fluorophores, sometimes referred to as fluorescent dyes, may typically be divided into families, such as fluorescein and its derivatives; rhodamine and its derivatives; cyanine and its derivatives; coumarin and its derivatives; Cascade Blue™ and its derivatives; Lucifer Yellow and its derivatives; BODIPY and its derivatives; and the like. Exemplary fluorophores include indocarbocyanine (C3), indodicarbocyanine (C5), Cy3, Cy3.5, Cy5, Cy5.5, Cy7, Texas Red, Pacific Blue, Oregon Green 488, Alexa Fluor 488, Alexa Fluor 532, Alexa Fluor 546, Alexa Fluor 568, Alexa Fluor 594, Alexa Fluor 647, Alexa Fluor 660, Alexa Fluor 680, JOE, Lissamine, Rhodamine Green, BODIPY, fluorescein isothiocyanate (FITC), carboxy-fluorescein (FAM), phycoerythrin, rhodamine, dichlororhodamine (dRhodamine™), carboxy tetramethylrhodamine (TAMRA™), carboxy-X-rhodamine (ROX™), LIZ™, VIC™, NED™, PET™, SYBR, PicoGreen, RiboGreen, and the like. Descriptions of fluorophores and their use, can be found in, among other places, R. Haugland, Handbook of Fluorescent Probes and Research Products, 9$^{th}$ ed. (2002), Molecular Probes, Eugene, Oreg.; M. Schena, Microarray Analysis (2003), John Wiley & Sons, Hoboken, N.J.; Synthetic Medicinal Chemistry 2003/2004 Catalog, Berry and Associates, Ann Arbor, Mich.; G. Hermanson, Bioconjugate Techniques, Academic Press (1996); and Glen Research 2002 Catalog, Sterling, Va. Near-infrared dyes are expressly within the intended meaning of the terms fluorophore and fluorescent reporter group.

The term "foreign antigen" as used herein refers to one or more components of, metabolic products of, or one or more element derived from a foreign organism. Exemplary foreign organisms include bacteria, fungi, protozoa, viruses, insects, parasites, and other infectious and/or pathogenic agents. A foreign antigen typically comprises at least one protein, including but not limited to glycoproteins, phosphoproteins, lipoproteins, flagellin, peptidoglycan, endotoxin, and exotoxin; at least one peptide; at least one lipopolysaccharide; at least one prion; at least one nucleic acid; and the like.

The term "hybridization tag" as used herein refers to an oligonucleotide sequence that can be used for separating the element to which it is bound, including without limitation, bulk separation; or tethering or attaching a multiplicity of hybrid pairs comprising different element species and the same hybridization tag species to a substrate, or both. In certain embodiments, the same hybridization tag is used with a multiplicity of different elements to effect: bulk separation, substrate tethering, substrate attachment, or combinations thereof. A hybridization tag complement typically refers to at least one oligonucleotide that comprises at least one sequence of nucleotides that are complementary to and hybridize with the hybridization tag. In various embodiments, hybridization tag complements serve as capture moieties for tethering or attaching at least one hybridization tag:element complex to at least one substrate; serve as "pull-out" sequences for bulk separation procedures; or both as capture moieties and as pull-out sequences.

Typically, hybridization tags and their corresponding hybridization tag complements are selected to minimize: internal, self-hybridization; cross-hybridization with different hybridization tag species, nucleotide sequences in a sample, including but not limited to analytes, hybridization tag complements, or analyte surrogates; but should be amenable to facile hybridization between the hybridization tag and its corresponding hybridization tag complement. Hybridization tag sequences and hybridization tag complement sequences can be selected by any suitable method, for example but not limited to, computer algorithms such as described in PCT Publication Nos. WO 96/12014 and WO 96/41011 and in European Publication No. EP 799,897; and the algorithm and parameters of SantaLucia (Proc. Natl. Acad. Sci. 95:1460–65 (1998)). Descriptions of hybridization tags can be found in, among other places, U.S. Pat. No. 6,309,829 (referred to as "tag segment" therein); U.S. Pat. No. 6,451,525 (referred to as "tag segment" therein); U.S. Pat. No. 6,309,829 (referred to as "tag segment" therein); U.S. Pat. No. 5,981,176 (referred to as "grid oligonucleotides" therein); U.S. Pat. No. 5,935,793 (referred to as "identifier tags" therein); and PCT Publication No. WO 01/92579 (referred to as "addressable support-specific sequences" therein).

Hybridization tags can be attached to at least one end of at least one probe; or they can be located internally, for example but not limited to, adjacent to at least one restriction enzyme cleavage site, adjacent to at least one cleavable crosslinker, or both, such that cleavage at the restriction enzyme site or the cleavable crosslinker will result in the hybridization tag being at or near the newly-created end. In certain embodiments, at least one hybridization tag comprises or overlaps at least one restriction enzyme cleavage site. In certain embodiments, hybridization tags are at least 12 bases in length, at least 15 bases in length, 12–60 bases in length, or 15–30 bases in length. In certain embodiments, at least one hybridization tag is 12, 15, 20, 21, 22, 23, 24, 25, 26, 27, 28, 29, 30, 45, or 60 bases in length. In certain embodiments, at least two hybridization tag:hybridization tag complement duplexes have melting temperatures that fall within a Δ Tm range (Tmax–Tmin) of no more than 10° C. of each other. In certain embodiments, at least two hybridization tag:hybridization tag complement duplexes have melting temperatures that fall within a Δ Tm range of 5° C. or less of each other.

In certain embodiments, at least one hybridization tag is used to separate the element to which it is bound from at least one unbound component in a sample, unbound components and/or reagents in the reaction mixture, or the like. In certain embodiments, hybridization tags are used to attach at least one molecular complex or at least part of at least one molecular complex to at least one substrate. In certain embodiments, a multiplicity of molecular complexes, a multiplicity of cleavable components, a multiplicity of identity portions, a multiplicity of coded molecular tags, or combinations thereof, comprise the same hybridization tag.

For example but not limited to, separating a multiplicity of different element:hybridization tag species using the same hybridization tag complement, tethering a multiplicity of different element:hybridization tag species to a substrate comprising the same hybridization tag complement, or both.

The term "individually detecting" as used herein refers to the process of evaluating and/or interrogating the reporter group species of separate, discrete molecular complexes or at least parts of molecular complexes, in contrast to ensemble detection of reporter group species in populations of molecular complexes, as routinely done, for example, in microarray or immunoassay techniques. Typically, the order of reporter group species in at least one individually detected molecular complex or at least part of a molecular complex is determined, relative to a reference or orientation point, for example but not limited to, a tethering site, attachment sites, or both; or a set of coded molecular tags in which one or more particular labeling sites are always occupied by the same reporter group species, i.e., a distinguishable sub-pattern. Expressly excluded from the term individually detecting are techniques that comprise cleaving or releasing multiple subunits from a polymer and detecting the reporter groups of such cleaved subunits in a piecemeal fashion to determine their position or sequence in the intact polymer, such as nucleic acid sequencing or restriction enzyme mapping techniques.

The term "mobility modifier" as used herein refers to at least one molecular entity, for example but not limited to, at least one polymer chain, that when added to at least one element (e.g., at least one probe, at least one identity portion, at least one coded molecular tag, at least one molecular complex, at least one cleavable component, or combinations thereof) affects the mobility of the element to which it is hybridized or bound, covalently or non-covalently, in at least one mobility-dependent analytical technique. In certain embodiments, a multiplicity of probe sets exclusive of mobility modifiers, a multiplicity of molecular complexes exclusive of mobility modifiers, a multiplicity of identity portions exclusive of mobility modifiers, a multiplicity of cleavable components exclusive of mobility modifiers, a multiplicity of coded molecular tags exclusive of mobility modifiers, or combinations thereof, have the same or substantially the same mobility in at least one mobility-dependent analytical technique. Typically, a mobility modifier changes the charge/translational frictional drag when hybridized or bound to the element; or imparts a distinctive mobility, for example but not limited to, a distinctive elution characteristic in a chromatographic separation medium or a distinctive electrophoretic mobility in a sieving matrix or non-sieving matrix, when hybridized or bound to the corresponding element; or both (see, e.g., U.S. Pat. Nos. 5,470,705 and 5,514,543).

A mobility-dependent analytical technique is a technique based on differential rates of migration between different species being separated. Exemplary mobility-dependent analysis techniques include electrophoresis, chromatography, mass spectroscopy, sedimentation, e.g., gradient centrifugation, field-flow fractionation, multi-stage extraction techniques and the like. Descriptions of mobility-dependent analytical techniques can be found in, among other places, U.S. Pat. Nos. 5,470,705, 5,514,543, 5,580,732, 5,624,800, and 5,807,682 and PCT Publication No. WO 01/92579.

In certain embodiments, a multiplicity of molecular complexes comprising mobility modifiers, a multiplicity of cleavable components comprising mobility modifiers, a multiplicity of identity portions comprising mobility modifiers, a multiplicity of coded molecular tags comprising mobility modifiers, or combinations thereof, have substantially similar distinctive mobilities, for example but not limited to, when a multiplicity of elements comprising mobility modifiers have substantially similar distinctive mobilities so they can be bulk separated or they can be separated from other elements comprising mobility modifiers with different distinctive mobilities. In certain embodiments, a multiplicity of molecular complexes comprising mobility modifiers, a multiplicity of cleavable components comprising mobility modifiers, a multiplicity of identity portions comprising mobility modifiers, a multiplicity of coded molecular tags comprising mobility modifiers, or combinations thereof, have different distinctive mobilities.

In certain embodiments, at least one mobility modifier comprises at least one nucleotide polymer chain, including without limitation, at least one oligonucleotide polymer chain, at least one polynucleotide polymer chain, or both at least one oligonucleotide polymer chain and at least one polynucleotide polymer chain. In certain embodiments, at least one mobility modifier comprises at least one non-nucleotide polymer chain. Exemplary non-nucleotide polymer chains include, without limitation, peptides, polypeptides, polyethylene oxide (PEO), or the like. In certain embodiments, at least one polymer chain comprises at least one substantially uncharged, water-soluble chain, such as a chain composed of PEO units; a polypeptide chain; or combinations thereof.

The polymer chain can comprise a homopolymer, a random copolymer, a block copolymer, or combinations thereof. Furthermore, the polymer chain can have a linear architecture, a comb architecture, a branched architecture, a dendritic architecture (e.g., polymers containing polyamidoamine branched polymers, Polysciences, Inc. Warrington, Pa.), or combinations thereof. In certain embodiments, at least one polymer chain is hydrophilic, or at least sufficiently hydrophilic when hybridized or bound to an element to ensure that the element-mobility modifier is readily soluble in aqueous medium. Where the mobility-dependent analysis technique is electrophoresis, in certain embodiments, the polymer chains are uncharged or have a charge/subunit density that is substantially less than that of its corresponding element.

The synthesis of polymer chains useful as mobility modifiers will depend, at least in part, on the nature of the polymer. Methods for preparing suitable polymers generally follow well-known polymer subunit synthesis methods. These methods, which involve coupling of defined-size, multi-subunit polymer units to one another, either directly or through charged or uncharged linking groups, are generally applicable to a wide variety of polymers, such as polyethylene oxide, polyglycolic acid, polylactic acid, polyurethane polymers, polypeptides, oligosaccharides, and nucleotide polymers. Such methods of polymer unit coupling are also suitable for synthesizing selected-length copolymers, e.g., copolymers of polyethylene oxide units alternating with polypropylene units. Polypeptides of selected lengths and amino acid composition, either homopolymer or mixed polymer, can be synthesized by standard solid-phase methods (e.g., Int. J. Peptide Protein Res., 35: 161–214 (1990)).

One method for preparing PEO polymer chains having a selected number of hexaethylene oxide (HEO) units, an HEO unit is protected at one end with dimethoxytrityl (DMT), and activated at its other end with methane sulfonate. The activated HEO is then reacted with a second DMT-protected HEO group to form a DMT-protected HEO dimer. This unit-addition is then carried out successively until a desired PEO chain length is achieved (e.g., U.S. Pat. No. 4,914,210; see also, U.S. Pat. No. 5,777,096).

The term "molecular complex" as used herein refers to a reaction product, comprising at least one identity portion comprising at least one coded molecular tag, formed due to the presence of a particular analyte in the sample. By individually detecting a particular molecular complex or at least a part of that molecular complex, one can determine that the corresponding analyte is present in the sample. The molecular complex may, but need not, comprise all or part of the corresponding analyte or analyte surrogate, as shown for example, in FIG. 1A. In certain embodiments, at least one molecular complex comprises at least one analyte or at least one analyte surrogate and at least one probe comprising at least one identity portion. In certain embodiments, one or more molecular complexes comprise a single "linked" molecule, for example but not limited to, a ligation product molecular complex, shown as MC1 and MC2 in FIG. 1A. The skilled artisan will understand that ligation product molecular complexes are a subset of the term molecular complex, as are analytes and/or analyte surrogates hybridized with at least one ligation product molecular complex. In certain embodiments, at least one molecular complex comprises an assembly comprising at least two interacting or bound molecules, for example but not limited to an antigen-antibody complex, an aptamer-target complex, an antibody-antigen-aptamer complex, or the like, for example, as shown in FIG. 1A (e.g., 2:1P2:2P2B), FIG. 1B (MC1 and MC2), and FIG. 6B (MC1 and MC2).

In certain embodiments, at least one molecular complex comprises at least one analyte surrogate and at least one probe comprising at least one identity portion. An analyte surrogate typically comprises an amplification product, such as a cDNA, an amplicon, a primer extension product, a transcription product, a translation product, an LCR product, or the like, that results from amplifying at least part of at least one analyte or at least part of at least one analyte surrogate, but typically does not comprise the original analyte. Expressly excluded from the term molecular complex are entities or assemblies comprising one or more bead or particle, such as latex beads, agarose beads, magnetic and paramagnetic particles, dye-impregnated polymer beads, metallic particles, and the like.

In certain embodiments, at least one analyte comprises at least one amino acid, at least one nucleotide, at least one oligosaccharide, at least one phosphodiester linkage, at least one peptide bond, at least one glycosidic bond, or combinations thereof. In certain embodiments, at least one analyte comprises at least one biomolecule; at least one drug; at least one small molecule for example but not limited to a small organic molecule or metabolite; or combinations thereof. In certain embodiments, at least one analyte comprises at least one polynucleotide, such as at least one nucleic acid sequence, including but not limited to at least one genomic DNA (gDNA); hnRNA; mRNA; noncoding RNA (ncRNA), including but not limited to rRNA, tRNA, mRNA (micro RNA), siRNA (small interfering RNA), snoRNA (small nucleolar RNA), snRNA (small nuclear RNA) and stRNA (small temporal RNA); fragmented nucleic acid; nucleic acid obtained from subcellular organelles such as mitochondria or chloroplasts; and nucleic acid obtained from microorganisms, parasites, or DNA or RNA viruses that may be present in a sample. Furthermore, a nucleic acid analyte can be present in double-stranded form, single-stranded form, or both double-stranded and single-stranded form. Discussions of nucleic acid analytes can be found in, among other places, Current Protocols in Nucleic Acid Chemistry, S. Beaucage, D. Bergstrom, G. Glick, and R. Jones, eds., John Wiley & Sons (1999) including updates through August 2003.; S. Verma and F. Eckstein, Ann. Rev. Biochem., 67:99–134 (1998); S. Buckingham, Horizon Symposia, Understanding the RNAissance, Nature Publishing Group, May 2003 at pages 1–3; S. Eddy, Nature Rev. Genetics 2:919–29 (2001); and Nucleic Acids in Chemistry and Biology, 2d ed., G. Blackburn and M. Gait, eds., Oxford University Press (1996). In certain embodiments, the compositions, methods, and kits disclosed herein, can be used to analyze heritable and/or somatic mutations, including but not limited to non-sense mutations, missense mutations, insertions, deletions, and chromosomal translocations at the DNA, RNA, or protein levels.

In certain embodiments, at least one analyte comprises at least one peptide bond such as found in peptides, oligopeptides, and proteins. In certain embodiments, at least one analyte comprises at least one foreign antigen. In certain embodiments, at least one analyte comprises at least one diagnostic indicator. In certain embodiments, at least one analyte comprises at least one antibody molecule or at least one fragment or component of an antibody molecule. In certain embodiments, at least one analyte comprises at least one glycosidic bond, such as found in disaccharides, oligosaccharides, and polysaccharides, including but not limited to sugar residues present in glycoproteins.

The person of ordinary skill will appreciate that while the target sequence of a nucleic acid analyte or analyte surrogate can be described as a single-stranded molecule, the opposing strand of a double-stranded analyte comprises a complementary sequence that can also be used as a target for probe hybridization. In certain embodiments, a target sequence comprises an upstream or 5' region, a downstream or 3' region, and a "pivotal nucleotide" located at the junction of the upstream region and the downstream region (e.g., shown as "X" in FIG. 2; see also, PCT Publication No. WO 01/92579). In certain embodiments, the presence or absence of the pivotal nucleotide is being detected by the probe set and may represent, for example, without limitation, a single polymorphic nucleotide in a multi-allelic target locus, a heritable or somatic mutation, or the like.

Figure 3:
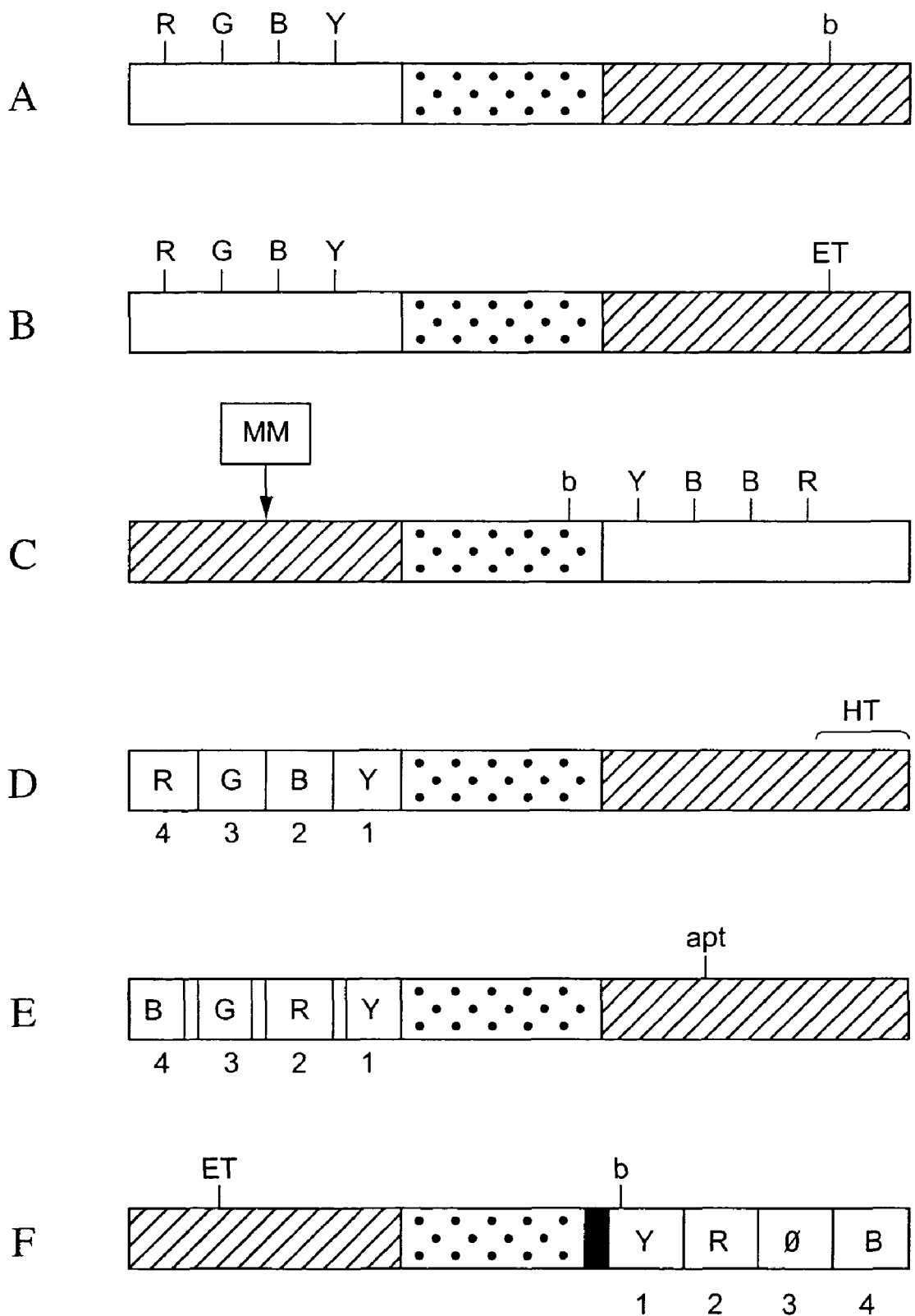
FIG. 3: depicts schematic representations of exemplary molecular complexes.

FIG. 3 schematically depicts exemplary molecular complexes. In each panel, the identity portion is illustrated as an open (unfilled) rectangle, the reaction portions are illustrated as a dotted rectangle, the analytical portion is illustrated as a diagonally striped rectangle; and the reporter groups are designated R, G, B, and Y, for example but not limited to, four different fluorescent reporter group species. In panel A, the exemplary molecular complex includes an identity portion comprising individual reporter groups R, G, B, and Y, in that order (throughout this disclosure, the order of reporter group species is shown L to R for illustration purposes, unless otherwise apparent from the context); and an analytical portion comprising at least one biotin moiety (b). The exemplary molecular complex depicted in panel B includes an identity portion comprising individual reporter groups R, G, B, and Y, in that order; and an analytical portion comprising at least one epitope tag (ET). Panel C depicts another exemplary molecular complex comprising an analytical portion comprising at least one mobility modifier (MM); a reaction portion comprising at least one biotin moiety (b); and an identity portion comprising reporter groups Y, B, and R, in the order YBBR. The exemplary molecular complex shown in panel D includes an identity portion comprising reporter group species R, G, B, and Y, in that order (i.e., in labeling positions 4, 3, 2, and 1, respectively), wherein each occupied coded molecular tag labeling position comprises at least one reporter group and in some cases a multiplicity of reporter groups, typically the same reporter group species but possibly more than one reporter group species, for example to provide color complementation at that labeling site; and an analytical portion comprising at least one hybridization tag ("HT"). In panel E, another exemplary molecular complex is shown, comprising an analytical portion comprising at least one aptamer sequence ("apt"); and an identity portion comprising a coded molecular tag including four spaced reporter group species, B, G, R, and Y in labeling positions 4, 3, 2, and 1, respectively. The exemplary molecular complex shown in panel F includes an analytical portion comprising at least one epitope tag (ET); a cleavable linker (dark region); and an identity portion comprising at least one biotin moiety and three reporter group species, Y, R, and B, in labeling positions 1, 2, and 4, respectively. No reporter groups are present at labeling position 3 (shown as Ø). Thus, when individually detected, the order of reporter groups in the cleavable identity portion is Y, R, blank (empty), and B, relative to the illustrated biotin moiety.

The term "polymerase" is used in a broad sense herein and includes DNA polymerases, enzymes that typically synthesize DNA by incorporating deoxyribonucleotide triphosphates or analogs in the 5'=>3' direction in a template-dependent and primer-dependent manner; RNA polymerases, enzymes that synthesize RNA by incorporating ribonucleotide triphosphates or analogs and may or may not be in a template-dependent manner; and reverse transcriptases, also known as RNA-dependent DNA polymerases, that synthesize DNA by incorporating deoxyribonucleotide triphosphates or analogs in the 5'=>3' direction in primer-dependent manner, typically using an RNA template. Descriptions of polymerases can be found in, among other places, R. M. Twyman, Advanced Molecular Biology, Bios Scientific Publishers Ltd. (1999); Polymerase Enzyme Resource Guide, Promega, Madison, Wis. (1998); P. C. Turner et al., Instant Notes in Molecular Biology, Bios Scientific Publishers Ltd. (1997); and B. D. Hames et al., Instant Notes in Biochemistry, Bios Scientific Publishers Ltd. (1997).

The term "polynucleotide" means polymers comprising at least two nucleotide monomers, including analogs of such polymers, including double and single stranded deoxyribonucleotides, ribonucleotides, α-anomeric forms thereof, and the like. Monomers are linked by "internucleotide linkages," e.g., phosphodiester linkages, where as used herein, the term "phosphodiester linkage" refers to phosphodiester bonds or bonds including phosphate analogs thereof, including associated counterions, e.g., $H^+$, $NH_4^+$, $Na^+$, if such counterions are present. Whenever a DNA polynucleotide is represented by a sequence of letters, such as "ATGCCTG," it will be understood that the nucleotides are in 5' to 3' order from left to right, unless it is otherwise apparent from the context, and that "A" denotes deoxyadenosine, "C" denotes deoxycytidine, "G" denotes deoxyguanosine, and "T" denotes deoxythymidine, unless otherwise noted.

"Analogs", in reference to nucleosides and/or polynucleotides, comprise synthetic analogs having modified nucleobase portions, modified pentose portions and/or modified phosphate portions, and, in the case of polynucleotides, modified internucleotide linkages, as described generally elsewhere (e.g., Scheit, Nucleotide Analogs (John Wiley, New York, (1980); Englisch, Angew. Chem. Int. Ed. Engl. 30:613–29 (1991); Agarwal, Protocols for Polynucleotides and Analogs, Humana Press (1994); and S. Verma and F. Eckstein, Ann. Rev. Biochem. 67:99–134 (1999)). Generally, modified phosphate portions comprise analogs of phosphate wherein the phosphorous atom is in the +5 oxidation state and one or more of the oxygen atoms is replaced with a non-oxygen moiety, e.g., sulfur. Exemplary phosphate analogs include but are not limited to phosphorothioate, phosphorodithioate, methylphosphonates, phosphoroselenoate, phosphorodiselenoate, phosphoroanilothioate, phosphoranilidate, phosphoramidate, boronophosphates, including associated counterions, e.g., $H^+$, $NH_4^+$, $Na^+$, if such counterions are present. Exemplary modified nucleobase portions include but are not limited to 2,6-diaminopurine, hypoxanthine, pseudouridine, C-5-propyne, isocytosine, isoguanine, 2-thiopyrimidine, and other like analogs. Particularly preferred nucleobase analogs are iso-C and iso-G nucleobase analogs available from Sulfonics, Inc., Alachua, Fla. (e.g., Benner, et al., U.S. Pat. No. 5,432,272) or LNA analogs (e.g., Koshkin et al., Tetrahedron 54:3607–30 (1998)). Exemplary modified pentose portions include but are not limited to 2'- or 3'-modifications where the 2'- or 3'-position is hydrogen, hydroxy, alkoxy, e.g., methoxy, ethoxy, allyloxy, isopropoxy, butoxy, isobutoxy and phenoxy, azido, amino or alkylamino, fluoro, chloro, bromo and the like. Modified internucleotide linkages include phosphate analogs, analogs having achiral and uncharged intersubunit linkages (e.g., E. Sterchak et al., Organic Chem., 52:4202 (1987)), and uncharged morpholino-based polymers having achiral intersubunit linkages (e.g., U.S. Pat. No. 5,034,506). Preferred internucleotide linkage analogs include PNA, pcPNA, morpholidate, acetal, and polyamide-linked heterocycles. A particularly preferred class of polynucleotide analogs where a conventional sugar and internucleotide linkage has been replaced with a 2-aminoethylglycine amide backbone polymer is PNA and pcPNA (e.g., Nielsen et al., Science, 254:1497–1500 (1991); Egholm et al., J. Am. Chem. Soc., 114: 1895–1897 (1992)). Detailed descriptions of oligonucleotide synthesis and analogs, including relevant protocols can be found in, among other places, S. Verma and F. Eckstein, Ann. Rev. Biochem. 67:99–134 (1999); J. Goodchild, Bioconj. Chem. 1:165–87 (1990); S. L. Beaucage et al., Current Protocols in Nucleic Acid Chemistry, John Wiley & Sons, New York, N.Y. (2000); U.S. Pat. Nos. 4,373,071; 4,401,796; 4,415,732; 4,458,066; 4,500,707; 4,668,777; 4,973,679; 5,047,524; 5,132,418; 5,153,319; and 5,262,530.

The term "reporter group" is used in a broad sense herein and refers to any identifiable tag, label, or moiety. The skilled artisan will appreciate that many different species of reporter groups can be used in the present teachings, either individually or in combination with one or more different reporter group. Exemplary reporter groups include, but are not limited to, fluorophores, radioisotopes, chromogens, enzymes, antigens including but not limited to epitope tags, heavy metals, dyes, phosphorescence groups, chemiluminescent groups, electrochemical detection moieties, affinity tags, binding proteins, phosphors, rare earth chelates, near-infrared dyes, including but not limited to, "Cy.7.SPh.NCS," "Cy.7.OphEt.NCS," "Cy7.OphEt.CO$_2$Su", and IRD800 (see, e.g., J. Flanagan et al., Bioconjug. Chem. 8:751–56 (1997); and DNA Synthesis with IRD800 Phosphoramidite, LI-COR Bulletin #111, LI-COR, Inc., Lincoln, Nebr.), electrochemiluminescence labels, including but not limited to, tris(bipyridal) ruthenium (II), also known as Ru(bpy)$_3^{2+}$, Os(1,10-phenanthroline)$_2$bis(diphenylphosphino)ethane$^{2+}$, also known as Os(phen)$_2$(dppene)$^{2+}$, luminol/hydrogen peroxide, Al(hydroxyquinoline-5-sulfonic acid), 9,10-diphenylanthracene-2-sulfonate, and tris(4-vinyl-4'-methyl-2,2'-bipyridal) ruthenium (II), also known as Ru(v-bpy$_3^{2+}$), and the like.

The term reporter group also includes at least one element of multi-element indirect reporter systems, e.g., affinity tags such as biotin/avidin, antibody/antigen, ligand/receptor including but not limited to binding proteins and their ligands, enzyme/substrate, and the like, in which one element interacts with other elements of the system in order to effect the potential for a detectable signal. Exemplary multi-element reporter system include a probe comprising at least one biotin reporter group with an streptavidin-conjugated fluorophore, or vice versa; a probe comprising at least one dinitrophenyl (DNP) reporter group and a fluorophore-labeled anti-DNP antibody; and the like. Detailed protocols for methods of attaching reporter groups to oligonucleotides, polynucleotides, peptides, proteins, mono-, di- and oligosaccharides, organic molecules, and the like can be found in, among other places, G. T. Hermanson, Bioconjugate Techniques, Academic Press, San Diego, Calif. (1996)("Bioconjugate Techniques"); S. L. Beaucage et al., Current Protocols in Nucleic Acid Chemistry, John Wiley & Sons, New York, N.Y. (2000); Handbook of Fluorescent Probes and Research Products, $9^{th}$ ed., Molecular Probes, Inc., Eugene, Oreg. (2002); and Pierce Applications Handbook and Catalog 2003–2004, Pierce Biotechnology, Rockford, Ill. (2003).

In certain embodiments, at least one reporter group comprises an electrochemiluminescent moiety that can, under appropriate conditions, emit detectable electrogenerated chemiluminescence (ECL). In ECL, excitation of the electrochemiluminescent moiety is electrochemically driven and the chemiluminescent emission can be optically detected. Exemplary electrochemiluminescent reporter group species include: $Ru(bpy)_3^{2+}$ and $Ru(v-bpy)_3^{2+}$ with emission wavelengths of 620 nm; $Os(phen)_2(dppene)^{2+}$ with an emission wavelength of 584 nm; luminol/hydrogen peroxide with an emission wavelength of 425 nm; Al(hydroxyquinoline-5-sulfonic acid) with an emission wavelength of 499 nm; and 9,10-diphenylanothracene-2-sulfonate with an emission wavelength of 428 nm; and the like. Modified forms of these three electrochemiluminescent reporter group species that are amenable to incorporation into probes and coded molecular tags are commercially available or can be synthesized without undue experimentation using techniques known in the art. For example, there is a $Ru(bpy)_3^{2+}$ N-hydroxy succinimide ester for coupling to nucleic acid sequences through an amino linker group has been described (see, U.S. Pat. No. 6,048,687); and succinimide esters of $Os(phen)_2(dppene)^{2+}$ and $Al(HQS)_3^{3+}$ can be synthesized and attached to nucleic acid sequences using similar methods. The $Ru(bpy)_3^{2+}$ electrochemiluminescent reporter group can be synthetically incorporated into nucleic acid sequences using commercially available ru-phosphoramidite (IGEN International, Inc., Gaithersburg, Md.).

Additionally other polyaromatic compounds and chelates of ruthenium, osmium, platinum, palladium, and other transition metals have shown electrochemiluminescent properties. Detailed descriptions of ECL and electrochemiluminescent moieties can be found in, among other places, A. Bard and L. Faulkner, Electrochemical Methods, John Wiley & Sons (2001); M. Collinson and M. Wightman, Anal. Chem. 65:2576 et seq. (1993); D. Brunce and M. Richter, Anal. Chem. 74:3157 et seq. (2002); A. Knight, Trends in Anal. Chem. 18:47 et seq. (1999); B. Muegge et al., Anal. Chem. 75:1102 et seq. (2003); H. Abrunda et al., J. Amer. Chem. Soc. 104:2641 et seq. (1982); K. Maness et al., J. Amer. Chem. Soc. 118:10609 et seq. (1996); M. Collinson and R. Wightman, Science 268:1883 et seq. (1995); and U.S. Pat. No. 6,479,233.

The term "sample" is used in a broad sense herein and is intended to include a wide range of biological materials as well as compositions derived or extracted from such biological materials. Exemplary samples include whole blood; red blood cells; white blood cells; buffy coat; hair; nails and cuticle material; swabs, including but not limited to buccal swabs, throat swabs, vaginal swabs, urethral swabs, cervical swabs, throat swabs, rectal swabs, lesion swabs, abcess swabs, nasopharyngeal swabs, and the like; urine; sputum; saliva; semen; lymphatic fluid; amniotic fluid; cerebrospinal fluid; peritoneal effusions; pleural effusions; fluid from cysts; synovial fluid; vitreous humor; aqueous humor; bursa fluid; eye washes; eye aspirates; plasma; serum; pulmonary lavage; lung aspirates; and tissues, including but not limited to, liver, spleen, kidney, lung, intestine, brain, heart, muscle, pancreas, biopsy material, and the like. The skilled artisan will appreciate that lysates, extracts, or material obtained from any of the above exemplary biological samples are also within the scope of the invention. Tissue culture cells, including explanted material, primary cells, secondary cell lines, and the like, as well as lysates, extracts, or materials obtained from any cells, are also within the meaning of the term biological sample as used herein. Microorganisms and viruses that may be present on or in a sample are also within the scope of the invention. Materials obtained from forensic settings are also within the intended meaning of the term sample.

The term "substrate" as used herein refers to one or more surfaces that a molecular complex or at least part of a molecular complex can interact with or bind to, either directly or indirectly. Substrate surfaces are typically planar, but can comprise a wide variety of topographies, including combinations of topographies on the same surface. The skilled artisan will appreciate that the suitability of a particular substrate, including its topography and composition, typically depends on the type(s) of molecular complex to be detected and the detection technique(s) employed.

II. Reagents

As used herein, the terms antibody and antibodies are used in a broad sense, to include not only intact antibody molecules, for example but not limited to immunoglobulin A, immunoglobulin G and immunoglobulin M, but also any immunoreactive component(s) of an antibody molecule that immunospecifically bind to at least one epitope. Such immunoreactive components include but are not limited to, FAb fragments, FAb' fragments, FAb'2 fragments, single chain antibody fragments (scFv), miniantibodies, diabodies, crosslinked antibody fragments, Affibody® molecules, and the like. Immunoreactive products derived using antibody engineering or protein engineering techniques are also expressly within the meaning of the term antibodies. Detailed descriptions of antibody and/or protein engineering, including relevant protocols, can be found in, among other places, J. Maynard and G. Georgiou, Ann. Rev. Biomed. Eng. 2:339–76 (2000); Antibody Engineering, R. Kontermann and S. Dübel, eds., Springer Lab Manual, Springer Verlag (2001); A. Wörn and A. Plückthun, J. Mol. Biol. 305:989–1010 (2001); J. McCafferty et al., Nature 348:552–54 (1990); Müller et al., FEBS Letter, 432:45–9 (1998); A. Plückthun and P. Pack, Immunotechnology, 3:83–105 (1997); U.S. Pat. No. 5,831,012; and S. Paul, Antibody Engineering Protocols, Humana Press (1995).

The skilled artisan will appreciate that antibody can be obtained from a variety of sources, including but not limited to polyclonal antibody, monoclonal antibody, monospecific antibody, recombinantly expressed antibody, humanized antibody, plantibodies, and the like; and can be obtained from a variety of animal species, including rabbit, mouse, goat, rat, human, horse, bovine, guinea pig, chicken, sheep, donkey, human, and the like. A wide variety of antibody is commercially available and custom-made antibody can be obtained from a number of contract labs. Detailed descriptions of antibodies, including relevant protocols, can be found in, among other places, Current Protocols in Immunology, Coligan et al., eds., John Wiley & Sons (1999, including updates through August 2003); The Electronic Notebook; Basic Methods in Antibody Production and Characterization, G. Howard and D. Bethel, eds., CRC Press (2000); J. Goding, Monoclonal Antibodies: Principles and Practice, 3d Ed., Academic Press (1996); E. Harlow and D. Lane, Using Antibodies, Cold Spring Harbor Lab Press (1999); P. Shepherd and C. Dean, Monoclonal Antibodies: A Practical Approach, Oxford University Press (2000); A. Johnstone and M. Turner, Immunochemistry 1 and 2, Oxford University Press (1997); C. Borrebaeck, Antibody Engineering, 2d ed., Oxford university Press (1995); A. Johnstone and R. Thorpe, Immunochemistry in Practice, Blackwell Science, Ltd. (1996); H. Zola, Monoclonal Antibodies: Preparation and Use of Monoclonal Antibodies and Engineered Antibody Derivatives (Basics: From Background to Bench), Springer Verlag (2000); and S. Hockfield et al., Selected Methods for Antibody and Nucleic Acid Probes, Cold Spring Harbor Lab Press (1993). Additionally, a vast number of commercially available antibodies, including labeled or unlabeled; polyclonal, monoclonal, and monospecific antibodies, as well as immunoreactive components thereof; custom antibody suppliers, and the like can be found on the World Wide Web at, among other places, the Antibody Search page at biocompare.com, the Antibody Resource Page at antibodyresource.com, and the Antibody Explorer page at sigmaaldrich.com.

Aptamers include nucleic acid aptamers (i.e., single-stranded DNA molecules or single-stranded RNA molecules) and peptide aptamers. Aptamers bind target molecules in a highly specific, conformation-dependent manner, typically with very high affinity, although aptamers with lower binding affinity can be selected if desired. Aptamers have been shown to distinguish between targets based on very small structural differences such as the presence or absence of a methyl or hydroxyl group and certain aptamers can distinguish between D- and L-enantiomers. Aptamers have been obtained that bind small molecular targets, including drugs, metal ions, and organic dyes, peptides, biotin, and proteins, including but not limited to streptavidin, VEGF, and viral proteins. Aptamers have been shown to retain functional activity after biotinylation, fluorescein labeling, and when attached to glass surfaces and microspheres.

Nucleic acid aptamers, including speigelmers, are identified by an in vitro selection process known as systematic evolution of ligands by exponential amplification (SELEX). In the SELEX process very large combinatorial libraries of oligonucleotides, for example $10^{14}$ to $10^{15}$ individual sequences, often as large as 60–100 nucleotides long, are routinely screened by an iterative process of in vitro selection and amplification. Most targets are affinity enriched within 8–15 cycles and the process has been automated allowing for faster aptamer isolation. Peptide aptamers are typically identified by several different protein engineering techniques known in the art, including but not limited to, phage display, ribosome display, mRNA display, selectively infected phage technology (SIP), and the like. The skilled artisan will understand that nucleic acid aptamers and peptide aptamers can be obtained following conventional procedures and without undue experimentation. Detailed descriptions of aptamers, including relevant protocols, can be found in, among other places, L. Gold, J. Biol. Chem., 270(23):13581–84 (1995); L. Gold et al., Ann. Rev. Biochem. 64:763–97 (1995); S. Jayashena, Clin. Chem., 45:1628–50 (1999); V. Sieber et al., Nat. Biotech. 16:955–60 (1998); L. Jermutus et al., Curr. Opin. Biotech. 9:534–48 (1998); D. Wilson and J. Szostak, Ann. Rev. Biochem. 68:611–47 (1999); L. Jermutus et al., Eur. Biophys. J., 31:179–84 (2002); G. Connell et al., Biochem., 32:5497–5502 (1993); M. Famulok et al., Acc. Chem. Res. 33:591–99 (2000); W. James, Curr. Opin. Pharmacol., 1:540–46 (2001); J. Cox. Et al., Nucl. Acid Res. 30(20):e18 (2002); S. Clark and V. Remcho, Electrophoresis 23:1335–40, 2002; A. Tahiri-Alaoui et al., Nuc. Acid Res. 30(10):e45 (2002); A. Kopylov and V. Spiridonova, Molecular Biology 34:940–54 (2000); J. Blum et al., Proc. Natl. Acad. Sci., 97:2241–46 (2000); Phage Display: A Laboratory Manual, C. Barbas, D. Burton, J. Scott, and G. Silverman, eds., Cold Spring Harbor Laboratory Press (2001); S. Jung et al., J. Mol. Biol. 294:163–80 (1999); N. Raffler et al., Chem. & Biol., 10:69–79 (2003); A. Plückthun et al., Adv. Protein Chem. 55:367–403 (2000); Amstutz et al., Curr. Opin. Biotech., 12:400–05 (2001); J. Hanes and A. Pluckthun, Proc. Natl. Acad. Sci., 94:4937–42 (1997); Protein-Protein Interactions, A Molecular Cloning Manual, E. Golemis, ed., Cold Spring Harbor Press (2001); C. Krebber et al., J. Mol. Biol. 268:607–18 (1997); S. Spada et al., Biol. Chem., 378:445–56 (1997); B. Wlotzka et al., Proc. Natl. Acad. Sci., 99:8898–8902 (2002); R. Roberts and J. Szostak, Proc. Natl. Acad. Sci., 94:12297–12302 (1997); P. Colas et al., Proc. Natl. Acad. Sci., 97:13720–25 (2000); and Y. Jiang et al., Anal. Chem., 75:2112–16 (2003).

The term "primers" as used herein refers to oligonucleotides that are designed to hybridize with at least one analyte, at least one analyte surrogate, or both, in a sequence-specific manner. Primers typically serve as initiation sites for certain amplification techniques, including but not limited to, primer extension and the polymerase chain reaction (PCR).

Probes, according to the teachings herein, are molecules or assemblies that are designed to combine with at least one analyte, at least one analyte surrogate, or both; and can, under appropriate conditions, form at least part of at least one molecular complex. Probes typically are part of at least one probe set, comprising at least one first probe and at least one second probe. In certain embodiments, however, at least one probe set can comprise only first probes or second probes, but not both first probes and second probes. In certain embodiments, at least one probe of at least one probe set comprises at least one amino acid, at least one ribonucleotide, at least one deoxyribonucleotide, at least one peptide nucleic acid (PNA), at least one pseudocomplementary peptide nucleic acid (pcPNA), or combinations thereof.

Probes comprise at least one reaction portion that allow them to bind to or interact with at least one analyte, at least one part of at least one analyte, at least one analyte surrogate, at least part of an analyte surrogate, or combinations thereof; typically in a sequence-specific, a confirmation-specific manner, or both; for example but not limited to nucleic acid hybridization, antigen-antibody binding, aptamer-target binding, and the like. In certain embodiments, at least one probe of at least one probe set further comprises an identity portion or at least part of an identity portion comprising at least one coded molecular tag; or an analytical portion or at least part of an analytical portion; but typically not both an identity portion and an analytical portion. In certain embodiments, the identity portion is within the reaction portion, coextensive with the reaction portion, or overlaps at least part of the reaction portion. In certain embodiments, the analytical portion is within the reaction portion, coextensive with the reaction portion, or overlaps at least part of the reaction portion.

The reaction portions of nucleic acid probes are of sufficient length to permit specific annealing to complementary sequences in corresponding analytes, corresponding analyte surrogates, or both; as are primers. The criteria for designing sequence-specific nucleic acid probes and primers are well known to persons of ordinary skill in the art. Detailed descriptions of nucleic acid probe and primer design can be found in, among other places, Diffenbach and Dveksler, PCR Primer, A Laboratory Manual, Cold Spring Harbor Press (1995); Rapley; Schena; and Kwok et al., Nucl. Acid Res. 18:999–1005 (1990). Primer and probe design software programs are also commercially available, for example, Primer Premier 5, PREMIER Biosoft, Palo Alto, Calif.; Primer Designer 4, Sci-Ed Software, Durham, N.C.; Primer Detective, ClonTech, Palo Alto, Calif.; Lasergene, DNASTAR, Inc., Madison, Wis.; and iOligo, Caesar Software, Portsmouth, N.H.

In certain embodiments, at least one identity portion, at least part of the identity portion, or both comprise at least one coded molecular tag and at least one capture ligand. In certain embodiments, at least one analytical portions, at least part of an analytical portion, or both, comprises at least one affinity tag, including but not limited to, at least one biotin moiety, at least one epitope tag; at least one antibody molecule; at least one fluorophore; at least one mobility modifier; at least one hybridization tag; at least one aptamer sequence; or combinations thereof.

In certain embodiments, at least one probe comprises a reaction portion or part of a reaction portion that is designed to hybridize in a sequence-specific manner with a complementary region, i.e., the target sequences of at least one analyte, at least one analyte surrogate, or both. In certain embodiments, at least part of the reaction portion of at least one first probe, at least part of the reaction portion of at least one corresponding second probe, or both at least part of the reaction portion of the at least one first probe and at least part of the reaction portion of the at least one corresponding second probe comprise at least one amino acid, at least one ribonucleotide, at least one deoxyribonucleotide, at least one PNA, at least one pcPNA, or combinations thereof.

Figure 4A:
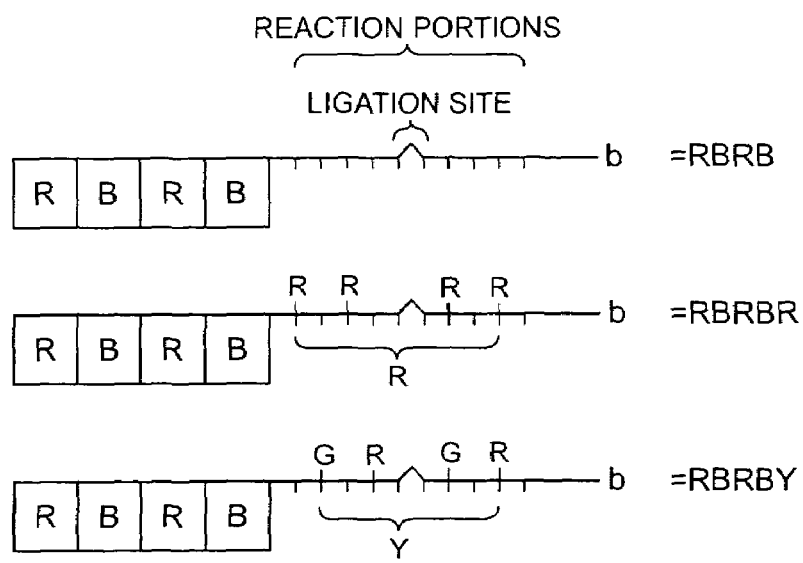
FIG. 4: schematically depicts several illustrative molecular complexes, each comprising an identity portion comprising the same coded molecular tag RBRB.

Typically, the presence of an analyte in a sample can be determined based on individually detecting at least one corresponding molecular complex or at least part of a corresponding molecular complex, and identifying the order of the reporter group species. In certain embodiments, the identity of a molecular complex can not be determined simply by identifying the order of the reporter group species in the corresponding identity portion(s). In certain embodiments, the same identity portion is used to generate probes for different molecular complexes, therefore the identity of such molecular complexes is determined by a combination of the order of reporter groups in the coded molecular tag(s) and at least one additional information element not present in the identity portion. For example but not limited to, at least one reporter group species in the analytical portion (see, e.g., FIGS. 3 and 4B), at least one reporter group species present in at least one reaction portion or the combined reaction portions (see, e.g., FIG. 4A), or an inherent property of a molecular complex comprising a single probe (see, e.g., FIG. 1B). Exemplary inherent properties of such molecular complexes include without limitation molecular weight and electrophoretic mobility. For example but not limited to, a particular coded molecular tag can be used to assemble one probe species specific for a small peptide analyte and also to assemble a different probe species specific for a large protein analyte (the relative molecular weights of the two probes is similar), so that the molecular weight of the peptide analyte-molecular complex is substantially less than the molecular weight of the large protein analyte-molecular complex. These two illustrative molecular complexes can be separated by, for example, size exclusion chromatography. Thus, in this example, the identity of both molecular complexes is determined by a combination of the order of the reporter group species in the coded molecular tag and the molecular weight of their respective molecular complexes.

The codespace of an identity portion is at least one determinant of the number of unique identifier tags or addresses that can be created and can limit the number of different species of analyte that can be determined in a reaction, particularly multiplex reactions. The theoretical number of unique identifier tags that can be created within a codespace depends in part on the number of reporter group species to be used, the properties of those reporter group species, the number of usable labeling positions in the template, and the detection method(s) employed.

Typically, the template must be large enough so that the reporter groups at different labeling positions can be individually resolved. In certain embodiments, for individual fluorophores to be optically resolved the labeling positions are separated by about 0.8 micrometers ($\mu$m). This spacing exceeds what is typically required to avoid quenching between fluorescent reporter groups. Thus, in an exemplary codespace comprising 6 labeling positions, a template with a minimum length of about 5 $\mu$m is typically needed. In certain embodiments, individual fluorophores to be optically resolved are separated by about 0.9 $\mu$m, about 0.8 $\mu$m, about 0.7 $\mu$m, about 0.6 $\mu$m, about 0.5 $\mu$m, about 0.4 $\mu$m, about 0.3 $\mu$m, about 0.2 $\mu$m, about 0.1 $\mu$m, or combinations thereof. The skilled artisan will understand that optical resolution depends on several factors including without limitation, the choice of the detection system components and the distance between the reporter groups because of, among other things, energy transfer between closely positioned fluorescent reporter groups, including quenching and self-quenching.

The skilled artisan will appreciate that the number of unique addresses available for identifying molecules of interest, including without limitation, molecular complexes and analytes, can be increased beyond the number available based on codespace alone. For example, the same coded molecular tag can be used to form different molecular complexes if (i) they have different affinity portions; (ii) they have different capture ligands; (iii) they have labeled reaction portions, including color complementation; or combinations thereof. Additionally, the same coded molecular tag can be used with the different molecular complexes based on other differences, including without limitation, the presence of absence of cleavable linkers; different capture ligands in the identity portion, the reaction portion, or both; and so forth.

FIG. 4 schematically depicts a multiplicity of distinguishable illustrative molecular complexes, each comprising the same coded molecular tag RBRB. In FIG. 4A, three biotinylated molecular complexes are shown, each comprising the same coded molecular tag comprising red (R) and blue (B) fluorescent reporter group species in the ordered pattern RBRB and a biotin capture ligand (b). The ligation site is shown as "Λ", and the combined reaction portions of each molecular complex are shown as "tick" marks between the coded molecular tag and the biotin capture ligand. The combined reaction portions of the upper molecular complex lack reporter groups, thus the order of reporter group species in the molecular complex is RBRB. The combined reaction portions of the middle molecular complex comprise the "R" reporter group species, thus the order of reporter group species in the molecular complex is RBRBR. The combined reaction portions of the bottom molecular complex in FIG. 4A comprises both the "R" reporter group species and a green fluorescent reporter group species (G) that by color complementation appear as yellow ("Y") when individually detected using certain optical SMD techniques. Thus, the order of reporter group species the bottom molecular complex is RBRBY.

Figure 4B:
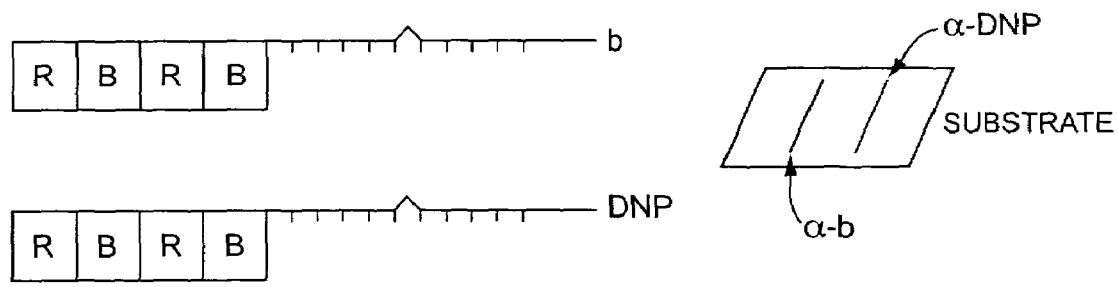

FIG. 4B depicts two molecular complexes, each comprising the same coded molecular tag comprising the ordered pattern RBRB. The top exemplary molecular complex in FIG. 4B comprises at least one biotin capture ligand ("b") and the bottom molecular complex comprises at least one DNP capture ligand ("DNP"). When these two molecular complexes are combined with the illustrative patterned substrate, wherein the pattern comprises one line of anti-biotin antibody capture moieties (shown as α-b) and one line of anti-DNP antibody capture moieties (shown as α-DNP), the two molecular complexes are spatially separated on the substrate when they bind their respective capture moieties.

Figure 4C:
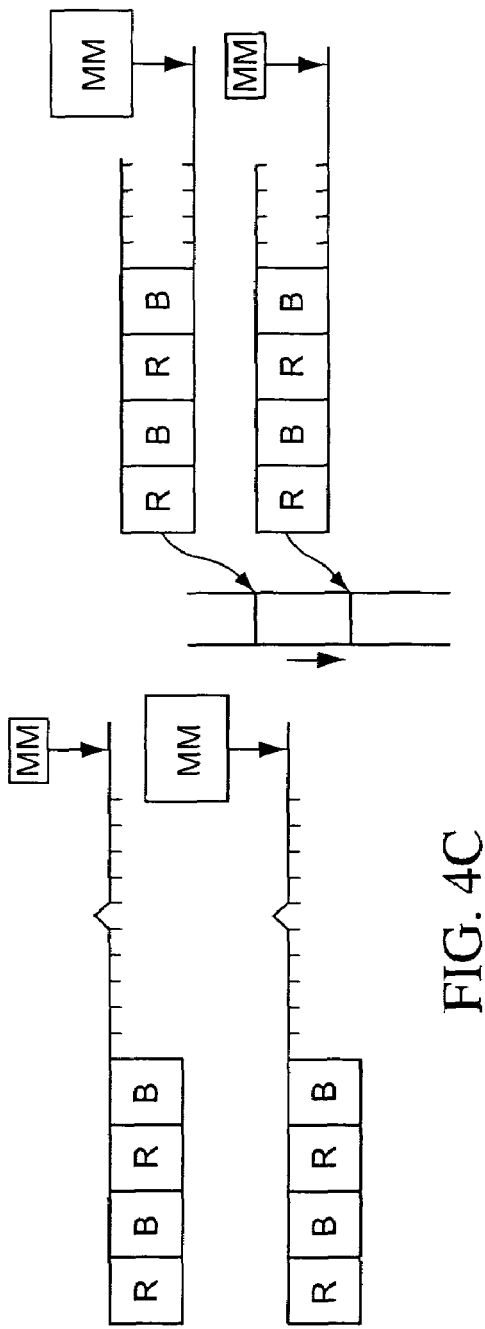
Figure 4D:
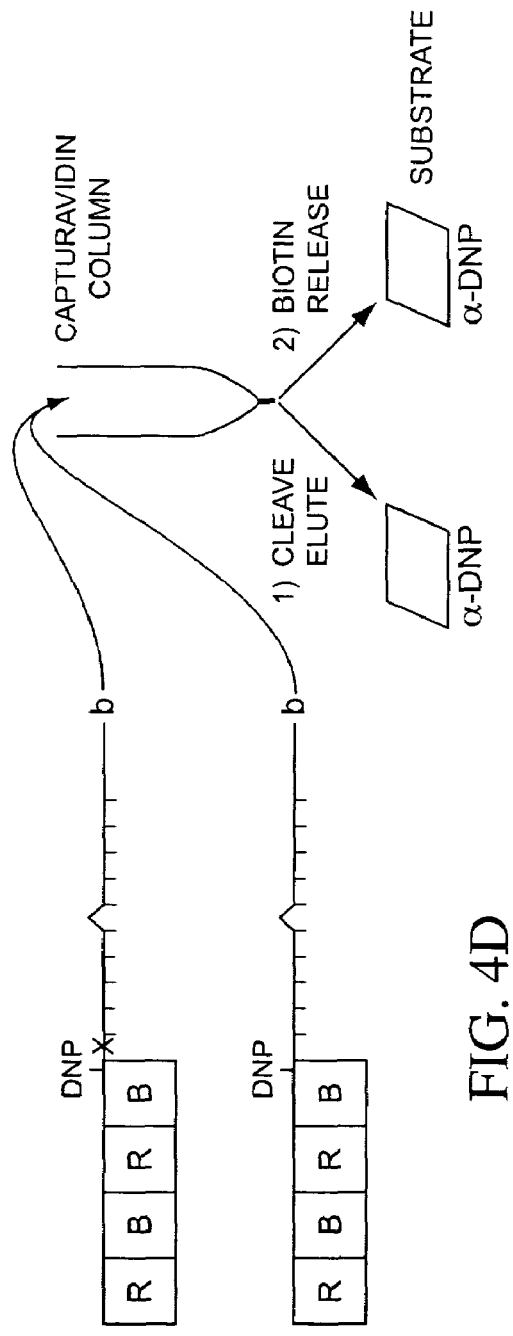

Two different molecular complexes are shown in FIG. 4C, each comprising the same coded molecular tag, shown as RBRB, but with different analytical portions, here different mobility modifiers. When these two exemplary molecular complexes are separated using, e.g., mobility-dependent analytical techniques, they can be isolated independently and individually detected. FIG. 4D schematically depicts two different molecular complexes, each comprising an at least one biotin moiety and an identity portion comprising the coded molecular tag RBRB and at least one DNP moiety. The top exemplary molecular complex comprises a cleavable linker between the reaction portion and the coded molecular tag, while the bottom exemplary molecular complex does not comprise a cleavable linker. In this illustrative embodiment, the two different molecular complexes are separated using a CaptAvidin chromatography column. The column comprising the bound molecular complexes is first treated with an appropriate cleavage reagent to release the cleavable component comprising the coded molecular tag from the top, but not the bottom, molecular complexes. The cleavable components are combined with a first substrate comprising anti-DNP antibody capture moieties and individually detected using an appropriate SMD. The CaptAvidin column is next treated with biotin to reverse the CaptAvidin-biotinylated molecular complex binding, releasing the bottom exemplary molecular complexes. These released molecular complexes are combined with a second substrate comprising anti-DNP antibody capture moieties and individually detected using an appropriate SMD.

III. Techniques

Ligation

Ligation according to the present invention comprises any enzymatic or chemical process wherein an inter-nucleotide linkage is formed between the opposing ends of nucleic acid sequences that are adjacently hybridized to a template. Additionally, the opposing ends of the annealed nucleic acid probes must be suitable for ligation (suitability for ligation is a function of the ligation method employed). The internucleotide linkage can include, but is not limited to, phosphodiester bond formation. Such bond formation can include, without limitation, those created enzymatically by at least one DNA ligase or at least one RNA ligase, for example but not limited to, T4 DNA ligase, T4 RNA ligase, *Thermus thermophilus* (Tth) ligase, *Thermus aquaticus* (Taq) DNA ligase, or *Pyrococcus furiosus* (Pfu) ligase.

Other internucleotide linkages include, without limitation, covalent bond formation between appropriate reactive groups such as between an α-haloacyl group and a phosphothioate group to form a thiophosphorylacetylamino group, a phosphorothioate a tosylate or iodide group to form a 5'-phosphorothioester, and pyrophosphate linkages.

Chemical ligation can, under appropriate conditions, occur spontaneously such as by autoligation. Alternatively, "activating" or reducing agents can be used. Examples of activating and reducing agents include, without limitation, carbodiimide, cyanogen bromide (BrCN), imidazole, 1-methylimidazole/carbodiimide/cystamine, N-cyanoimidazole, dithiothreitol (DTT) and ultraviolet light.

Figure 6A:
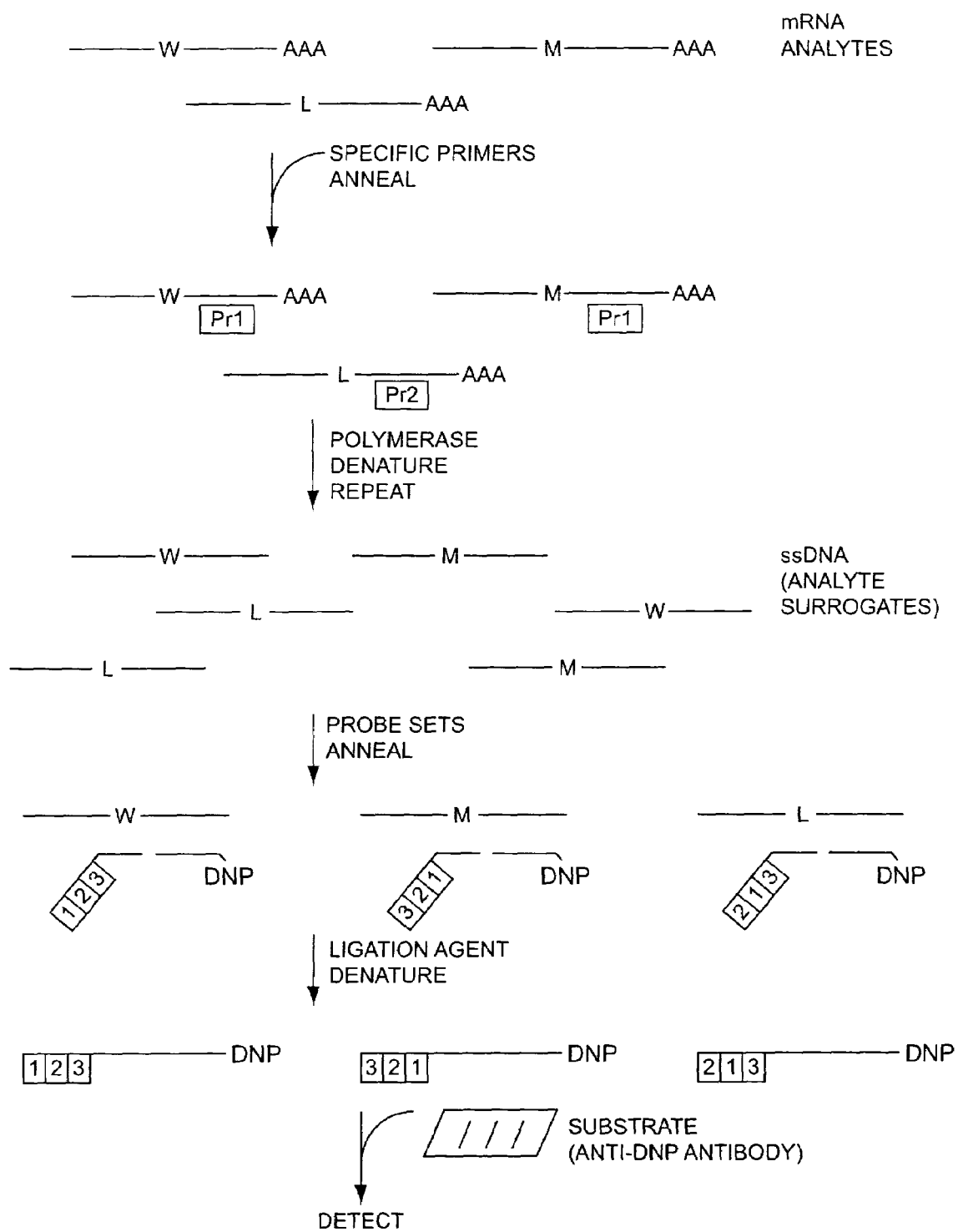
FIG. 6: schematically depicts exemplary methods and probes for determining the presence of nucleic acid analytes in a sample comprising amplification.

Ligation generally comprises at least one cycle of ligation, i.e., the sequential procedures of: hybridizing the reaction portions of a first probe and a corresponding second probe, that are suitable for ligation, to their respective complementary target regions; ligating the 3' end of the upstream probe with the 5' end of the downstream probe to form a ligation product; and denaturing the nucleic acid duplex to separate the ligation product from the analyte or analyte surrogate (see, e.g., FIG. 6A). The ligation cycle may or may not be repeated, for example, without limitation, by thermocycling the ligation reaction to linearly amplify the ligation product that can serve as at least one analyte surrogate.

Also within the scope of the invention are ligation techniques such as gap-filling ligation, including, without limitation, gap-filling OLA and LCR, bridging oligonucleotide ligation, and correction ligation. Descriptions of these techniques can be found, among other places, in U.S. Pat. No. 5,185,243, published European Patent Applications EP 320308 and EP 439182, and PCT Publication Nos. WO 90/01069 and WO 01/57268.

A "ligation agent", according to the present invention, can comprise any number of enzymatic or chemical (i.e., non-enzymatic) reagents. For example, ligase is an enzymatic ligation reagent that, under appropriate conditions, forms phosphodiester bonds between the 3'-OH and the 5'-phosphate of adjacent nucleotides in DNA molecules, RNA molecules, or hybrids. Temperature sensitive ligases, include, but are not limited to, bacteriophage T4 ligase and *E. coli* ligase. Thermostable ligases include, but are not limited to, Taq ligase, Tfl ligase, Tth ligase, Tth HB8 ligase, *Thermus* species AK16D ligase and Pfu ligase. The skilled artisan will appreciate that any number of thermostable ligases, including DNA ligases and RNA ligases, can be obtained from thermophilic or hyperthermophilic organisms, for example, certain species of bacteria and archaebacteria; and that such ligases can be useful in the methods and kits of the invention.

Chemical ligation agents include, without limitation, activating, condensing, and reducing agents, such as carbodiimide, cyanogen bromide (BrCN), N-cyanoimidazole, imidazole, 1-methylimidazole/carbodiimide/cystamine, dithiothreitol (DTT) and ultraviolet light. Autoligation, i.e., spontaneous ligation in the absence of a ligating agent, is also within the scope of the invention. Detailed protocols for chemical ligation methods and descriptions of appropriate reactive groups can be found in, among other places, Xu et al., Nucleic Acid Res., 27:875–81 (1999); Gryaznov and Letsinger, Nucleic Acid Res. 21:1403–08 (1993); Gryaznov et al., Nucleic Acid Res. 22:2366–69 (1994); Kanaya and Yanagawa, Biochemistry 25:7423–30 (1986); Luebke and Dervan, Nucleic Acids Res. 20:3005–09 (1992); Sievers and von Kiedrowski, Nature 369:221–24 (1994); Liu and Taylor, Nucleic Acids Res. 26:3300–04 (1999); Wang and Kool, Nucleic Acids Res. 22:2326–33 (1994); Purmal et al., Nucleic Acids Res. 20:3713–19 (1992); Ashley and Kushlan, Biochemistry 30:2927–33 (1991); Chu and Orgel, Nucleic Acids Res. 16:3671–91 (1988); Sokolova et al., FEBS Letters 232:153–55 (1988); Naylor and Gilham, Biochemistry 5:2722–28 (1966); and U.S. Pat. No. 5,476,930.

When used in the context of the present invention, "suitable for ligation" refers to at least one first probe and at least one corresponding second probe, wherein each probe comprises an appropriately reactive group based on the ligation reaction employed. Exemplary reactive groups include, but are not limited to, a free hydroxyl group on the 3' end of the upstream probe and a free phosphate group on the 5' end of the downstream probe, phosphorothioate and tosylate or iodide, esters and hydrazide, $RC(O)S^-$, haloalkyl, $RCH_2S$ and α-haloacyl, thiophosphoryl and bromoacetoamido groups, and S-pivaloyloxymethyl-4-thiothymidine.

B. Amplification

Amplification according to the present invention encompasses any technique by which at least a part of at least one analyte or at least one analyte surrogate is copied, typically in a template-dependent manner, including without limitation, a broad range of techniques for amplifying nucleic acid sequences, either linearly or exponentially. The amplification product of an analyte or part of an analyte is typically an analyte surrogate. Exemplary amplification methods include ligase chain reaction (LCR), ligase detection reaction (LDR), polymerase chain reaction (PCR), primer extension, strand displacement amplification (SDA), multiple displacement amplification (MDA), nucleic acid strand-based amplification (NASBA), and the like, including multiplex versions and combination thereof, for example but not limited to, OLA/PCR, PCR/LDR, PCR/LCR (also known as combined chain reaction-CCR), and the like. Descriptions of such techniques can be found in, among other places, Sambrook and Russell; Sambrook et al.; Ausbel et al.; PCR Primer: A Laboratory Manual, Diffenbach, Ed., Cold Spring Harbor Press (1995); The Electronic Protocol Book, Chang Bioscience (2002)("The Electronic Protocol Book"); Msuih et al., J. Clin. Micro. 34:501–07 (1996); The Nucleic Acid Protocols Handbook, R. Rapley, ed., Humana Press, Totowa, N.J. (2002)("Rapley"); U.S. Pat. No. 6,027,998; Barany et al., PCT Publication No. WO 97/31256; Wenz et al., PCT Publication No. WO 01/92579; Ehrlich et al., Science 252:1643–50 (1991); Innis et al., PCR Protocols: A Guide to Methods and Applications, Academic Press (1990); Favis et al., Nature Biotechnology 18:561–64 (2000); and Rabenau et al., Infection 28:97–102 (2000); Belgrader, Barany, and Lubin, Development of a Multiplex Ligation Detection Reaction DNA Typing Assay, Sixth International Symposium on Human Identification, 1995 (available on the world wide web at: promega.com/geneticidproc/ussymp6proc/blegrad.html); LCR Kit Instruction Manual, Cat. #200520, Rev. #050002, Stratagene, 2002; Barany, Proc. Natl. Acad. Sci. USA 88:188–93 (1991); Bi and Sambrook, Nucl. Acids Res. 25:2924–2951 (1997); Zirvi et al., Nucl. Acid Res. 27:e40i–viii (1999); Dean et al., Proc Natl Acad Sci USA 99:5261–66 (2002); Barany and Gelfand, Gene 109:1–11 (1991); Walker et al., Nucl. Acid Res. 20:1691–96 (1992); Polstra et al., BMC Inf. Dis. 2:18-(2002); and Landegren et al., Science 241:1077–80 (1988).

In certain embodiments, amplification comprises at least one cycle of the sequential procedures of: hybridizing at least one probe or at least one primer to target sequences in at least one analyte or at least one analyte surrogate; synthesizing at least one strand of nucleotides in a template-dependent manner using a polymerase; and denaturing the newly-formed nucleic acid duplex to separate the strands. The cycle may or may not be repeated. Amplification methods can comprise thermocycling or can be performed isothermally. In certain embodiments, at least part of at least one analyte, at least part of an analyte surrogate, or combinations thereof, is amplified before, during, or after molecular complex formation.

In certain embodiments, the methods and kits disclosed herein comprise at least one polymerase, at least one ligation agent, or at least one polymerase and at least one ligation agent. In certain embodiments, methods comprise ligation reactions; primer extension, including but not limited to "gap filling" reactions; transcription, including but not limited to reverse transcription; translation; or combinations thereof, including but not limited to, coupled in vitro transcription/translation systems.

Primer extension according to the present invention is a process that comprises elongating a primer that is annealed to a template in the 5' to 3' direction using a template-dependent polymerase. According to certain embodiments, with appropriate buffers, salts, pH, temperature, and nucleotide triphosphates, including analogs thereof, i.e., under appropriate conditions, a polymerase incorporates nucleotides complementary to the template strand starting at the 3'-end of an annealed probe or primer, to generate a complementary strand. In certain embodiments, primer extension can be used to fill a gap between two probes of a probe set that are hybridized to target sequences of at least one analyte, at least one analyte surrogate, or combinations thereof. In certain embodiments, the polymerase used for primer extension lacks or substantially lacks 5' exonuclease activity.

FIG. 6 schematically depicts exemplary methods for determining the presence of nucleic acid analytes in a sample, comprising amplification. In FIG. 6A, mRNA analytes (shown as W, M, or L, each with a "poly A" tail) are combined with specific primers (shown as Pr1 or Pr2) and analyte surrogates comprising single-stranded DNA molecules (shown as M, L, or W, but without poly A tails) are generated by primer extension. Three exemplary probe sets, each comprising one probe with a reaction portion and identity portion comprising a coded molecular tag (shown as 123, 321, or 213) and a second probe comprising a reaction portion and an analytical portion comprising DNP are hybridized to the ssDNA analyte surrogates, forming molecular complexes. Ligation product molecular complexes are formed in the presence of an appropriate ligation agent. The ligation product molecular complexes are combined with a substrate comprising a patterned surface including anti-DNP antibody capture moieties and individually detected using an appropriate SMD technique.

C. Separation

Separating comprises any process that removes at least some unreacted components, at least some reagents, or both some unreacted components and some reagents from at least one molecular complex, at least part of at least one molecular complex, or combinations thereof. In certain embodiments, at least one molecular complex, at least part of a molecular complex, or combinations thereof, are separated from unreacted components and reagents, including but not limited to unreacted molecular species present in the sample, ligation reagents, amplification reagents, for example, but not limited to, unbound/unhybridized probes, primers, enzymes, co-factors, unbound sample components, nucleotides, and the like. The skilled artisan will appreciate that a number of well known separation techniques will be useful with certain methods disclosed herein.

Exemplary separation techniques include gel electrophoresis, including but not limited to isoelectric focusing and capillary electrophoresis; dielectrophoresis; sorting, including but not limited to fluorescence-activated sorting techniques; chromatography, including but not limited to HPLC, FPLC, size exclusion (gel filtration) chromatography, affinity chromatography, ion exchange chromatography, hydrophobic interaction chromatography, immunoaffinity chromatography, and reverse phase chromatography; ligand-receptor binding, such as biotin-avidin, biotin-streptavidin, maltose-maltose binding protein (MBP), calcium-calcium binding peptide; aptamer-target binding; zip code hybridization; and the like. Detailed discussion of separation techniques can be found in, among other places, Rapley; Sambrook et al.; Sambrook and Russell; Ausbel et al.; Molecular Probes Handbook; Pierce Applications Handbook; Capillary Electrophoresis: Theory and Practice, P. Grossman and J. Colburn, eds., Academic Press (1992); Wenz and Schroth, PCT International Publication No. WO 01/92579; M. Ladisch, Bioseparations Engineering: Principles, Practice, and Economics, John Wiley & Sons (2001); and Liebler, Introduction to Proteomics, Humana Press (2002).

In certain embodiments, separation comprises binding at least one molecular complex or at least part of a molecular complex to at least one substrate, either directly or indirectly; for example but not limited to, indirectly binding a molecular complex or at least part of a molecular complex to a glass substrate, wherein the molecular complex comprises at least one capture ligand such as biotin, and the substrate comprises at least one capture moiety, such as a streptavidin, avidin, CaptAvidin, or NeutrAvidin; or vice versa. The skilled artisan will understand that certain methods comprise at least two different separations, for example a first bulk separation that is typically, but need not be, analytical portion dependent; and a second separation wherein at least one molecular complex comprising at least one capture ligand or at least part of a molecular complex comprising at least one capture ligand is tethered, or attached to a substrate comprising at least one capture moiety. For example, but without limitation, separating at least one molecular complex or at least part of a molecular complex comprising biotin and at least one mobility modifier by capillary electrophoresis and then tethering or attaching the biotinylated molecular complex indirectly to a substrate comprising streptavidin; or separating at least one molecular complex or at least part of a molecular complex comprising an hybridization tag capture ligand by RP-HPLC and then indirectly binding the at least one molecular complex or at least part of a molecular complex to a glass, mica, or silicon substrate comprising hybridization tag complement capture moieties. In certain embodiments, at least one analytical portion comprises at least one capture ligand, at least one reaction portion comprises at least one capture ligand, at least one identity portion comprises at least one capture ligand, or combinations thereof.

In certain embodiments, at least one substrate further comprises at least one capture moiety. In certain embodiments, at least one substrate is derivatized or coated to enhance the binding of at least one capture moiety, at least one molecular complex, at least one part of a molecular complex, or combinations thereof. Exemplary substrate treatments and coatings include poly-lysine coating; aldehyde treatment; amine treatment; epoxide treatment; sulphur-based treatment (e.g., isothiocyanate, mercapto, thiol); coating with avidin, streptavidin, biotin, or derivatives thereof; and the like. Detailed descriptions of derivatization techniques and procedures to enhance capture moiety binding can be found in, among other places, Microarray Analysis; G. MacBeath and S. Schreiber, Science 289:1760–63 (2000); A, Talapatra, R. Rouse, and G. Hardiman, Proteogenomics 3:1–10 (2002); Microarray Methods and Applications-Nuts and Bolts, G. Hardiman, ed., DNA Press (2003); B. Houseman and M. Mrksich, Trends in Biochemistry 20:279–81 (2002); S. Carmichael et al., A Simple Test Method for Covalent Binding Microarray Surfaces, NoAb BioDiscoveries Microarray Technical Note #010516SC; P. Galvin, An introduction to analysis of differential gene expression using DNA microarrays, The European Working Group on CTFR Expression (4-02-2003); and Zhu et al., Curr. Opin. Chem. Biol. 7:55–63 (2003). The skilled artisan will appreciate that lessons learned and techniques employed in the nucleic acid and protein microarray arts are generally applicable to binding, attaching, or tethering molecular complexes or parts of molecular complexes to substrates. Pretreated substrates and derivatization reagents and kits are commercially available from several sources, including CEL Associates, Pearland Tex.; Genetix, Ltd.; Molecular Probes, Eugene Oreg.; Quantifoil MicroTools GmbH, Jena Germany; Xenopore Corp., Hawthorne N.J.; NoAb BioDiscoveries, Mississauga, Ontario, Canada; TeleChem International, Sunnyvale, Calif.; CLONTECH Laboratories, Inc., Palo Alto Calif.; Asper Biotech, Tartu Estonia; and Accelr8 Technology Corp., Denver Colo. Alternate substrates for use with the compositions, methods, and kits disclosed herein are ProteinPrint™ Films, commercially available from Aspira Biosystems, Inc., So. San Francisco, Calif. In certain embodiments, the substrate bound capture moiety comprises at least one amino acid, for example but not limited to, antibodies, peptide aptamers, peptides, avidin, streptavidin, biotin, and the like. In certain embodiments, the substrate bound capture moiety comprises at least one nucleotide, for example but not limited to, hybridization tag complements, nucleic acid aptamers, PNAs, pcPNAs, and the like.

D. Detection

Detection typically comprises individually detecting at least one molecular complex or at least part of at least one molecular complex to determine the presence of the corresponding analyte. Typically individually detecting comprises identifying the order of the reporter group species in at least one molecular complex or at least part of a molecular complex using at least one SMD technique. The order of reporter group species is determined collectively, i.e., from an intact or substantially intact coded molecular tag, rather than a group of detached subunits or fragments. In certain embodiments, at least one molecular complex or at least part of a molecular complex is individually detected while tethered or attached to a substrate via at least one capture ligand-capture moiety interaction, at least one electrostatic interaction, or both. In certain embodiments, at least one molecular complex or at least part of a molecular complex is individually detected in solution. In certain embodiments, at least one molecular complex or at least part of a molecular complex is individually detected after being isolated on a substrate or in a dilute solution so that at least one molecular complex or at least part of a molecular complex are spatially separated from other molecular complexes or parts of molecular complexes. The skilled artisan will appreciate that as the concentration of molecular complexes to be detected in a given volume or area decreases, the number of spatially separated molecular complexes that can be individually detected typically increases.

In certain embodiments, individually detecting comprises optical SMD techniques that comprise frequency-modulated absorption, laser-induced fluorescence, or both. The skilled artisan will appreciate that, due to high signal-to-noise ratios and low background, laser-induced fluorescence is frequently used. To reduce background interference, such as from Raman scattering, Rayleigh scattering, and impurity fluorescence, high-performance optical filters and ultrapure reagents are typically employed with confocal, near-field, and evanescent wave microscopy configurations.

FIG. 5 schematically depicts an exemplary method for individually detecting at least one bound molecular complex. In FIG. 5A, an exemplary substrate is coated with streptavidin (SA). Two exemplary molecular complexes containing an analytical portion comprising at least one biotin moiety (b) are indirectly tethered to the substrate via biotin-avidin interactions. The molecular complexes in this example comprise identity portions comprising fluorescent reporter groups at six labeling positions, GGRBBR (relative to the biotin capture ligand). This exemplary molecular complex comprises a reaction portion (not shown) located between the biotin containing analytical portion and the identity portion. The identity portion comprises a coded molecular tag comprising a double-stranded DNA template with six reporter groups attached to labeling positions on the template using PNA and/or pcPNA openers (including at least one labeling position comprising a PNA opener or a pcPNA opener comprising the "R" reporter group, depicted as X in the enlarged schematic). As shown in FIG. 5B, when the bound molecular complex is subjected to an elongating force, such as a fluid flow or a field, the molecular complex is stretched in the direction of flow or field. Thus, in this exemplary molecular complex, the analytical portion serves both as a means for tethering the molecular complex to the substrate and also orients the identity portion, allowing the order of the reporter groups in the identity portion to be determined based on the biotin reference point.

Figure 5A:
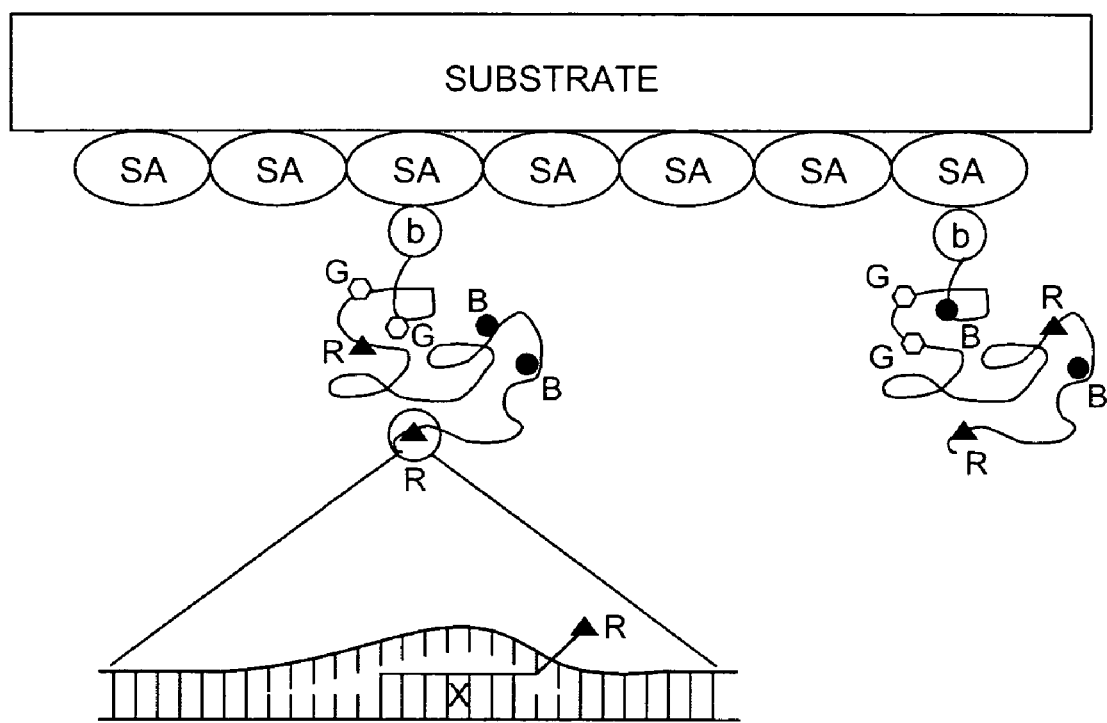
FIG. 5: depicts an illustrative method for detecting at least one molecular complex or at least part of a molecular complex.
Figure 5B:
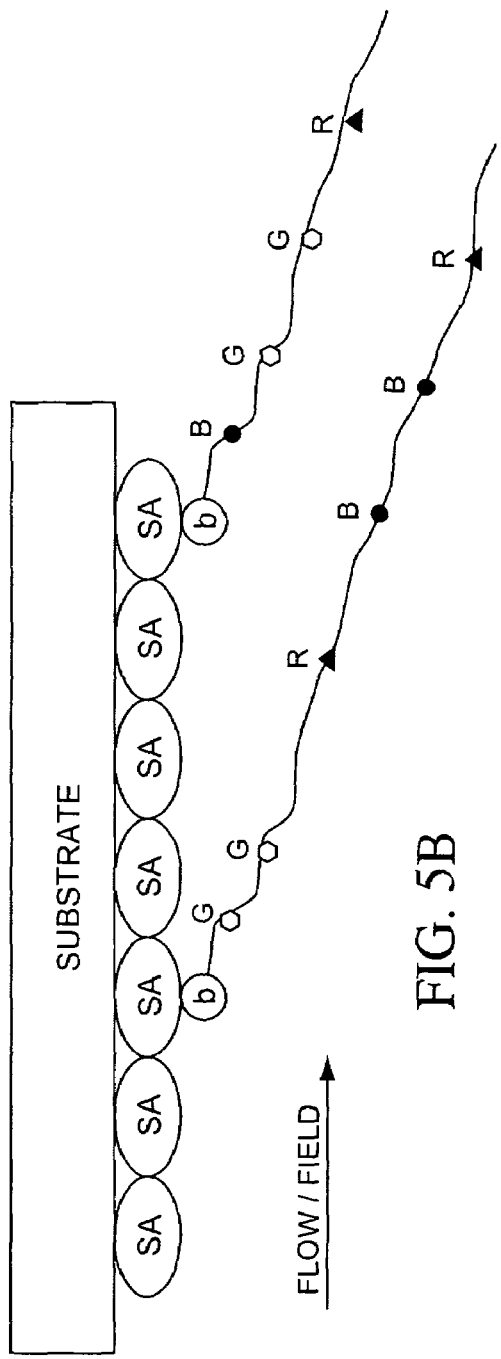
Figure 5C:
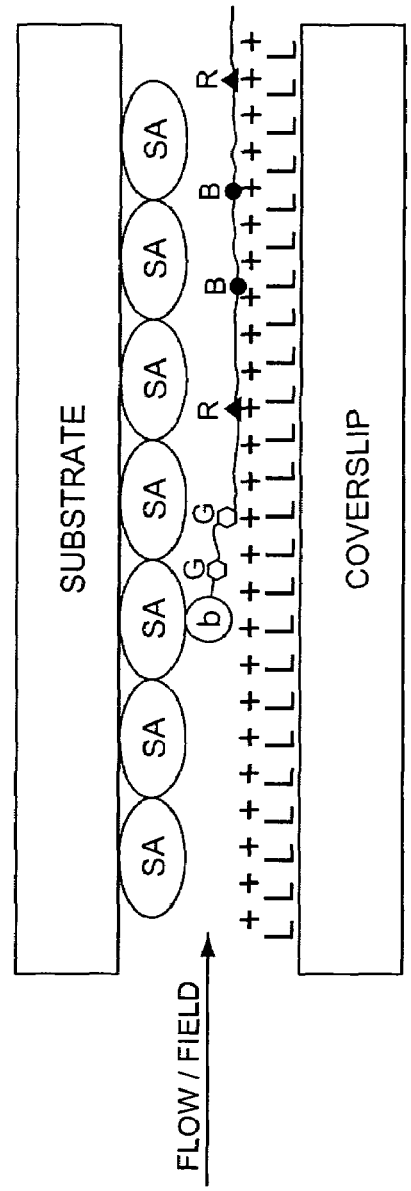

FIG. 5C depicts another exemplary embodiment of the analyte detection methods. Here, a cover slip is coated with poly-L-lysine (L), imparting a positive charge (+) to the surface of the cover slip. The molecular complex is tethered to the substrate, as before. The molecular complex is stretched due to an elongating or stretching force, shown as a fluid flow or field, the positively charged cover slip surface tends to interact with the elongated molecular complex at multiple attachment points along its length, attaching it to the cover slip and making it easier to determine the order of the reporter group species.

Figure 5D:
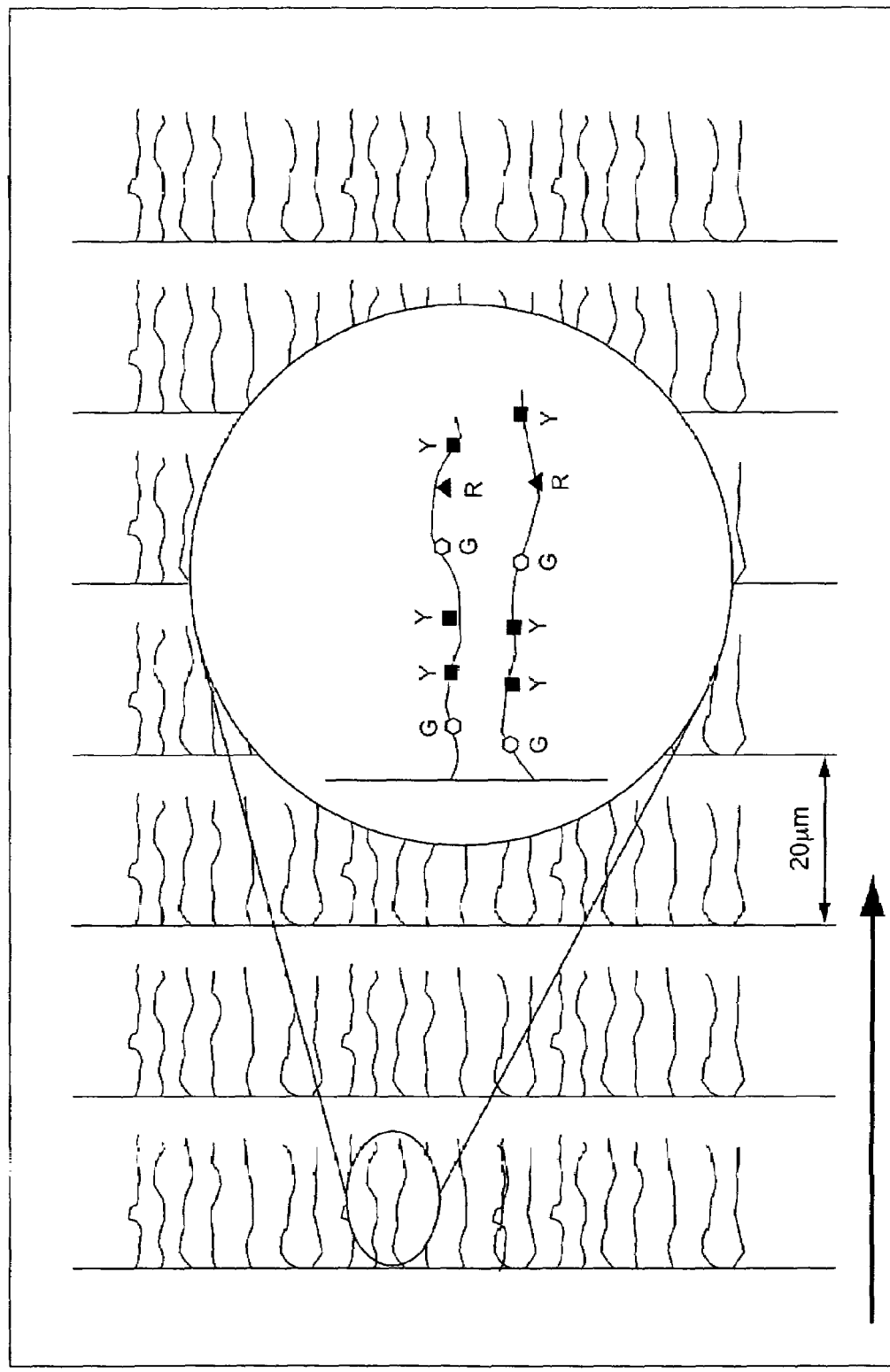

FIG. 5D depicts a patterned substrate comprising capture moieties in a series of parallel lines (for illustration purposes, top to bottom) with a spacing of approximately 20 µm (appropriate for elongating labeled λ DNA templates without overlap from one line tethered or attached molecular complex to the next). The skilled artisan understands that the distance between parallel lines on such a patterned substrate can vary depending on the molecular complex or at least part of molecular complex being individually detected. Each line of bound capture moieties is shown interacting with molecular complexes, or at least part of molecular complexes, comprising identity portions including coded molecular tags (see the blow up section depicting two identity portions comprising ordered reporter groups GYYGRY). The left to right arrow at the bottom indicates a fluid flow or field causing the indirectly bound molecular complexes or at least part of molecular complexes to elongate due to the flow or field. The tethered or attached molecular complexes or at least part of molecular complexes are individually detected using an appropriate SMD to determine the order of the reporter groups in each identity portion.

In certain embodiments, individually detecting comprises optical detection of at least one molecular complex in solution. In certain embodiments, solution phase optical detection comprises timed-gated fluorescence. In certain embodiments, optical detection comprises at least one electrophoresis capillary, including without limitation, microcapillaries and nanocapillaries; at least one sheath flow; at least one microfluidic device; or combinations thereof, wherein molecular complexes or at least parts of molecular complexes are individually detected and the order of the corresponding reporter group species is identified. In certain embodiments, individually detecting comprises detecting at least one molecular complex or at least part of a molecular complex in at least one microdroplet. In certain embodiments, at least one electrodynamic trap is used to levitate at least one microdrop comprising at least one molecular complex or at least part of a molecular complex. Detailed descriptions of SMD techniques for individually detecting at least one molecular complex or at least part of a molecular complex in solution can be found in, among other places, Single Molecule Detection in Solution: Methods and Applications, C. Zander, J. Enderlein, and R. Keller, eds., John Wiley & Sons, Inc. (2002); M. Barnes et al., Anal. Chem. 67:A418–23 (1995); M. Barnes et al., J. Opt. Soc. Am. B 11:1297–1304 (1994); S. Nie and R. Zare, Ann. Rev. Biophys. Biomol. Struct. 26:567–96 (1997); M. Foquet et al., Anal. Chem. 74:1415–22 (2002); S. Weiss, Science 283: 1676–83 (1999); C. -Y. Kung et al., Anal. Chem. 70:658–661 (1998); M. Wabuyele et al., Electrophoresis 22:3939–3948 (2001); W. Ambrose et al., Chem. Rev. 99:2929–56 (1999); P. Goodwin et al., Acc. Chem. Res. 29:607–13 (1996); and R. Keller et al., Anal. Chem. 74:316A–24A (2002).

The detection and decoding techniques used for solution phase fluorescence detection formats typically have similar fluorescence and spatial resolution concerns as bound, i.e., tethered or attached, fluorescence detection formats. In both formats, fluorescence, whether from an individual molecular complex or a cleavable component, is typically detected on detectors with appropriate optical filters or an imaging spectrograph. Orientation in bound detection formats is typically based on the tether or attachment points, but can be based on particular coding patterns, for example but not limited, a particular reporter group is always used in a specified labeling position and nowhere else.

Alignment of solution phase molecular complexes or parts of molecular complexes can be achieved by, for example but not limited to, flow along a capillary, between plates with a narrow gap, or through an appropriate microfluidic device. The flow stream can align the molecular complexes or parts of molecular complexes by, for example but not limited to, sheath flow, microfluidic channel structures, or by solvent polymer interactions. In certain embodiments, the flow velocity is designed to insure that a molecular complex or a part of a molecular complex spends a specified amount of time in the detection region, that only one molecular complex or cleavage component is present in the detection region at a given time, or both.

Orientation of solution phase molecular complexes or parts of molecular complexes for identifying the order of their corresponding reporter groups can be achieved using particular coding patterns, for example but not limited, a particular reporter group species is always used in a specified labeling position and nowhere else or a fixed, identifiable reporter group order at two or more specific labeling positions and varying reporter group species at one or more of the other labeling positions. Flow cells with single molecule channels can be used and individual molecular complexes or cleavable components can be forced into such channels for orientation during detection and decoding, using for example but not limited to, a multi-spectral analog detector or an imaging detector. In certain embodiments, multiple solution phase molecular complexes, parts of molecular complexes, or both, are passed through a wide channel and multi-spectral images are taken for analyzing and decoding the order of reporter group species of individually detected molecular complexes and/or parts of molecular complexes.

In certain embodiments, individually detecting comprises near field microscopy, including but not limited to near-field scanning optical microscopy; far-field microscopy, including but not limited to, far-field confocal microscopy and fluorescence-correlation spectroscopy; wide-field epi-illumination microscopy, evanescent wave excitation microscopy or total internal reflectance (TIR) microscopy; scanning confocal fluorescence microscopy; the multiparameter fluorescence detection (MFD) technique; two-photon excitation microscopy; or combinations thereof. In certain embodiments, individually detecting comprises fluorescence detection integrated with atomic-force microscopy, for example but not limited to, using an inverted optical microscope; or fluorescence excitation spectroscopy combined with shear-force microscopy. Detailed descriptions of such techniques can be found in, among other places, S. Nie and R. Zare, Ann. Rev. Biophys. Biomol. Struct. 26:567–96 (1997); R. Brown et al., Review of Single Molecule Detection in Biological Applications, NPL Report COAM 2, National Physics Laboratory, Middlesex, United Kingdom (2001)("Brown et al."); P. Rothwell et al., Proc. Natl. Acad. Sci. 100:1655–60 (2003); C. Eggeling et al., J. Biotechnol. 86:163–80 (2001); W. Ambrose et al., Chem. Rev. 99:2929–56 (1999); S. Weiss, Science 283:1676–83 (1999); G. Segers-Nolten et al., Nucl. Acid Res. 30:4720–27 (2002); and J. Michaelis et al., Nature 405:325–28 (2000).

In certain embodiments, individually detecting comprises scanning probe microscopy techniques, applied optical spectroscopy techniques, nanoelectromechanical (NEMS) techniques, or combinations thereof. In certain embodiments, individually detecting comprises at least one of the following SMD techniques: scanning tunneling microscopy; atomic force microscopy (AFM), including but not limited to cryo-AFM and single-walled carbon nanotube-AFM (SWNT-AFM); spectrally resolved fluorescence imaging microscopy (SFLIM); surface enhanced Raman spectroscopy (SERS); surface enhanced resonant Raman spectroscopy (SERRS); surface plasmon resonance (SPR); and scanning electrochemical microscopy (SECM). Detailed descriptions of such SMD techniques can be found in, among other places, Brown et al., and Woolley et al., Nat. Biotechnol. 18:760–63 (2000).

In certain embodiments, at least one molecular complex or at least a part of a molecular complex interacts with or becomes attached or tethered, directly or indirectly, to a substrate by one or more attachment points. In certain embodiments, at least one substrate comprises one or more surfaces to which a molecular complex or at least part of a molecular complex can interact, become attached or tethered, either directly or indirectly. For example, but not limited to, non-covalent attachment, such as by hybridization with at least one hybridization tag complement, capture moiety-capture ligand interaction, aptamer-target binding, electrostatic interaction, hydrophobic interaction, nonspecific adsorption, solvent evaporation, on or in a polymer such as a hydrogel, such as agarose, polyacrylamide, or the like; on or in a spin cast polymer coating, such as a polylmethylmethacrylate (PMMA) coat (e.g., M. Prummer et al., Anal. Chem. 72:443–47 (2000)); and the like. In certain embodiments, substrates are used to enhance individual detection of at least part of a molecular complex. For example but not limited to, tethering a molecular complex or at least part of a molecular complex in a fluid flow or electric or dielectric field to provide an orientation or reference point for determining the order of reporter group species.

Substrate surfaces are typically planar, but can comprise a wide variety of topographies, including without limitation, concave, convex, and combinations of topographies on the same surface. Substrates for optical detection are typically composed of materials that are preferably (i) optically transparent, (ii) minimally reflective, (iii) minimally absorptive, and (iv) low fluorescence. The skilled artisan will understand that if optical detection comprises visualization from the same side as the illumination, then the substrate may, but need not be optically transparent. Exemplary substrates can be composed of one or more of the following: glass, including but not limited to borosilicate glass; quartz, including but not limited to fused quartz; mica; plastics, including but not limited to polystyrene, polycarbonate, polymethacrylate (PMA), PMMA, polydimethylsiloxane (PDMS); silicon, including silica-containing materials; germanium; graphite; films, including but not limited to, gold film, silver film, aluminum film, diamond film; and the like. The skilled artisan will appreciate that the suitability of a particular substrate, including its topography and composition, typically depends at least in part on the detection technique to be employed.

In certain embodiments, the substrate is pretreated, including but not limited to activation and/or derivatization treatments. Substrates can be derivatized or activated, for example but not limited to treatment with polylysine and various silanes, such as trimethoxysilanes, aminosilanes, including but not limited to APTES, to produce among other things, amine surfaces or aldehyde surfaces. These derivatized surfaces allow various capture moieties to be attached or tethered to the substrate. In certain embodiments, capture moieties are dried or evaporated onto a substrate. In certain embodiments, oligonucleotide capture moieties comprising, for example but not limited to 3'-propanol-derivitized residues or 5'-disulfide modifications, are directly coupled to underivatized substrates. In certain embodiments, such oligonucleotides are functionalized at their 5' terminus with activated 1-O-mimethoxytrityl hexyl disulfide 1'-[(2-cyanoethyl)-(N,N-diisopropyl)]phosphoramidite (Rogers et al., Anal. Biochem. 266:23 et seq., (1999)). Such disulfide bridge linked capture moieties can be cleaved by reducing agents. In certain embodiments, a molecular complex or at least part of a molecular complex bound to a capture moiety comprising such disulfide bridges is released from a substrate under reducing conditions. Detailed descriptions of substrates, substrate activation methods, and the like, can be found in, among other places, Beaucage, Curr. Clin. Med.

8:1213–44 (2001); Diehl et al., Nucl. Acid Res. 29, No. 7 e38, pages 1–5 (2001); Microarray Analysis; DNA Microarrays A Practical Approach, M. Schena, ed., Oxford University Press (1999); R. Stears et al., Nature Medicine 9:140–145 (2003), including all Supplementary Tables and the Supplementary Note; and DNA Array Image Analysis Nuts & Bolts, G. Kamberova and S. Shah, eds., DNA Press, LLC (2002).

IV. Exemplary Embodiments

A. Coded Molecular Tag Fabrication

According to the teachings herein, coded molecular tags can be fabricated using a variety of methods, including without limitation, template-independent subunit assembly, template-dependent subunit assembly, and template-dependent subunit synthesis.

Figure 12A:
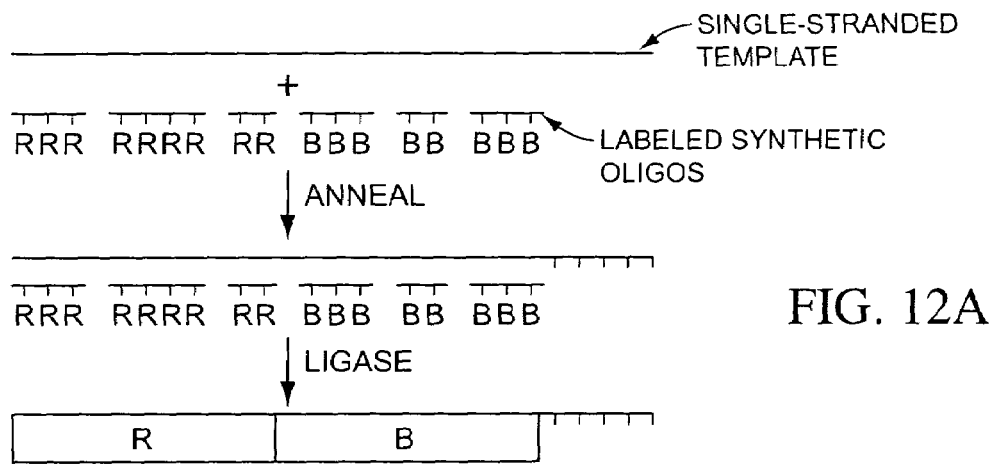
FIG. 12A depicts fabrication of an exemplary coded molecular tag comprising ordered reporter groups using synthetic subunits.
Figure 13:
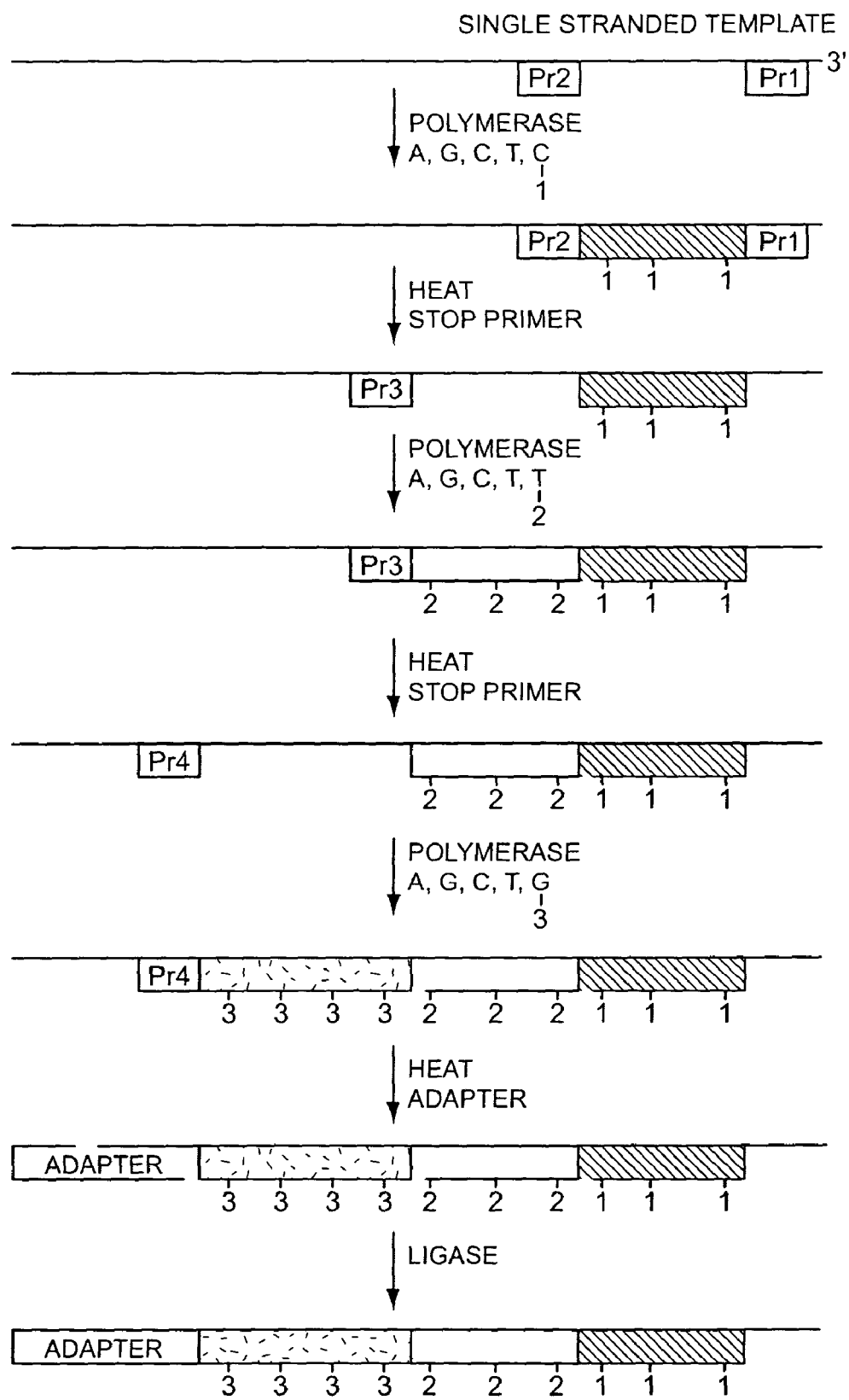
FIG. 13: depicts an exemplary coded molecular tag fabrication method using step-wise primer extension.

In certain embodiments, coded molecular tags are fabricated using a single-stranded nucleic acid template of known sequence and a series of reporter group-labeled oligonucleotides designed to anneal to complementary sites on the template. The labeled oligonucleotides are annealed to the template providing an ordered pattern of reporter groups, as shown in FIG. 12A. In certain embodiments, there are gaps between the labeled-oligonucleotides that are annealed to the template. In certain embodiments, coded molecular tag fabrication methods further comprise gap-filling primer extension, as shown in FIG. 13. In certain embodiments, methods for fabricating coded molecular tag comprise ligation. In certain embodiments, series of contiguous or nearly contiguous synthetic primers labeled with reporter group species hybridize contiguously to a single-stranded nucleic acid template. Additional primers labeled with a different reporter group species or a series of primers labeled with a different reporter group species can be hybridized either simultaneously or subsequently to the single-stranded template. In certain embodiments, such hybridized labeled primers are ligated together under appropriate conditions. In certain embodiments, at least one primer is extended by primer extension, then ligated, as shown in FIG. 13.

In certain embodiments, at least one coded molecular tag is fabricated using a stepwise primer extension process. As shown in FIG. 13, at least one primer pair comprising a start primer (shown as Pr1 in FIG. 13) and a stop primer (shown as Pr2 in FIG. 13) is hybridized with a single-stranded template to form a hybridization complex. In certain embodiments, the stop primer is non-extendable, i.e., it can not be extended by a polymerase in a primer extension reaction, e.g., it comprises a dideoxynucleotide on its 3' end. In the presence of an appropriate polymerase and under appropriate conditions, including at least one labeled nucleotide triphosphate, the start primer is extended to the vicinity of the stop primer by primer extension and at least one nucleotide comprising a reporter group (shown as C-1, T-2, and G-3 in FIG. 13) is incorporated in the newly synthesized section. In certain embodiments, the hybridization complex comprising at least one newly synthesized labeled section is heated to denature the stop primer. Additional primer pairs are hybridized to single-stranded regions of the template (shown as Pr3 and Pr4 in FIG. 13) and the process repeated as necessary to fabricate a semi-synthetic coded molecular tag comprising a multiplicity of synthesized subunits comprising reporter group species. The illustrative coded molecular tag shown in FIG. 13 further comprises an oligonucleotide adapter and a single-stranded overhanging 3' end. Such adaptors and overhanging ends are useful for, among other things, combining coded molecular tags and assembling probes.

In certain embodiments, the primers and synthesized sections of such coded molecular tags are ligated together. In certain embodiments, two or more primer pairs are hybridized to the same single-stranded template and the same reporter group species is incorporated into multiple labeling positions in parallel during the same primer extension reaction. In certain embodiments, coded molecular tags comprise at least one nucleotide adapter, for example but not limited to, an oligonucleotide linker.

In certain embodiments, coded molecular tags are fabricated using coded molecular tag subunits comprising at least two restriction fragments that are ligated together. In certain embodiments, the individual restriction fragments are labeled with reporter species using intercalating agents, as described in Example 2 (see also FIG. 7A or 7B). In certain embodiments, the restriction fragments are labeled using synthetic methods, for example without limitation, as described in Example 3. In certain embodiments, the restriction fragment are chemically-labeled, enzymatically-labeled, or both (see, e.g., Examples 3 and 4).

Coded molecular tags can be fabricated using coded molecular tag subunits, including without limitation, reporter group-labeled PCR plasmid DNA with engineered cohesive ends. In one exemplary embodiment, shown in FIG. 7B, two aliquots of this plasmid are PCR amplified separately, using different sets of forward and reverse primers with tails comprising restriction enzyme cleavage sites for PacI, or NotI, or PsiI (shown as arrows labeled "PacI", "NotI", or PsiI). The resulting linear double-stranded PCR amplicons each has either a PacI linker and a NotI linker at its ends, or a PsiI and a NotI linker at its ends. The amplicon on the left has the PacI linker on its left end and the NotI linker on its right end, while the amplicon on the right has the NotI linker on its left end and the PsiI linker on its right end. The amplicons are separately labeled using intercalating dyes, chemical-labeling, or enzymatic-labeling methods, forming coded molecular tag subunits. The two coded molecular tag subunits are cleaved using restriction enzymes Pac I and Not I for the coded subunit on the left, and using restriction enzymes PstI and Not I for the coded subunit on the right in order to form cohesive ends. Then the two coded molecular tag subunits are combined, annealed and ligated to form a coded molecular tag comprising two ordered reporter group species. The skilled artisan will understand that the directional ligation technique used here is helpful to limiting self-ligation during the fabrication of coded molecular tags.

In certain embodiments, coded molecular tags are fabricated using at least one synthetic subunit comprising at least one reporter group. As shown in FIG. 12A, a single stranded piece of nucleic acid of known sequence is used as a template. A series of contiguous oligonucleotides (oligos) are synthesized based on sequence of the template such that when hybridized with the template, essentially all of the template becomes double-stranded except for a short single stranded tail on one end. The synthetic oligos are labeled with reporter groups as follows: the first set of contiguous oligos comprise at least some incorporated nucleotides labeled with reporter group R; the second set of contiguous synthetic oligos comprise at least some incorporated nucleotides labeled with reporter group B. When each of these synthetic oligos are hybridized to the template, a double-stranded coded molecular tag is formed comprising reporter groups in the order RB. This illustrative coded molecular tag can be ligated together in the presence of an appropriate ligation agent. A gap-filling step may be employed prior to ligation if at least some of the labeled oligos are not contiguous.

The skilled artisan will understand that such nucleic acid-based coded molecular tag fabrication methods will work with essentially any nucleic acid template of appropriate length and with oligonucleotides of varying lengths, for example but not limited to, about 25 nucleotides long, about 30 nucleotides long, about 40 nucleotides long, about 45 nucleotides long, about 50 nucleotides long, about 60 nucleotides long, or even longer if their synthesis is feasible. If longer labeling positions are desired, additional contiguous oligonucleotides can be labeled with the appropriate reporter group or larger synthetic oligonucleotides can be used, or both. If spaces are desired between the labeling positions, unlabeled oligonucleotides of the desired length can be hybridized between the labeling positions.

Figure 12B:
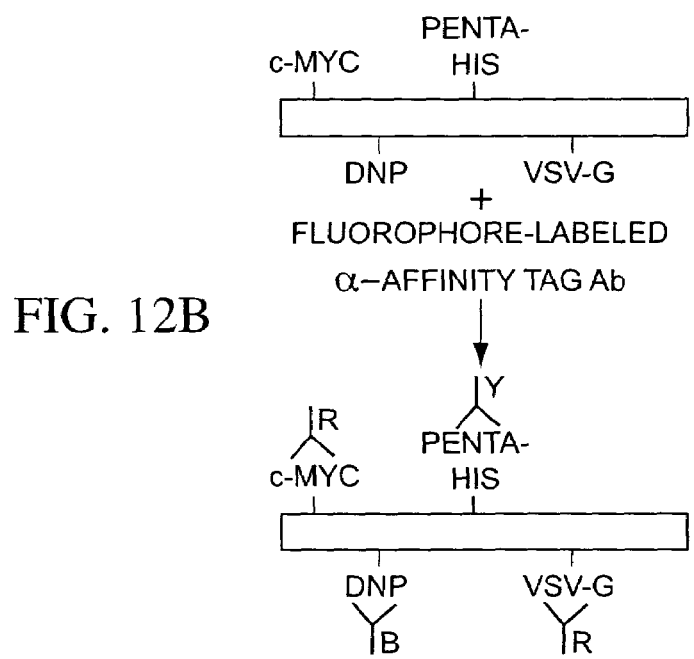
FIG. 12B depicts fluorophore-labeling an exemplary coded molecular tag comprising affinity tag reporter groups using appropriate fluorophore-labeled anti-affinity tag antibodies, as shown.

In certain embodiments, coded molecular tags are fabricated with ordered groups not comprising fluorophores, including without limitation, non-fluorophore affinity tags, as shown in FIG. 12B. Such probes can be subsequently labeled with fluorophores, if desired, using appropriate fluorophore-labeled anti-affinity tag antibodies, as shown in FIG. 12B. The skilled artisan will understand that the order of fluorescent reporter groups in such coded molecular tags is determined, in part, by the labeled antibodies being used. For example, to obtain the order fluorescein-rhodamine-Texas Red-Oregon Green using the coded molecular tag depicted in FIG. 12B, the following antibodies would be used: fluorescein-labeled anti-c-Myc antibody, rhodamine-labeled anti-DNP antibody, Texas Red-labeled anti-Penta-His antibody, and Oregon Green-labeled anti-VSV-G antibody.

Figure 12C:
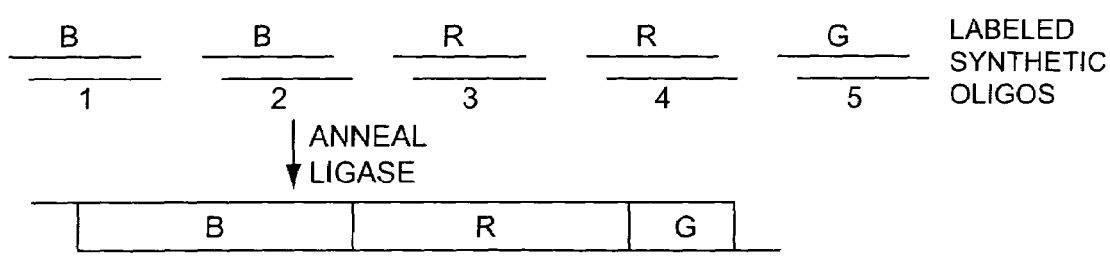
FIG. 12C depicts an exemplary coded molecular tag fabrication method comprising synthetic double-stranded coded molecular tag subunits.

In certain embodiments, coded molecular tags are fabricated using double-stranded reporter group-labeled synthetic oligonucleotides that are ligated together in a desired order. As shown in FIG. 12C, five coded molecular tag subunits (depicted as 1, 2, 3, 4, and 5 in FIG. 12C) are synthesized with appropriate cohesive ends. Subunits 1 and 2 comprise reporter group B, subunits 3 and 4 comprise reporter group R, and subunit 5 comprises reporter group G. When these subunits are combined, either collectively or in a step-wise manner, they will anneal provided that they possess appropriate cohesive ends forming a coded molecular tag. In the presence of an appropriate ligation agent, such as ligase, the annealed coded molecular tag subunits are ligated. These exemplary coded molecular tag subunits are designed so that their overhanging ends can serve cohesive ends for annealing desired oligonucleotides together. By annealing appropriately labeled synthetic oligonucleotides together, coded molecular tags comprising reporter group species in ordered patterns can be fabricated. Optionally, the annealed oligonucleotides can be ligated using a ligation agent. Such overhanging ends on these exemplary coded molecular tag subunits can also facilitate, among other things, annealing smaller coded molecular tags to generate larger coded molecular tags and probe assembly. The skilled artisan appreciates that overhanging ends can be located on the 5' end(s), the 3" end(s), or both and can be synthesized with any desired sequence.

In certain embodiments, coded molecular tags are fabricated using a single-stranded nucleic acid template comprising a sequence designed to allow incorporation of reporter-group labeled nucleotides only at specific locations. For example without limitation, a synthetic template comprising the artificial sequence GTTGT(T)$_n$TATTAT(T)$_n$TCTTCT(T)$_n$TGCTTAA (SEQ ID NO.: 1) is combined with a primer comprising the sequence TTAAGC, an appropriate polymerase, unlabeled dATP, and dCTP, dGTP, and dTTP, labeled with reporter groups 1, 2, and 3 respectively. Under appropriate conditions, a double-stranded nucleic acid coded molecular tag is generated by primer extension, wherein the nascent strand comprises the sequence TTMGCA(A)$_n$AG(2)AAG(2)A(A)$_n$AT(3)AAT(3)A(A)$_n$AC(1)AAC(1) (SEQ ID NO:2) with the ordered reporter group pattern 2-3-1. For optical detection methods, labeling positions are typically about 1 μm or more apart, or for nucleic acid coded molecular tags, about 3000 bases or more apart. Thus, in certain embodiments, (T)$_n$ and (A)$_n$ comprise about 3000 Ts or 3000 As, respectively; about 3500 Ts or As, respectively; about 4000 Ts or As, respectively; about 5000 Ts or As, respectively; or about 10000 Ts or As respectively.

The skilled artisan will appreciate that coded molecular tags can be can be mass-produced and stored for use as "off the shelf" interchangeable components for assembling probes for specific applications. In certain embodiments, templates and/or coded molecular tags further comprise one or more cleavable linker group; one or more restriction enzyme site and/or adapter sequence to facilitate, among other things, the assembly of probes; one or more affinity tag, aptamer sequence, or hybridization tag for separation and/or substrate attachment or tethering procedures; and combinations thereof. In certain embodiments, at least one reporter group is attached to at least one template with a PNA and/or pcPNA opener, clamp, earring structure, or the like (see, e.g., O. Zelphati et al., BioTechniques 28:304–16 (2000); Demidov et al., Methods 23:123–31 (2001); Izvolsky et al., Biochemistry 39:10908–13 (2000); Lohse et al., Proc. Natl. Acad. Sci. 96:11804–08 (1999); and Kuhn et al., J. Amer. Chem. Soc. 124:1097–1103 (2002)).

B. Probe Assembly.

Probes, according to the disclosed teachings, are molecules or assemblies that are designed to combine with at least one analyte, at least one analyte surrogate, or both, typically forming at least part of at least one molecular complex. Probes comprise at least one reaction portion that allows them to bind to or interact with at least one analyte, at least one part of at least one analyte, at least one analyte surrogate, at least part of an analyte surrogate, or combinations thereof, typically in a sequence-specific or confirmation-specific manner, for example but not limited to, nucleic acid hybridization, antigen-antibody binding, aptamer-target binding, and the like. The skilled artisan will understand that probes comprising at least one coded molecular tag can be assembled using a variety of methods known in the art, for example, without limitation, ligation techniques and crosslinking techniques (see, e.g., Example 9). Detailed descriptions of such procedures can be found in, among other places, Maniatis et al.; Sambrook et al.; Sambrook and Russell; Ausbel et al.; Bioconjugate Techniques; and The Electronic Protocol Book. In certain embodiments, at least one DNA coded molecular tag comprises at least one phosphorylated linker, at least one non-phosphorylated linker, at least one adapter, or combinations thereof (collectively, "adapters"; see, e.g., New England BioLabs 2002–03 Catalog & Technical Reference, particularly at pages 142–145, New England BioLabs, Inc., Beverly, Mass.; Stratagene 2003/2004 Catalog, particularly at page 211).

Figure 8A:
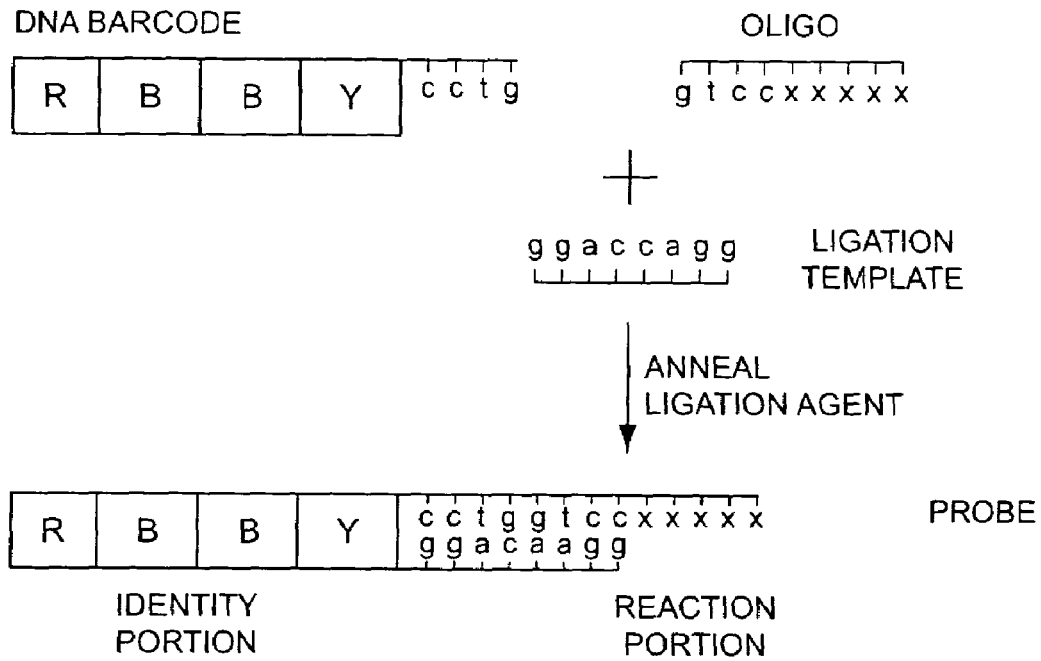
FIG. 8: depicts exemplary probe assembly methods using illustrative fabricated DNA coded molecular tags. The 13-mer oligonucleotide in FIG. 8A is shown in SEQ ID NO: 33.
Figure 8B:
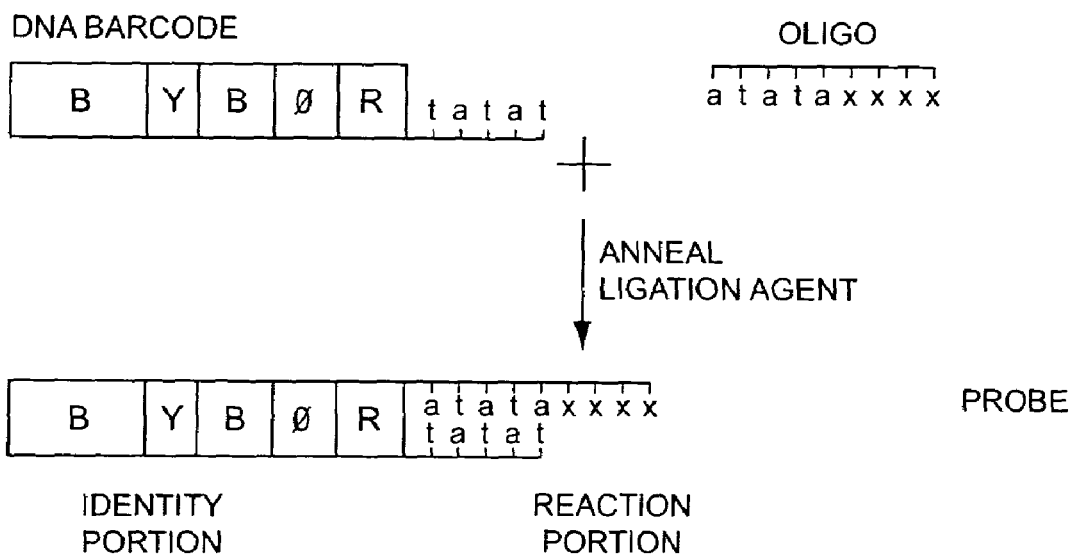

Exemplary probe assembly methods comprising ligation are shown schematically in FIG. 8. In FIG. 8A, a coded molecular tag comprising the ordered reporter group species RBBY and an illustrative single-stranded linker comprising the nucleotide sequence "cctg" is combined with an exemplary ligation template comprising the nucleotide sequence "ggaccagg" and a single-stranded oligonucleotide comprising the sequence "gtccxxxxx". These illustrative probe components are annealed and then ligated to generate a probe comprising an identity portion including a coded molecular tag and a reaction portion (shown as "xxxxx" in the probe; the sequence and/or length of the reaction portions varies, in part, due to the target sequences on the corresponding analyte or analyte surrogate). FIG. 8B depicts another exemplary probe assembly method, wherein a DNA coded molecular tag comprising ordered reporter groups BYBØR, where Ø represents a labeling site that is vacant, and a linker with the nucleotide sequence "tatat", is combined with an oligonucleotide comprising the sequence "atataxxxx" (shown as "OLIGO"). These illustrative probe components are annealed and ligated to generate a probe comprising an identity portion and a reaction portion (shown as the variable sequence "xxxx" in the probe).

In certain embodiments, probes of the invention are assembled using coded molecular tags. In certain embodiments, at least one coded molecular tag is incorporated in at least one identity portion. In certain embodiments, at least one first probe, at least one second probe, or at least one first probe and at least one second probe comprise at least one coded molecular tag. In certain embodiments, at least one coded molecular tag is coupled, either covalently or non-covalently, to an adapter such as a nucleotide linker sequence, as shown in FIG. 13, and as described in Example 3. In certain embodiments, the adapter facilitates the incorporation of at least one coded molecular tag (see, e.g., FIG. 8). In certain embodiments, at least one coded molecular tag comprises at least one capture ligand (see, e.g., FIG. 3, panel F). In certain embodiments, at least one coupled coded molecular tag-adapter comprises at least one capture ligand.

In certain embodiments, at least one adapter is located near or in the coded molecular tag so that it is: (i) at or near one end of the ordered reporter group species and/or (ii) near at least one capture ligand to facilitate attachment or tethering of at least one probe. In certain embodiments, cleavage at one or more restriction enzyme cleavage sites within an adapter generates blunt ends, releasing at least one cleavable component. In certain embodiments, cleavage at one or more restriction enzyme cleavage sites within an adapter generates cohesive ends that can facilitate annealing and ligation during coded molecular tag fabrication, probe assembly, or both, as shown in FIG. 7B.

In certain embodiments, probe assembly comprises ligating at least one coded molecular tag to at least one oligonucleotide comprising at least one reaction portion using an appropriate ligation template, such as the illustrative ligation template shown in FIG. 8A, to generate a exemplary probe comprising at least one reaction portion and an identity portion. The skilled artisan will appreciate that the ligation template may, but need not be, part of the probe. In other embodiments, a coded molecular tag is combined with an oligonucleotide comprising "cohesive ends", for example as shown in panel FIG. 8B. The two sequences can anneal under appropriate conditions, forming a probe, as shown in FIG. 8B. The annealed duplex can be ligated together, under appropriate conditions, using at least one ligation agent.

In certain embodiments, at least one probe comprising at least one identity portion forms a molecular complex with an analyte or an analyte surrogate in a multiplex reaction format. At least one molecular complex or at least part of a molecular complex is separated using, for example but not limited to, electrophoretic, chromatographic and/or affinity separation techniques. At least one separated molecular complex or at least part of a molecular complex is individually detected and the presence of the corresponding analyte is determined. In certain embodiments, at least one probe further comprises at least one cleavable component comprising at least part of an identity portion. In certain embodiments, at least one probe further comprises at least one cleavable crosslinker. In certain embodiments, cleavage of at least one crosslinker releases at least one cleavable component from at least one molecular complex or at least part of a molecular complex. The skilled artisan understands that a cleavable component is included within the term "part of a molecular complex."

In certain embodiments, at least one cleavable component comprising at least part of an identity portion further comprises at least one capture ligand (see, e.g., FIG. 4D). In certain embodiments, at least one cleavable component comprising at least one identity portion or at least part of an identity portion, further comprises at least one affinity tag, at least one aptamer, at least one hybridization tag, or combinations thereof. The skilled artisan will appreciate that in certain embodiments, the cleavable components containing at least part of a molecular complex are similar in concept to the cleavable isotope-coded affinity tags (ICAT; Applied Biosystems) used in some mass spectroscopy applications (see, e.g., Gygi et al., Nature Biotech. 17:994–44 (1999) and that mass spectral reporter groups are also within the scope of the invention.

Crosslinkers, typically join two or more molecules, by a covalent bond. Crosslinking reagents usually contain two reactive groups, for example but not limited to, succinimidyl esters, maleimides, and iodoacetamides, that may be the same (homobifunctional) or different (heterobifunctional). The reactive groups participate in covalent bond formation during chemical, thermal, or photo-activated reactions. Crosslinkers are referred to as cleavable or non-cleavable, dependent on their chemical composition and/or photolability. Cleavable crosslinkers can be cleaved into at least two parts, depending on their composition, when exposed to appropriate conditions and/or reagents for example but not limited to, cleavage of disulfides by reducing agents; cleavage of glycols and diols by periodates; diazo linkages cleaved by dithionate; ester linkages cleaved by hydroxylamine; sulfone linkages cleaved by bases; and the like. Crosslinking reagents, including cleavable crosslinkers, are available from several commercial sources, including Pierce Biotechnology, Inc., Rockford Ill.; and Molecular Probes, Inc., Eugene Oreg. Photocleavable compounds or photocleavable elements incorporated into at least one probe, at least one molecular complex, or both, are expressly within the intended scope of the invention. In certain embodiments, under appropriate photocleavage conditions at least one cleavable component is obtained from at least one molecular complex or at least part of a molecular complex. Detailed descriptions of crosslinkers and their use can be found in, among other places, Pierce 2003–2004 Applications Handbook & Catalog, Pierce Biotechnology, Inc. (2003)("Pierce Applications Handbook"); Handbook of Fluorescent Probes and Research Products, $9^{th}$ ed., Molecular Probes, Inc. (2002)("Molecular Probes Handbook"); DOUBLE AGENTS™ Cross-Linking Reagents Selection Guide, Pierce Chemical Co. (2001); Bioconjugate Techniques; S. Verma and F. Eckstein, Ann. Rev. Biochem. 67:99–134 (1997) and the Glen Research 2002 Catalog.

In certain embodiments, at least one probe set comprises at least one antibody molecule that reacts specifically with at least one analyte, at least one analyte surrogate, or both. In certain embodiments, at least one probe set comprises at least one aptamer that reacts specifically with at least one analyte, at least one analyte surrogate, or both. Certain embodiments of the compositions, methods, and kits further comprise at least one antibody molecule, at least one aptamer, or both, that specifically react with at least one first probe, at least one second probe, at least one molecular complex, at least part of a molecular complex, at least one capture moiety, at least one capture ligand, or combinations thereof.

C. Analyte Detection

1. Molecular Complex Formation.

In certain embodiments, one or more probe can hybridize with or bind to at least one analyte, at least one analyte surrogate, or combinations thereof, to form a molecular complex. In certain embodiments, at least one first reaction portion of at least one first probe and at least one second reaction portion of at least one corresponding second probe are designed to hybridize to complementary "target" sequences on the same strand of at least one analyte, at least one analyte surrogate, or combinations thereof. In certain embodiments, the probes in at least one probe set are suitable for ligating together when hybridized adjacent to one another (see, e.g., FIG. 1A, 1:1P1:2P1A). In certain embodiments, at least one first probe and at least one corresponding second probe are designed to hybridize to the same strand of at least one analyte or at least one reaction intermediate, at least one analyte surrogate, or both, but they do not hybridize adjacent to each other (see, e.g., FIG. 1A, 2:1P2:2P2B). In certain embodiments, the probes of at least one probe set are designed to hybridize to opposite strands of at least one analyte, at least one analyte surrogate, or both.

In certain embodiments, molecular complexes comprise at least one ligation product resulting from the ligation of at least one first probe and at least one corresponding second probe, as shown schematically in FIG. 1A. In certain embodiments, such ligation product molecular complexes further comprise at least one analytical portion (see FIGS. 1A and 3). In certain embodiments, the first probe and the second probe from the same probe set hybridized adjacent to each other. In certain embodiments, the first probe and the second probe do not hybridize adjacent to each other, but the 3' end of the 5' (upstream) probe is extended, under appropriate conditions and in the presence of at least one polymerase, until the extended 3' end of the upstream probe is adjacent to the downstream probe, sometimes referred to as "gap-filling" (see, e.g., FIG. 1A, 2:1P2:2P2B). In the presence of at least one ligation reagent and under appropriate conditions, at least one ligation product molecular complex is formed.

Figure 6B:
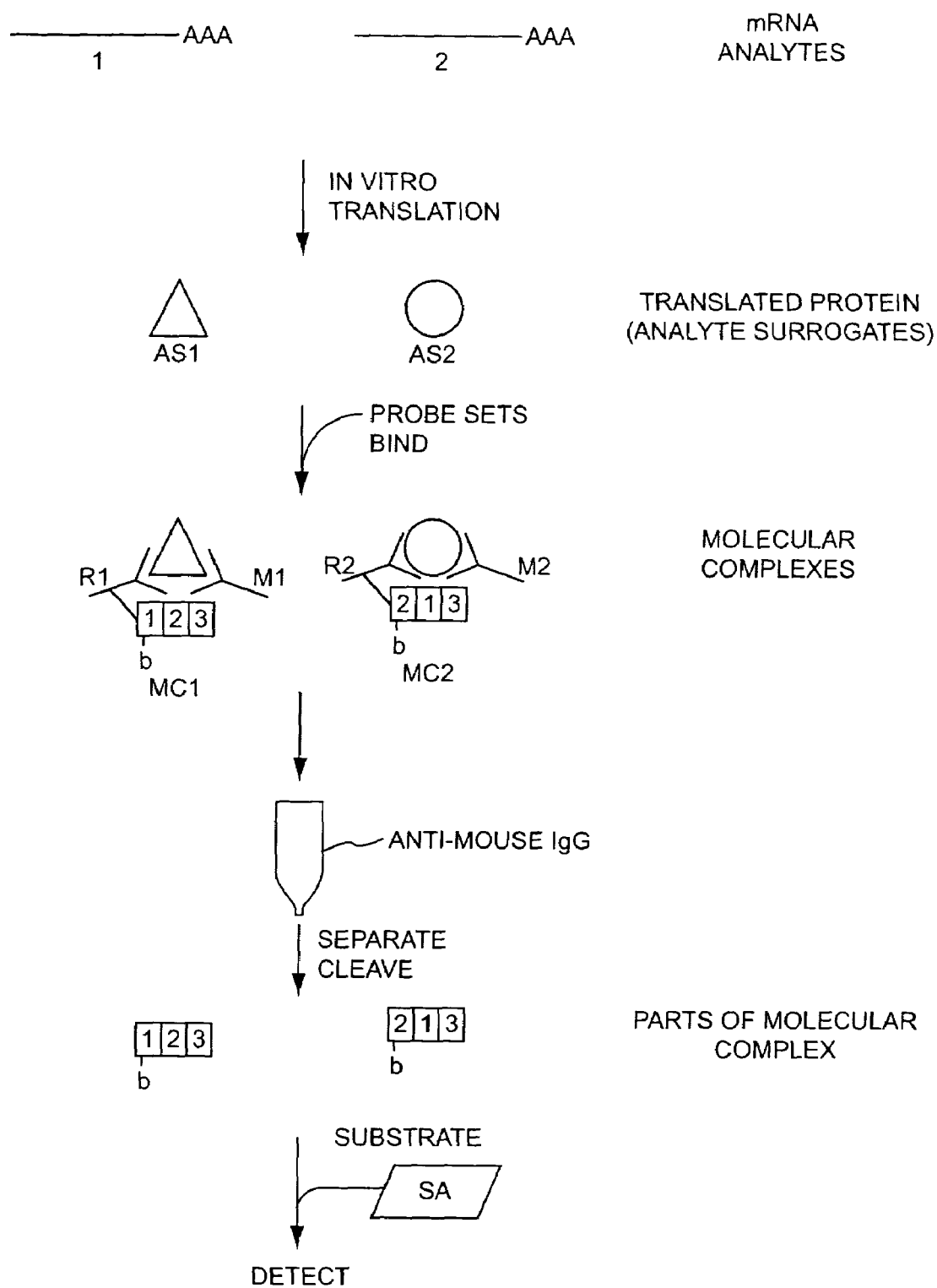

In certain embodiments, at least one molecular complex comprises at least one analyte surrogate, at least part of an analyte surrogate, at least one analytical portion, or combinations thereof (see, e.g., FIG. 6). In certain embodiments, at least one analyte surrogate comprises at least one nucleotide (see, e.g., FIG. 6A) or at least one amino acid (see, e.g., FIG. 6B).

Figure 1B:
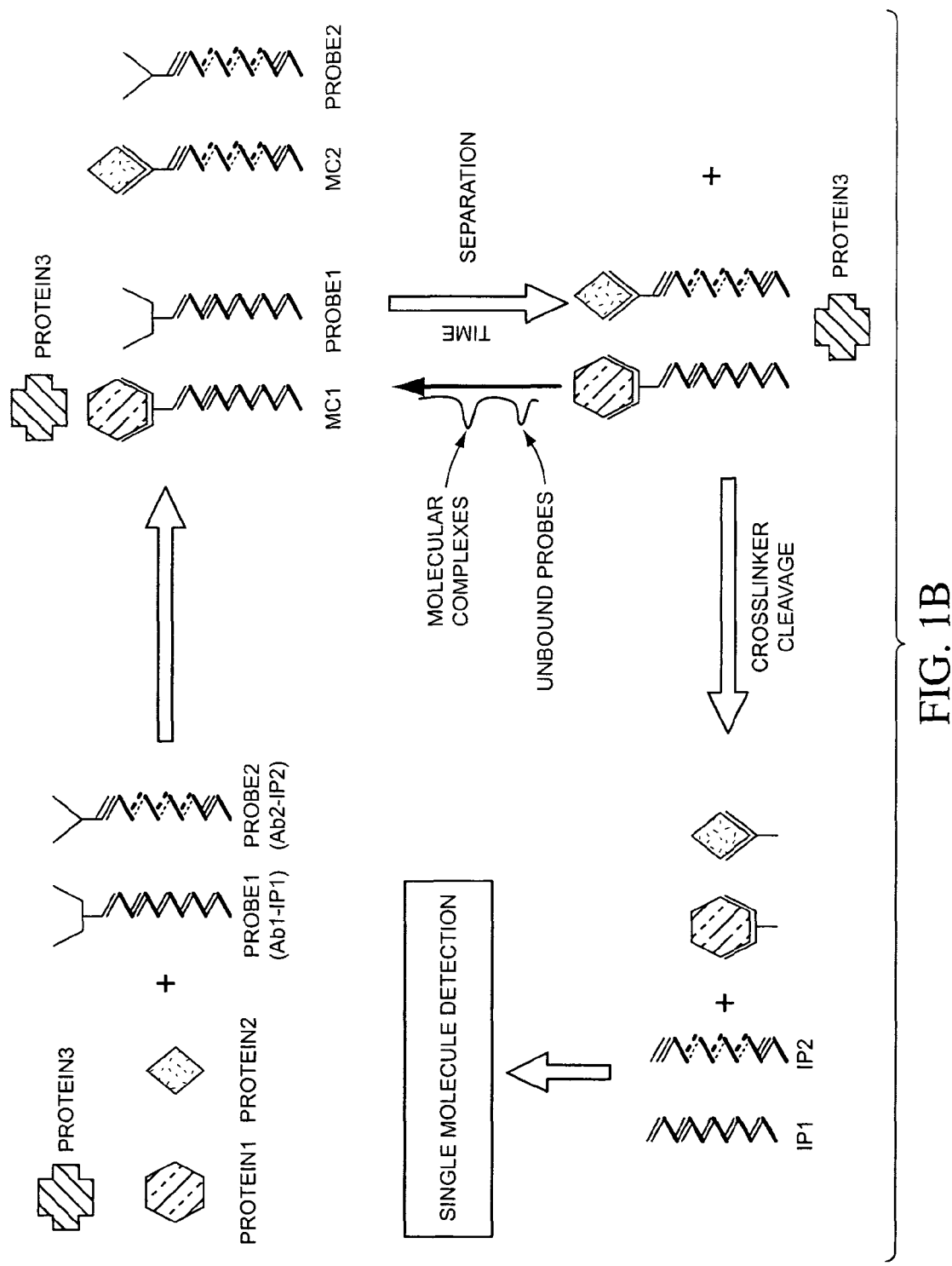
FIG. 1B depicts exemplary probes and methods for determining the presence of non-nucleic acid analytes.

In certain embodiments, at least one molecular complex comprises at least one probe and at least one analyte, wherein the at least one probe and the at least one corresponding analyte specifically interact but do not "hybridize" (see, e.g., FIG. 1B). For example but not limited to, an insulin molecule bound to at least one anti-insulin antibody comprising a coded molecular tag; a viral antigen such as hepatitis B surface antigen (HBsAg) and at least one anti-HBsAg antibody comprising a coded molecular tag; or the like. In certain embodiments such molecular complexes further comprises at least one analytical portion.

2. Nucleic Acid Analytes.

The disclosed compositions, methods, and kits can be used in a wide variety of applications to determine the presence of nucleic acid analytes in a sample. For example, the compositions, methods, and kits disclosed herein are useful for gene sequence analyses such as genotyping applications, including but not limited to sequence evaluation for SNP detection and identification; gene expression applications, including but not limited to mRNA expression profiling, splice variant analyses, and gene expression modification analyses, including but not limited to gene knock-down, gene knock-out, gene knock-in, gene up-regulation, gene down-regulation, and the like; ncRNA studies; mutation analyses including without limitation, evaluating heritable and somatic mutations; evaluating drug-resistant mutants in parasites, microorganisms, and viruses; and the like.

FIG. 1A depicts exemplary probes and methods for determining the presence of nucleic acid analytes. The upper panel of FIG. 1A depicts a sample comprising three molecular species, designated 1, 2, and 3, wherein species 1 and 2 represent analytes of interest. This sample is mixed with exemplary probe sets one and two, designed to determine the presence of analyte species 1 and 2. The probe set for molecular species 1 comprises three types of probes, a first probe (1P1) comprising a reaction portion and an identity portion comprising reporter groups R and G in the ordered sequence RGRG (left to right). The first probe set also comprises two species of second probe, designated 2P1A and 2P1B, each comprising a reaction portion and an analytical portion, but differing in the sequence of their respective reactive portions so that most frequently only one second probe fully hybridizes with complementary sequences of analyte 1 under appropriate reaction conditions. When properly annealed with analyte 1, the two probe species of probe set one hybridize adjacently (shown as 1:1P1:2P1A). The second probe set also comprises three probe species, one first probe (1P2), comprising an analytical portion, and two second probe species, designated 2P2A and 2P2B. Both of these second probes comprise an identity portion comprising reporter groups R and G, but positioned in different orders, so the order of 2P2A is RRRR, and the order for 2P2B is GGRG. When properly annealed with analyte 2, the two probe species are hybridized to the same strand of analyte 2 (shown schematically as 2:1P2:2P2B), but they are not hybridized adjacently due to a gap between the 5' end of the annealed second probe (here, 2P2B) and the 3' end of the first probe (shown schematically as 1P2). Under appropriate conditions, e.g., in the presence of at least one appropriate polymerase, nucleotide triphosphates, salts, and reaction conditions, the gap between the hybridized probes of the second probe set is closed by primer extension. In the presence of an appropriate ligation reagent and under suitable conditions, the annealed probes of both the first probe set and the second probe set are ligated together to form ligation product molecular complexes 1 and 2, respectively (shown hybridized to their corresponding analytes, 1:LPMC1 and 2:LPMC2). When denatured and separated from unbound probes, reaction components and sample material, the single-stranded ligation product molecular complexes (LPMC1 and LPMC2) are individually detected using at least one SMD. The order of the reporter groups is identified, indicating in this example that two species of analytes, i.e., 1 and 2, are present in the sample.

In certain embodiments, at least one analyte includes a nucleic acid sequence comprising at least one at least one deoxyribonucleotide, at least one ribonucleotide, or both at least one deoxyribonucleotide and at least one ribonucleotide. In certain embodiments at least one analyte comprises a double-stranded nucleic acid sequence comprising DNA or RNA, such as genomic DNA, including but not limited to fragments such as restriction enzyme fragments, shear fragments, or sonication-induced fragments. In certain embodiments, at least one analyte comprises at least one point mutation, at least one deletion, at least one insertion, at least one chromosomal translocation site, at least one splice junction, or combinations thereof.

In certain embodiments, at least one analyte comprises a nucleic acid molecule or a fragment thereof comprising at least one multi-allelic locus. In certain embodiments, one or more multi-allelic locus comprises at least one SNP. In certain embodiments, the disclosed compositions, methods, and kits allow one to determine which of two or more alternate sequences are present at a multi-allelic locus. In certain embodiments, a probe set comprises at least two different upstream probes, for example but not limited to, allele-specific oligos (ASOs), and one at least one downstream probe, for example but not limited to, a locus-specific oligonucleotide (LSO). In such probe sets, the at least two upstream probes differ by at least one nucleotide in their respective reaction portions.

For example but without limitation, when analyzing the nucleic acid from an individual that is homozygous for a particular bi-allelic SNP, in certain embodiments, the reaction portion of only one upstream probe of the probe set will fully hybridize with the target sequence, while the other upstream probe will have at least one nucleotide in it's reaction portion that is not hybridized. Thus, under appropriate conditions, a molecular complex comprising only a single species of corresponding ligation product will be formed, comprising the upstream probe with the fully complementary reaction portion ligated to the downstream probe, e.g., a LPMC. While two species of corresponding LPMCs will be formed, under appropriate conditions, when the nucleic acid sample is obtained from a heterozygous individual. In certain embodiments, a probe set comprises at least one upstream probe and at least two downstream probes. In such probe sets, the at least two downstream probes differ by at least one nucleotide in their respective reaction portions.

Figure 2:
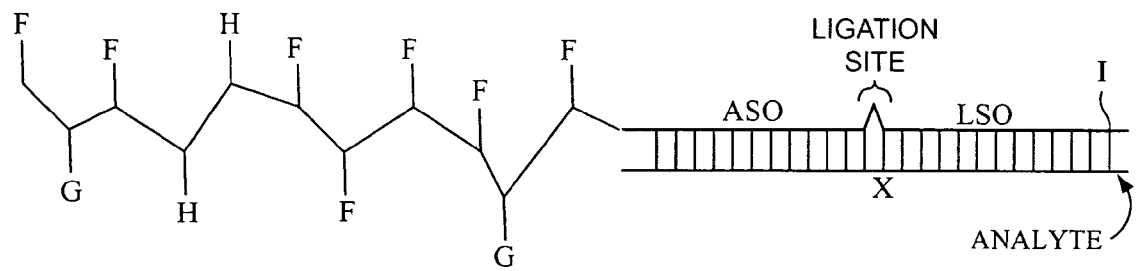
FIG. 2: schematically depicts an exemplary molecular complex for determining the presence of a nucleic acid analyte.

FIG. 2 schematically depicts an exemplary molecular complex for determining the presence of a nucleic acid analyte, for example but not limited to, a nucleic acid sequence containing a multi-allelic locus, such as a SNP site. The exemplary molecular complex comprises an analyte hybridized by its target sequence to the combined reaction portions of the ligation product. The exemplary ligation product molecular complex comprises both an identity portion and an analytical portion. The illustrative identity portion, comprises the ordered sequence of reporter groups "FGFHHFFFFGF" and a reaction portion are shown on the 5' probe ("ASO" in FIG. 2). The analytical portion comprising reporter group "I" and a reaction portion is shown on the 3' probe of the ligated probe set ("LSO" in FIG. 2). The letter "X" indicates the SNP site on the nucleic acid analyte and the ligation site is depicted by "Λ" in FIG. 2. The skilled artisan will understand that the identity portion can be located, at least partially, in either the first probe or the second probe of a given probe set and that the analytical portion can be located, at least partially, in either the first probe or the second probe of a given probe set, but typically, the entire identity portion and the entire analytical portion are not both located in the same probe of a given probe set.

In certain embodiments, at least one first probe and at least one corresponding second probe hybridize to sequences on the same strand of at least one analyte, at least one analyte surrogate, or both, but the first probe and the second probe are not hybridized adjacent to one another. In certain embodiments, at least one polymerase and at least one ligation reagent are provided. In certain embodiments, under appropriate conditions, at least one polymerase can extend a hybridized upstream probe by primer extension until the newly synthesized 3' end of the upstream probe is adjacent to the 5' end of the corresponding downstream probe. In certain embodiments, the newly synthesized 3' end of the upstream probe and the 5' end of the downstream probe are ligated together by at least one ligation agent to form a ligation product molecular complex.

In certain embodiments, at least one nucleic acid analyte is amplified to generate at least one analyte surrogate. In one exemplary embodiment, shown in FIG. 6A, messenger RNA (mRNA) analytes (shown schematically as W. L, and M; each comprising a "poly A" tail) are amplified using primer extension with sequence specific primers (depicted as Pr1 and Pr2) to generate single-stranded DNA analyte surrogates (depicted as ssDNA and W, L, or M but without poly A tails). Probe sets are added to the ssDNA analyte surrogates and at least some first probes and at least some corresponding second probes anneal with the corresponding analyte surrogates. The hybridized probe sets are ligated together in the presence of at least one ligation agent and under appropriate conditions, forming three species of LPMC in this illustrative embodiment, each comprising (i) an identity portion including a coded molecular tag and (ii) an analytical portion that includes at least one DNP moiety. The three exemplary LPMCs are placed on at least one substrate comprising a patterned array of anti-DNP antibody capture moieties so that the molecular complexes are tethered to the substrate via the interaction between the anti-DNP antibody capture moieties and the DNP capture ligands, as shown in FIG. 6A. The tethered molecular complexes are then individually detected using an appropriate SMD technique and the order of the reporter groups in each coded molecular tag is determined.

In another exemplary embodiment, shown in FIG. 6B, mRNA analytes are amplified, using in vitro translation, to generate translated analyte surrogates. These analyte surrogates are combined with probe sets, each comprising (i) specific polyclonal rabbit antibody comprising coded molecular tags containing a biotin capture ligand, wherein the coded molecular tag is attached to the antibody probe by a cleavable linker and (ii) corresponding mouse IgG monoclonal antibody probes; and molecular complexes form. The reaction mixture comprising molecular complexes is combined with a chromatography matrix comprising anti-mouse IgG antibodies and the unbound material is separated from the bound molecular complexes comprising mouse IgG monoclonal antibodies. The linker is cleaved and cleavable components, i.e., the biotinylated coded molecular tags are isolated. The isolated coded molecular tags are combined with a streptavidin-coated substrate and the coded molecular tags are tethered to the substrate via biotin-streptavidin binding. The tethered coded molecular tags are individually detected using an appropriate SMD technique and the order of the reporter groups is determined.

A variety of methods are available for obtaining nucleic acid sequences, such as genomic DNA, from biological samples that can be used with the disclosed compositions, methods, and kits. Exemplary nucleic acid isolation techniques include (1) organic extraction followed by ethanol precipitation, e.g., using a phenol/chloroform organic reagent (e.g., Ausbel et al., eds., *Current Protocols in Molecular Biology*, John Wiley & Sons, New York (1995, including supplements through June 2003), preferably using an automated DNA extractor, e.g., the Model 341 DNA Extractor available from Applied Biosystems (Foster City, Calif.); (2) stationary phase adsorption methods (e.g., Boom et al., U.S. Pat. No. 5,234,809; Walsh et al., BioTechniques 10(4): 506–513 (1991); and (3) salt-induced DNA precipitation methods (e.g., Miller et al., Nucl. Acids Res., 16(3): 9–10 (1988)), such precipitation methods being typically referred to as "salting-out" methods. In certain embodiments, wherein at least one analyte comprises nucleic acid sequences, the above isolation methods can further comprise an enzyme digestion step, e.g., digestion with at least one proteolytic enzyme; and/or exposure to at least one surfactant, such as at least one cationic detergent, at least one zwitterionic detergent, at least one anionic detergent, or combinations thereof (see, e.g., Greenberg et al., U.S. patent application Ser. Nos. 09/724,613 and U.S. patent application Ser. No. 2002/0177139). Commercially available kits can be used to expedite such methods, for example, Wizard® Genomic DNA Purification Kit and the RNAgents® Total RNA Isolation System (both available from Promega, Madison, Wis.). Further, such methods have been automated or semi-automated using, for example, the ABI PRISM™ 6700 Automated Nucleic Acid Workstation (Applied Biosystems, Foster City, Calif.) or the ABI PRISM™ 6100 Nucleic Acid PrepStation and associated protocols, e.g., NucPrep™ Chemistry: Isolation of Genomic DNA from Animal and Plant Tissue, Applied Biosystems Protocol 4333959 Rev. A (2002), Isolation of Total RNA from Cultured Cells, Applied Biosystems Protocol 4330254 Rev. A (2002); and ABI PRISM™ Cell Lysis Control Kit, Applied Biosystems Protocol 4316607 Rev. C (2001).

3. Non-Nucleic Acid Analytes.

The compositions, methods, and kits disclosed herein can also be used in a wide variety of applications to determine the presence of non-nucleic acid analytes in a sample. For example but without limitation, the compositions, methods, and kits are useful for, pharmacokinetic studies, including but not limited to, drug metabolism, ADME profiling, and toxicity studies; target validation for drug discovery; protein expression profiling; proteome analyses; metabolomic studies; post-translation modification studies, including but not limited to glycosylation, phosphorylation, acetylation, and amino acid modification, such as modification of glutamate to form gamma-carboxy glutamate and hydroxylation of proline to form hydroxylation; analyses of specific serum or mucosal antibody levels; evaluation of non-nucleic acid diagnostic indicators; foreign antigen detection; and the like.

In certain embodiments, at least one analyte comprises at least one amino acid, for example, a peptide or protein molecule; at least one carbohydrate subunit, e.g. (—CHO—); at least one peptide bond; at least one glycosidic bond; at least one fatty acid side chain; at least one alkyl group, allyl group, aryl group, and/or at least one aromatic ring structure; or combinations thereof. In certain embodiments, at least one probe set comprises only first probes or only second probes, but not both. In certain embodiments, at least one molecular complex comprises at least one probe comprising at least one identity portion, but no separate analytical portion, and the inherent properties of at least one molecular complex serves as the basis for separating at least one molecular complex, for example but not limited to, using capillary electrophoresis, gel filtration chromatography, HPLC, or the like (see, e.g., of FIG. 1B). In certain embodiments, at least one first probe or at least one second probe further comprises at least one cleavable component, at least one cleavable linker, or both.

In certain embodiment, at least one first probe, at least one second probe, or both the first probes and the second probes of at least one probe set comprise at least one antibody that reacts specifically with at least one analyte or at least one analyte surrogate. In certain embodiments, at least one first probe, at least one corresponding second probe, or at least one first probe and at least one corresponding second probe, comprises at least one aptamer that reacts specifically with at least one non-nucleic acid analyte or at least one analyte surrogate. In certain embodiments, at least one first probe, at least one second probe, or both the first probes and the second probes of at least one probe set comprise binding proteins that specifically interact with at least one analyte or at least one analyte surrogate.

The schematic in FIG. 1B depicts one exemplary embodiment comprising a sample that includes non-nucleic acid analytes. Non-nucleic acid molecules (shown as Protein 1, Protein 2, and Protein 3) and two single probe probe sets (shown as Probe 1 and Probe 2), each comprising an analyte-specific antibody molecule comprising an identity portion attached with a cleavable crosslinker located between the reaction portion and the identity portion (Ab1-IP1 and Ab2-IP2, respectively), are combined and molecular complexes form (shown as MC1 and MC1). No probe set corresponding to Protein 3 is used, thus no molecular complex comprising Protein 3 is formed. The molecular complexes are separated using, for example electrophoresis or chromatography, and the separated molecular complexes are treated with an appropriate reagent to cleave the crosslinker and release cleavable components, each comprising an identity portion (shown as IP1 and IP2). The cleavable components are individually detected using an appropriate SMD technique and the order of the reporter group species in the coded molecular tags is determined.

The skilled artisan understands that with antibody probes, the reactive portion typically comprises the antigen binding site and related residues of the antibody molecule; and the target sequences comprise that portion of the analyte that includes the epitope, whether such sequences are linear, conformational, or combinations thereof. The skilled artisan will appreciate that the molecular complexes and the at least part of the molecular complexes described herein can be individually detected while tethered or attached to a substrate or while in solution, depending on, among other things, the nature of the specific molecular complex or cleavable component and the SMD technique and detection apparatus employed.

Protein isolation techniques are also well known in the art and kits employing at least some of these techniques are commercially available. Protein isolation techniques typically employ one or more of the following: maceration and cell lysis, including physical, chemical and enzymatic methods; centrifugation; separations by molecular weight, such as size exclusion chromatography and preparative electrophoresis; selective precipitation, for example, salting-in and salting-out procedures; various chromatographic methods; and the like. Detailed descriptions of and relevant protocols for protein purification techniques can be found in, among other places, Marchak et al., Strategies for Protein Purification and Characterization: A Laboratory Course Manual, Cold Spring Harbor Press (1996); Essentials from Cells: A Laboratory Manual, D. Spector and R. Goldman, eds., Cold Spring Harbor Press (2003); R. Simpson, Proteins and Proteomics: A Laboratory Manual, Cold Spring Harbor Press (2003); and D. Liebler, Introduction to Proteomics, Humana Press (2002). Commercially available kits can also be used, for example but not limited to, ProteoExtract™ Partial Proteome Extraction Kits (P-PEK) and ProteoExtract™ Complete Proteome Extraction Kits (C-PEK), available from CALBIOCHEM®, La Jolla, Calif. The skilled artisan will appreciate that non-nucleic acid analytes for use with the inventive compositions, methods, and kits can be readily obtained without undue experimentation using such purification techniques and commercial kits.

Expressly beyond the scope of the methods for determining the presence of at least one analyte disclosed herein, are various polymer sequencing techniques, for example but not limited to, DNA sequencing and protein sequencing; and restriction enzyme mapping techniques. Such techniques include, without limitation, cleaving identifiable subunits from one or more polymer and detecting the cleaved subunits to determine the sequence of the polymer, e.g., Edman degradation and similar techniques; moving, relative to each other, (a) at least one polymer comprising identifiable subunits and (b)(i) at least one activation or excitation source and (ii) at least one detector, to determine the sequence and/or structure of the polymer, and similar techniques; and cleaving identifiable fragments from at least one DNA sequence using one or more restriction enzymes and measuring the size or length of the restriction fragment and/or the shortened DNA polymer to generate a restriction map for the DNA, and similar techniques.

The invention, having been described above, may be better understood by reference to examples. The following examples are intended for illustration purposes only, and should not be construed as limiting the scope of the invention in any way.

EXAMPLE 1

Coded Molecular Tag Fabrication: Labeling Templates Using PNA Openers Comprising Reporter Groups Six different PNA openers comprising at least one fluorescent reporter group species ("FRG" in this example) are synthesized on an AB433A Peptide Synthesizer (Applied Biosystems, Foster City, Calif.) essentially according to the manufacturer's instructions and known methods. Each of the six PNA openers comprise the sequence: FRG-OO-Lys-Lys-[core sequence 1]-OOO-[core sequence 2]-Lys-Lys, where O refers to 8-amino-3,6-dioxaoctanoicacid linker, Lys refers to lysine, J refers to N-[2-aminoethyl-5-ylacetyl]isocytosine glycine, core sequence 1 refers to the particular single-stranded DNA sequence that is complementary to a specific sequence on the full-length bacteriophage lambda genome ("λ-DNA" in this example), and core sequence 2 depends on the sequence of core sequence 1, as shown. Table 1 shows the number of the illustrative PNA openers ("#"), the location of target sequence in λ-DNA ("Position"), the λ-DNA target sequence ("L-DNA Sequence"), the corresponding first core sequence ("Core Sequence 1"), the corresponding second core sequence ("Core Sequence 2"), and the Sequence ID Number (SEQ ID NO.:) for the corresponding L-DNA Sequence, Core Sequence 1, and the Core Sequence 2, respectively.

TABLE 1

| # | Position | L-DNA Sequence | Core Sequence 1 | Core Sequence 2 | SEQ ID NO.: |
|---|---|---|---|---|---|
| 1 | 105 | GAAAAGAAAG | CTTTCTTTTC | JTTTTJTTTJ | 3, 4, 5 |
| 2 | 4404 | AGAGGAGGAG | CTCCTCCTCT | TJTJJTJJTJ | 6, 7, 8 |
| 3 | 8141 | AAAGGAAAGG | CCTTTCCTTT | TTTJJTTTJJ | 9, 10, 11 |
| 4 | 12460 | GGGAAGAGAG | CTCTCTTCCC | JJJTTJTJTJ | 12, 13, 14 |
| 5 | 20727 | AGAAAGGGGA | TCCCCTTTCT | TJTTTJJJJT | 15, 16, 17 |
| 6 | 25025 | AGGAAGAAAA | TTTTCTTCCT | TJJTTJTTTT | 18, 19, 20 |

For simplicity, the FRGs are designated 1–6 to correspond to the PNA opener number. Thus, FRG-labeled PNA opener #1 comprises the sequence: FRG1-OO-Lys-Lys-CTTTCTTTTC-OOO-JTTTTJTTTJ-Lys-Lys.

Two µg lambda DNA is digested with BstEII in 20 µL reaction buffer. Each of the six FRG-labeled PNA openers (2–5 µM) are combined with the BstEII digested λ-DNA (0.1 µg/µL) in 10 µM NaHPO$_4$, pH 6.8 and incubated for at least two hours at 37°–60° C. Following the incubation, the fabricated coded molecular tags comprising a six-labeling position λ-DNA template with the ordered FRG pattern of 123456 are isolated and stored for use as an "off-the-shelf" reagent for assembling analyte detection probes. Alternatively, the reporter group-labeled PNA openers can be synthesized and stored for later use as "off-the-shelf" reagents.

The skilled artisan will appreciate that if, for example but without limitation, position 105 is always labeled with the same reporter group and that reporter group is not used in any other labeling position, the position 105 reporter group can serve as an orientation point for individually detecting such coded molecular tags in solution. The skilled artisan understands that λ-DNA comprises many additional labeling positions that could be used with corresponding PNA or pcPNA openers. Additionally, PNA or pcPNA openers that have multiple binding sites can be used to label multiple labeling sites if desired. The skilled artisan also understands that, while six exemplary PNA openers and a λ-DNA template were used for illustration purposes in this example, coded molecular tags can be fabricated from a variety of templates and any of a number of template-specific PNA openers and/or template-specific pcPNA openers. Further, the PNA and/or pcPNA components of such coded molecular tags can comprise a number of appropriate binding configurations, including without limitation, openers, clamps, and earring structures.

EXAMPLE 2

Coded Molecular Tag Fabrication: Restriction-Ligation Procedure

Figure 7A:
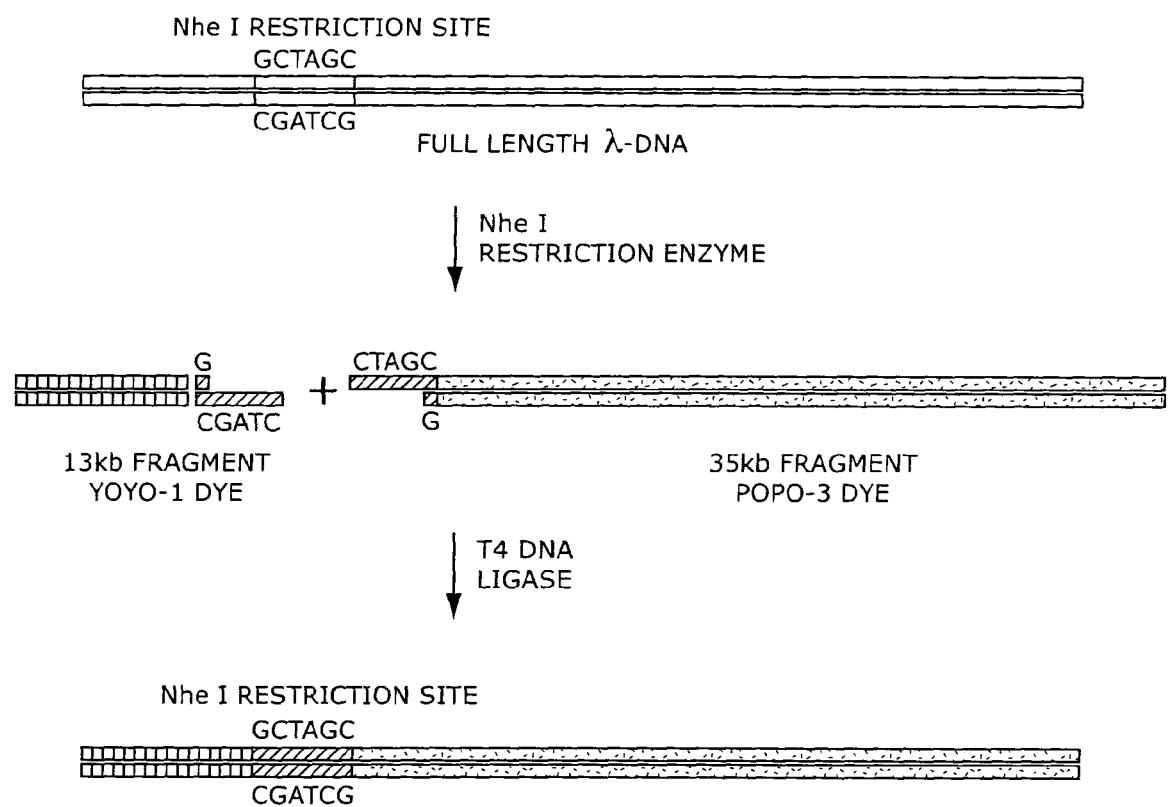
FIG. 7A schematically illustrates the fabrication of a two color coded molecular tag using coded molecular tag subunits comprising bacteriophage lambda genomic DNA restriction fragments, as described in Example 2.
Figure 7B:
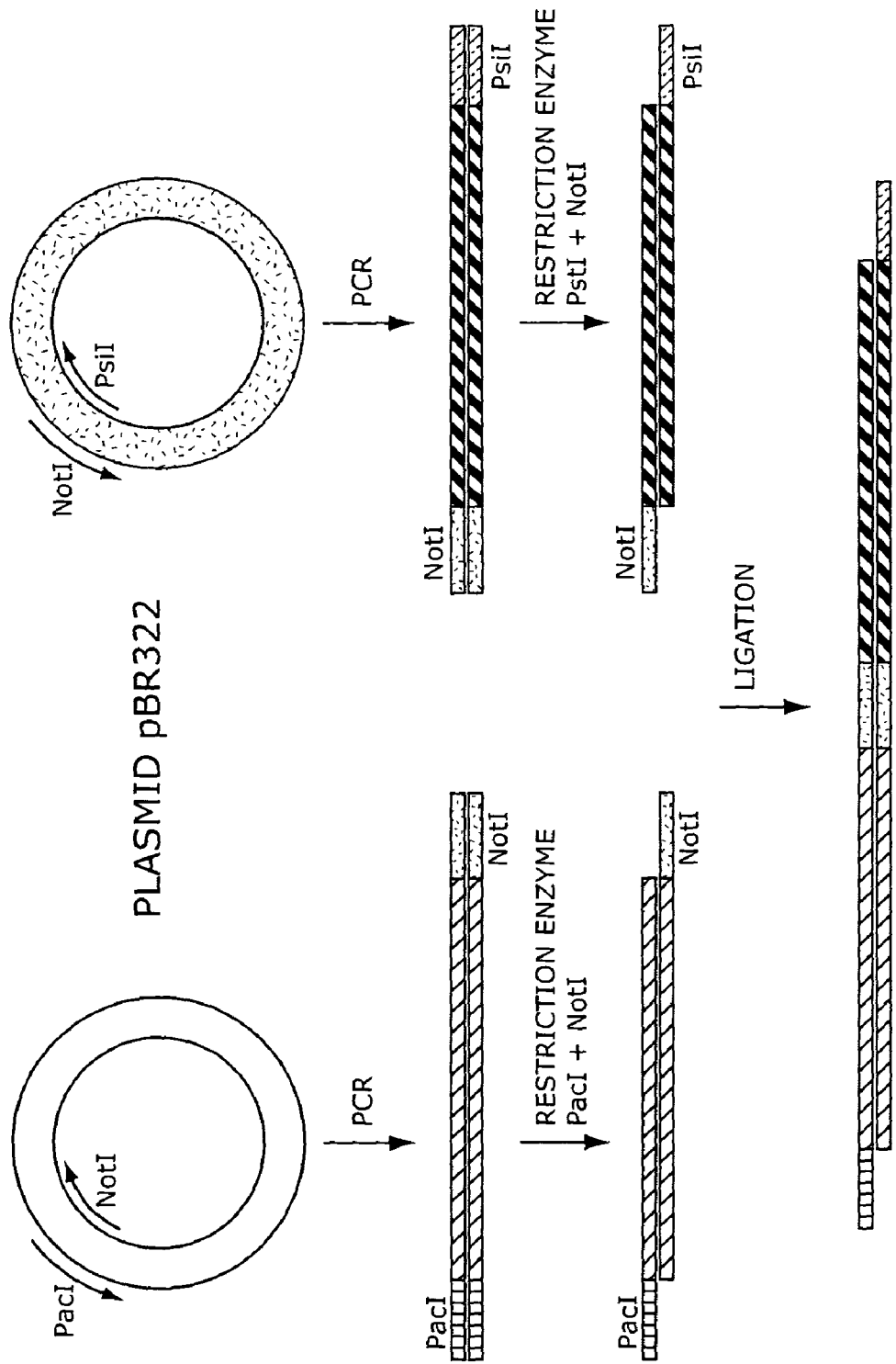
FIG. 7B depicts the generation of a coded molecular tag using coded molecular tag subunits comprising PCR amplicons of plasmid pBR322.

Coded molecular tags were generated by recombinant techniques using templates comprising genomic DNA from the bacteriophage lambda (λ-DNA) and two intercalating fluorescent dyes, as shown in FIG. 7A.

One microgram λ-DNA was combined with 10 units of the restriction enzyme NheI, bovine serum albumin (BSA) and 1×NEBuffer 2 in a reaction volume of 20 μL and incubated at 37° C. for one hour (NheI Restriction Endonuclease Kit, New England BioLabs, Beverly, Mass.). The restriction enzyme digest was loaded onto a 0.7% agarose gel in 1×TBE and electrophoresed at 1.5–2 volts/cm for 8 hours. Full-length (undigested) λ-DNA and a DNA ladder were electrophoresed in parallel as markers. The gel was then stained with the intercalating dye SybrGreen (Molecular Probes, Eugene, Oreg.) and the stained material visualized under UV illumination. Full-length λ-DNA is a double stranded molecule approximately 48,500 base pairs (48.5 kilobase pairs (kb)) long. NheI-digested λ-DNA produced two restriction fragments, a smaller fragment of approximately 13 kb and a larger, 35 kb fragment. The bands containing the two restriction fragments were excised from the gel and the fragments purified using a QIAEX II Gel Extraction kit according to the manufacturer's protocol (Qiagen, Inc., Valencia, Calif.). The purified 13 kb and 35 kb fragments were stained for 1 hour in 1:10000 dilutions of the intercalating dyes YOYO-1 or POPO-3, respectively (Molecular Probes, Inc.). These labeled coded molecular tag subunits were spin column purified, then ligated together using T4 DNA ligase according to the manufacturer's protocol (New England BioLabs). Such coded molecular tags can be individually detected using appropriate SMD techniques, for example but not limited to, laser-confocal microscopy.

The skilled artisan will also understand that different coded molecular tags can be generated using the illustrative restriction fragments described above, but labeled with different intercalating dyes, or labeled in the opposite or a different order, i.e., the 13 kb fragment labeled with POPO-3 and the 35 kb fragment labeled with YOYO-1. The skilled artisan will appreciate that different restriction fragments can be generated using appropriate restriction enzymes and/or different starting materials without undue experimentation, using conventional methodology known in the art, for example without limitation, PCR amplified plasmids, as shown in FIG. 7B.

EXAMPLE 3

Coded Molecular Tag Fabrication

Adenovirus-2 DNA (35.9 kb) is cleaved with Pac I (New England BioLabs #R0547) according to the manufacturer's instructions and the digestion products are gel purified using conventional methods. A 28.6 kb fragment and a 7.3 kb fragment ("frag 1" in this example) are obtained. The 28.6 kb fragment is cleaved with AsiS I (New England BioLabs #R0360) according to the manufacturer's instructions and the digestion products are gel purified using conventional methods. A 21.4 kb fragment and a 7.2 kb fragment ("frag 2" in this example) are obtained. The 21.4 kb fragment is cleaved with Pme I (New England Biolabs #R0560) according to the manufacturer's instructions and the digestion products are gel purified using conventional methods. A 13.2 kb fragment and an 8.2 kb fragment ("frag 3" in this example) are obtained. The 13.2 kb fragment is cleaved with Sbf I (New England Biolabs #V0101) according to the manufacturer's instructions and the digestion products are gel purified using conventional methods. An 8.4 kb fragment ("frag 4" in this example) and a 4.7 kb fragment are obtained. The four isolated restriction enzyme fragments are individually enzymatically-labeled with Pacific Blue (frag 1), Oregon Green 488 (frag 2), Alexa Fluor 568 (frag 3), and Alexa Fluor 660 (frag 4) using the ARES DNA Labeling Kits (Molecular Probes) and purified fluorophore labeled DNA fragments obtained. The labeled fragments are annealed, then ligated using the Quick Ligation™ kit (New England Biolabs #M2200S) to give a 31.2 kb coded molecular tag comprising the ordered reporter group sequence: Pacific Blue-Oregon Green 488-Alexa Fluor 568-Alexa Fluor 660.

An oligonucleotide linker with the sequence:

```
     GGCCGG  . . . -3'
 ACGTCCGGCC  . . . -5'    (SEQ ID NO.: 21)
``` is synthesized using conventional phosphoramidite chemistry except that instead of thymidine phosphoramidite, 5'-Dimethoxytrityloxy-5-[N-((4-t-butylbenzoyl)-biotinyl)-aminohexyl]-3-acrylimido]-2'-deoxyUridine-3'-[(2-cyano-ethyl)-(N,N-diisopropyl)]-phosphoramidite (Biotin dT, Glen Research Cat. No. 10-1038-xx, Sterling, Va.) is used. The resulting oligonucleotide comprises a biotin moiety, a cohesive end that is compatible with an Sbf I cleavage site, an Hpa II restriction site, and an Hae III restriction site. Cleavage with Hpa II will result in a 2 base pair (bp) cohesive end, while cleavage with Hae III causes blunt ends.

This synthetic oligonucleotide is annealed with the 31.2 kb coded molecular tag, then ligated using the Quick Ligation™ kit. The resulting 31.2 kb coded molecular tag-linker ligation product is purified using conventional methods and stored for further use. When the 31.2 kb coded molecular tag-linker ligation product is treated with Hpa II (New England Biolabs #R0171), the sequence:

```
    CGG  . . . -3'
      C  . . . -5'
``` is removed from the linker portion of the ligation product, leaving a 2 base pair (bp) overhang. Thus, an oligonucleotide comprising a reaction portion and the sequence "CG" at its 5' end can anneal with the cleaved 31.2 kb-oligo ligation product and under appropriate conditions, the oligonucleotide can be ligated with the cleaved 31.2 kb coded molecular tag-linker ligation product to assemble a probe comprising a reaction portion, a biotin moiety, and a coded molecular tag. This probe also comprises an Hae III restriction site between the biotin moiety and the reaction portion.

The skilled artisan will appreciate that if this exemplary probe is cleaved with the restriction enzyme Hae III under appropriate conditions, a cleavable component comprising a coded molecular tag and a biotin moiety will be released. The skilled artisan will also understand that when combined with a substrate comprising avidin, streptavidin, or derivatives thereof, the cleavable component will become attached or tethered to the substrate via the biotin-avidin (i.e., capture ligand-capture moiety) interaction. The tethered or attached cleavable component can be individually detected using an appropriate SMD technique, for example but not limited to, laser-confocal microscopy, and the coded molecular tag can be decoded, i.e., the order of the reporter groups in the coded molecular tag are determined.

The skilled artisan will appreciate that the size and/or sequence of the linker oligonucleotide can vary and that any desired restriction enzyme site can be incorporated, although typically not a cleavage site that is present in the coded molecular tag. The linker can be synthesized or prepared enzymatically and may or may not comprise at least one affinity tag that may or may not be cleavable (see, e.g., Soukop et al., Bioconjug. Chem. 6:135–38 (1995); L. Klevan and G. Gebeyehu, Methods of Enzymol. 184:561–77 (1990); Bioconjugate Techniques; M. Shimkus et al., Proc. Natl. Acad. Sci. 82:2593–97 (1985); and K. Misiura et al., Nucl. Acids Res. 18:4345–54 (1990)). The skilled artisan will also appreciate that the probe and the coded molecular tag sequence can be enzymatically attached or be crosslinked, for example but not limited to using cleavable or non-cleavable chemical or photoaffinity crosslinking agents.

EXAMPLE 4

Coded Molecular Tag Fabrication: Chemical Labeling of Restriction Fragments

Lambda genomic DNA is cleaved with the restriction enzyme NheI and the 35 and 14 kb fragments gel purified and isolated as described in Example 2. The 14 kb fragment is placed in a microfuge tube (tube 1) on ice. The 35 kb fragment is digested with the restriction enzyme XbaI according to the manufacturer's protocol (New England Biolabs) and XbaI restriction fragments of 24.5 and 10.2 kb are gel purified and isolated as described in Example 2. The 10.2 kb fragment is placed in a microfuge tube (tube 2) on ice and the 24.5 kb fragment is digested with the restriction enzyme BsiWI according to the manufacturer's protocol (New England Biolabs) and BsiWI restriction fragments of 5.2 and 19.3 kb are gel purified and isolated as described in Example 2. The 5.2 kb fragment is placed in a microfuge tube (tube 3) on ice and the 19.3 kb fragment is digested with the restriction enzyme BsaI according to the manufacturer's protocol (New England Biolabs). The 7.9 and 11.4 kb BsaI restriction fragments are gel purified and isolated as described in Example 2. The 7.9 and 11.4 kb fragment are placed in separate microfuge tubes (tube 4 and tube 5, respectively) on ice.

The isolated restriction fragments are chemically-labeled using ULYSIS Nucleic Acid Labeling Kits (Molecular Probes) according to the manufacturer's protocol, except that the DNase I digestion step is omitted. For example, tubes 1 and 4 are separately labeled using the ULYSIS kit with Pacific Blue fluorophores (catalog no. U-21658); tubes 2 and 5 are separately labeled using the ULYSIS kit with Alexa Fluor 546 fluorophores (catalog no. U-21652) and tube 3 is labeled using the ULYSIS kit with Alexa Fluor 647 fluorophores (catalog no. U-21660).

The coded molecular tag subunits are relegated to form a coded molecular tag using the Quick Ligation™ Kit from New England Biolabs. The coded molecular tag subunits in tube 5 are ligated to the labeled restriction fragments in tube 4, and a 19.3 kb coded molecular tag is gel purified and isolated. This 19.3 ligation product is ligated to the labeled restriction fragments in tube 3, and a 24.5 kb coded molecular tag is gel purified and isolated. This 24.5 kb coded molecular tag is ligated to the coded molecular tag subunits in tube 2, and a 34.7 kb coded molecular tag is gel purified and isolated. This 34.7 kb coded molecular tag is ligated to the coded molecular tag subunits in tube 1, and a coded molecular tag of approximately 48 kb is gel purified and isolated. Alternatively, all of the coded molecular tag subunits can be combined and ligated in a single ligation step to generate a 48 kb coded molecular tag. This 48 kb coded molecular tag, corresponding to full length λ genomic DNA with the order Pacific Blue-Alexa Fluor 546-Alexa Fluor 647-Pacific Blue-Alexa Fluor 546 can be used for probe assembly.

This coded molecular tag can be detected using, for example, a scanning laser confocal microscope system, including a Nichia direct diode laser (~405 nm), a double YAG (yttrium, aluminum, garnet) laser (~555 nm), and a helium-neon laser (~632 nm) in a single beam laser confocal configuration. Alternatively, a xenon arc lamp, filtered into three favorable excitation lines, can be used as the illumination source to provide a suitable fluorescent image for individual detection. The skilled artisan understands that a wide variety of illumination sources can provide an acceptable fluorescent image and thus any suitable detection method is within the scope of the invention.

The skilled artisan will appreciate that any two coded molecular tag subunits can be used as coded molecular tags, not just the 48 kb coded molecular tag; that the order of labels can be varied; that a variety of different reporter groups can used in fabricating coded molecular tags, for example, there are at least ten ULYSIS nucleic acid labeling kits, each with a different fluorophore; that coded molecular tags can be fabricated using a wide variety of templates; and that one or more appropriate adapter (e.g., oligonucleotide linker) can be added to one or more ends of the coded molecular tag to facilitate probe assembly, e.g., for use as one or more interchangeable component in assembling the probes disclosed herein.

EXAMPLE 5

Analysis of a Multi-allelic Locus: Amplification and SNP Detection

One form of hypercholesterolemia, referred to as familial hypercholesterolemia (FH), results from a SNP, identified as mutation "W23X" (131 G->A). To evaluate susceptibility to FH, one can be determine whether the "wild-type" or mutant form of the FH allele is present at the W23X SNP site.

Genomic DNA is obtained from a patient and, if desired, the gDNA can be PCR amplified using 5' synthetic oligonucleotide primers with the sequence: ATAGACACAG-GAAA (SEQ ID NO.: 22) and 3' synthetic oligonucleotide primers with the sequence: GGGGAAACCCGTAC-TATACG (SEQ ID NO.: 23) using conventional methods known in the art. The analytes or amplicon analyte surrogates comprising the SNP sequence(s) of interest ("Amplicons" in this example) are combined with at least one corresponding probe set.

The probe set comprises two species of upstream probe, referred to as ASO1 and ASO2 in this example, and one species of downstream probe, referred to as LSO in this example. ASO1 is designed with a reaction portion comprising the sequence GCATCTCCTACAAGTG (SEQ ID NO.:24) and is labeled at its 5' end with digoxigenin (DIG). ASO2 is designed with a reaction portion comprising the sequence GCATCTCCTACMGTA (SEQ ID NO.:25) and is labeled at its 5' end with 2,4-dinitrophenyl (DNP). ASO1 and ASO2 probe species are synthesized on an ABI 3900 High-Throughput DNA Synthesizer (Applied Biosystems, Foster City, Calif.) according to conventional methods. ASO1 is end-labeled using an aminolinker phosphoramidite and then DIG-labeled using the DIG Oligonucleotide 5'-End Labeling Set (Roche Diagnostics GmbH Cat. No. 1 480 863, Mannheim, Germany), essentially as described in the manufacturer's instructions. ASO2 is 5' end-labeled with DNP-TEG phosphoramidite (Glen Research Cat. No. 10-1985–95) essentially as described in the manufacturer's instructions and methods known in the art. The corresponding LSO probe species comprises the sequence GGTCTGC-GATGGATGGCC (SEQ ID NO.:26), wherein the first 12 nucleotides on the 5' end form the reaction portion, and the last four nucleotides on the 3' end can hybridize with an appropriate Apa I restriction fragment ("Oligo 5" in this example), and an identity portion.

The identity portion, comprising a nucleic acid coded molecular tag on a T7 bacteriophage template with an adapter, a commercially available Apa I linker (New England BioLabs Cat. #S1129S), ligated to the end comprising the first (5'-most) base on the left end (see, e.g., T7 restriction map, New England BioLabs 2002–2003 Catalog at page 320), is prepared. The coded molecular tag comprises fluorescent reporter groups in the order Alexa Fluor 488, Alexa Fluor 568, Alexa Fluor 488, and Alexa Fluor 647, left to right. These identity portions are cleaved with Apa I according to the manufacturer's instructions (New England BioLabs, Cat. #RO114S), then annealed with and ligated to copies of Oligo 5 under appropriate conditions to assemble probes of the exemplary probe set.

The three probe species of this exemplary probe set are combined with the Amplicons and annealed, forming molecular complexes. Appropriate upstream probes are ligated to the downstream probes using the Quick Ligation Kit (New England BioLabs) essentially as described in the manufacturer's instructions, forming ligation product molecular complexes. The reaction mixture, comprising the ligation product molecular complexes, is heated and the ligated products are isolated and combined with a substrate comprising a patterned surface including evenly-spaced alternating lines of covalently bound, commercially available anti-DNP or anti-DIG antibody capture moieties (e.g., Bethyl Laboratories, Montgomery, Tex.; United States Biological, Swampscott, Mass.; ZYMED Laboratories, So. San Francisco, Calif.; Roche Diagnostics GmbH, Penzberg, Germany). The alternating lines are typically spaced far enough apart that elongated molecular complexes do not overlap from one line to the next, e.g., approximately 20 µm for full length λ-DNA. The anti-DIG antibody capture moieties react immunospecifically with ligation products comprising ASO1, while the anti-DNP antibody capture moieties react immunospecifically with ligation products comprising ASO2, indirectly binding the corresponding ligation products to the substrate. The bound ligation products are elongated in a fluid flow and individually detected using laser confocal microscopy. Detection of the ordered reporter group Alexa Fluor 488-Alexa Fluor 568-Alexa Fluor 488-Alexa Fluor 647 at a location corresponding to a line of anti-DIG antibody capture moieties indicates that the patient's gDNA comprises the "wild-type" sequence and is not susceptible to familial hypercholesterolemia. Detection of the ordered reporter group Alexa Fluor 488-Alexa Fluor 568-Alexa Fluor 488-Alexa Fluor 647 at a location corresponding to a line of anti-DNP antibody capture moieties indicates that the patient's gDNA comprises the W23X mutation and the patient is susceptible to FH. Detection of the ordered reporter group Alexa Fluor 488-Alexa Fluor 568-Alexa Fluor 488-Alexa Fluor 647 at both the anti-Dig and anti-DNP locations indicates that the patient is heterozygous with respect to this multiallelic locus.

The skilled artisan will appreciate that any number of multiallelic loci with known SNP sequences can be evaluated using the compositions, methods, and kits described herein. The skilled artisan will also appreciate that many different types of capture ligands, corresponding capture moieties, substrates, and identity portions can be employed with the disclosed compositions, methods, and kits and that the location of capture ligands and identity portions can vary while keeping within the scope of the teachings herein.

EXAMPLE 6 p53 Mutation Analyses

A number of mutations in tumor suppressor genes, such as p53, have been identified in numerous human cancers (see, e.g., Ahrendt et al., Proc. Natl. Acad. Sci. USA 96:7382–87, 1996; de Cremoux et al., J. Natl. Cancer Inst. 91:641–43, 1999; Anderson et al., Radiat. Res. 154:473–76, 2000; Kurose et al., Nature Genetics, 32:355–57, (2002); and Ohiro et al., Mol. Cell. Biol. 23:322–334, 2003). For example, but not limited to, the wild type sequence for p53 as well as many known p53 mutations are publicly available from numerous sources, such as the National Center for Biotechnology Information (NCBI) "Entrez" web site (ncbi.nlm.nih.gov/Entrez), Japanese Patent No. JP 1998127300-A/6, and sunsite.unc.edu/dnam/mainpage (Cariello et al., Nucl. Acid Res. 24:119–20, 1996).

Genomic DNA is isolated from a whole blood sample obtained from a breast cancer patient using conventional methods and/or commercially available kits. The genomic DNA is combined with probe sets selected to identify the presence or absence of three known p53 mutations observed in medullary breast carcinoma, occurring at exon 7 codon 236 ("236"; TAC->TGC), exon 7 codon 248 ("248"; CGG->CAG), and exon 7 codon 252 ("252"; deletion of codon 252 CTC)(see, e.g., P. deCremoux et al., J. Natl. Canc. Inst. 91:641–43 (1999)). The 236 probe set comprises two first probes with a 3' sequences ending in " . . . CMCTA" (236-1-1) and "CAACTG" (236-1-2) and a second probe comprising the sequence "CATGT . . . " at the 5' end (236-2). The 248 probe set comprises a first probe comprising the sequence " . . . AACCG" at the 3' end (248-1) and two second probes comprising the sequences "GGAGG . . . " (248-2-1) and "AGAGG . . . " (248-2-2) at their respective 5' ends. The 252 probe set comprises a first probe comprising the sequence " . . . CTCAC" at its 5" end (252-1) and a second probe comprising the sequence " . . . CCCAT" at its 3' end (252-2). In this illustrative example, the breast cancer patient carries the 236 point mutation, but not the 248 point mutation or the 252 deletion mutation.

The respective probes hybridize with the patient's genomic DNA under appropriate conditions and molecular complexes form. Taq ligase is added and under appropriate conditions, ligation product molecular complexes comprising 236-1-1:236-2, 248-1:248-2-1, and 252-1:252-2 form. Each ligation product molecular complex further comprises at least one affinity portion comprising at least DNP capture ligand and at least one identity portion including a unique DNA coded molecular tag comprising fluorescent reporter group species.

The ligation product molecular complexes are denatured and separated by capillary electrophoresis. The molecular complexes are placed on a microscope slide substrate coated with commercially available anti-DNP antibody capture moieties and incubated at room temperature to allow antibody binding. The substrate is washed to remove unbound components, then illuminated using a laser of appropriate excitation wavelength. The fluorescent reporter groups in the coded molecular tags are individually detected using confocal microscopy with appropriate lasers, filters, etc. The order of reporter groups in each of the three coded molecular tags is identified and the presence of the p53 wild-type sequence at codon 248, the wild-type sequence at codon 252 and the mutant sequence at codon 237 is determined.

The skilled artisan understands that using the compositions, methods, and kits disclosed herein, heritable and somatic mutations can be analyzed in single assay or multiplex reaction formats. The skilled artisan will appreciate that appropriate experimental conditions depend in part on the sequence of the probes being employed and the ligation agent, but that such reaction conditions are generally available or can be calculated or experimentally determined without undue experimentation using ordinary skill and techniques known in the art. The skilled artisan will also understand that amplification methods, including but not limited to PCR or primer extension, can be employed to amplify low copy number nucleic acid analytes.

EXAMPLE 7

Nucleic Acid Amplification-Protein Detection

In one exemplary embodiment, mRNA analytes in a sample are amplified by in vitro translation, using a commercially available rabbit reticulocyte lysate in vitro translation kit. As shown in FIG. 6B, mRNA analytes designated "1" and "2", are amplified by in vitro translation to produce analyte surrogates 1 and 2 ("AS1" and "AS2"). The two analyte surrogates are combined with the corresponding probe sets. At least one first probe of each corresponding probe set comprises a rabbit polyclonal antibody specific for its corresponding antigen ("R1" and "R2"), a DNA coded molecular tag comprising reporter groups 1, 2, and 3, at least one biotin capture ligand within the coded molecular tag, and a cleavable linker located between the antibody molecule and the identity portion. At least one second probe of each corresponding probe set comprises a mouse IgG monoclonal antibody specific for its corresponding antigen ("M1" and "M2"). The skilled artisan will appreciate that the antibodies for each probe set are selected so that they bind to different, non-interfering, epitopes of the analyte or analyte surrogate than the corresponding antibody.

The molecular complexes that form by the binding of the two antibody probes, are passed over a anti-mouse IgG sepharose column that specifically binds the second probes, separating the column bound molecular complexes. The bound molecular complexes are washed using appropriate buffer and the linker cleaved using an appropriate reagent to release cleavable components. These cleavable components, comprising ordered fluorescent reporter groups and at least one biotin capture ligand at its proximal end, are collected and combined with a substrate comprising patterned streptavidin capture moieties ("SA"). The cleavable components become indirectly tethered to the substrate by the binding of at least one biotin capture ligand to at least one substrate-bound streptavidin capture moiety. Due to the location of the at least one capture ligand within the coded molecular tag, the identity portions are tethered to the substrate at the proximal end of the coded molecular tag, i.e., the end of the coded molecular tag that was closest to the cleavable linker of the intact first probe. Thus, when placed in an external field, such as a fluid flow or an electric field, the coded molecular tag attachment point serves to orient the bar code, as shown in FIG. 5D. The substrate is illuminated with laser light of appropriate excitation wavelength and the coded molecular tags are individually detected using confocal microscopy. The order of the fluorescent reporter groups in each coded molecular tag is identified, shown as 123 and 213 in FIG. 6B, which correspond to mRNA analytes 1 and 2 respectively. The skilled artisan will understand that a variety of antibodies can be used in the methods of the invention, including without limitation, polyclonal, monospecific, monoclonal, engineered, chimeric, humanized, FAb fragments, scFv fragments, and the like.

EXAMPLE 8

Foreign Antigen Detection

In certain embodiments, at least one analyte comprises at least one foreign antigen, such the surface antigen of hepatitis B virus (HBsAg). There are four known subtypes of HBsAg, designated "adw", "adr", "ayw" and "ayr". Thus, to determine if a patient is infected with a particular subtype of hepatitis B virus, at least one probe set should include at least one first probe, such as a monospecific polyclonal antibody, e.g., an anti-peptide antibody, that binds to one common epitope on HBsAg, and at least four second probes, such as four different mouse monoclonal antibody species that each specifically binds to one of the four HBsAg subtypes, i.e., anti-adw, anti-adr, anti-ayw, and anti-ayr, but don't cross-react with the other subtypes or compete with the other probes.

In this example, the first probe comprises a rabbit polyclonal anti-HBsAg antibody comprising at least one biotin moiety ("b-1P"). The corresponding second probes comprise four different subtype-specific monoclonal antibodies, each specifically binding a different HBsAg subtype ("2Pdw", "2Pdr", "2Pyw", and "2Pyr", respectively) without affecting the binding of b-1P, and vice versa. Each second probe further comprises an identity portion including a coded molecular tag with an internal hybridization tag at the proximal end of the coded molecular tag (relative to the antibody molecule) and a cleavable linker group located between the antibody molecule and the proximal end of the coded molecular tag.

A sample comprising HBsAg of the adr subtype ("HB-adr") is combined with this illustrative probe set and incubated, allowing at least one molecular complex, comprising b-1P:HB-adr:2Pdr, to form. CaptAvidin agarose gel (Molecular Probes Cat. # C-21386) is added to make a slurry and the biotinylated components, including the molecular complexes bind. The slurry is centrifuged in an Eppendorf bench top centrifuge to pellet the agarose. The supernatant is discarded and the pellet is washed with phosphate-buffered saline, pH 7.0 ("PBS" in this example). The resulting pellet is re-suspended in an appropriate reagent to release the cleavable components comprising coded molecular tags, centrifuged, the supernatant comprising the cleavable components is collected and diluted in PBS or neutralized, depending on the cleavage reagent. The supernatant is combined with a substrate comprising at least one hybridization tag complement. The cleavable components become indirectly tethered to the substrate when the hybridization tag of the coded molecular tag (capture ligand) hybridizes with its hybridization tag complement (capture moiety) on the substrate. A fluid flow is placed across the surface of the substrate, stretching the coded molecular tag in the direction of flow from its tether. The substrate is illuminated with light of appropriate excitation wavelengths and the coded molecular tags are individually detected by laser confocal microscopy. The order of fluorescent reporter groups is identified, allowing the presence of HBsAg of the adr subtype in the sample to be determined.

EXAMPLE 9

Drug and Metabolite Detection

Figure 9:
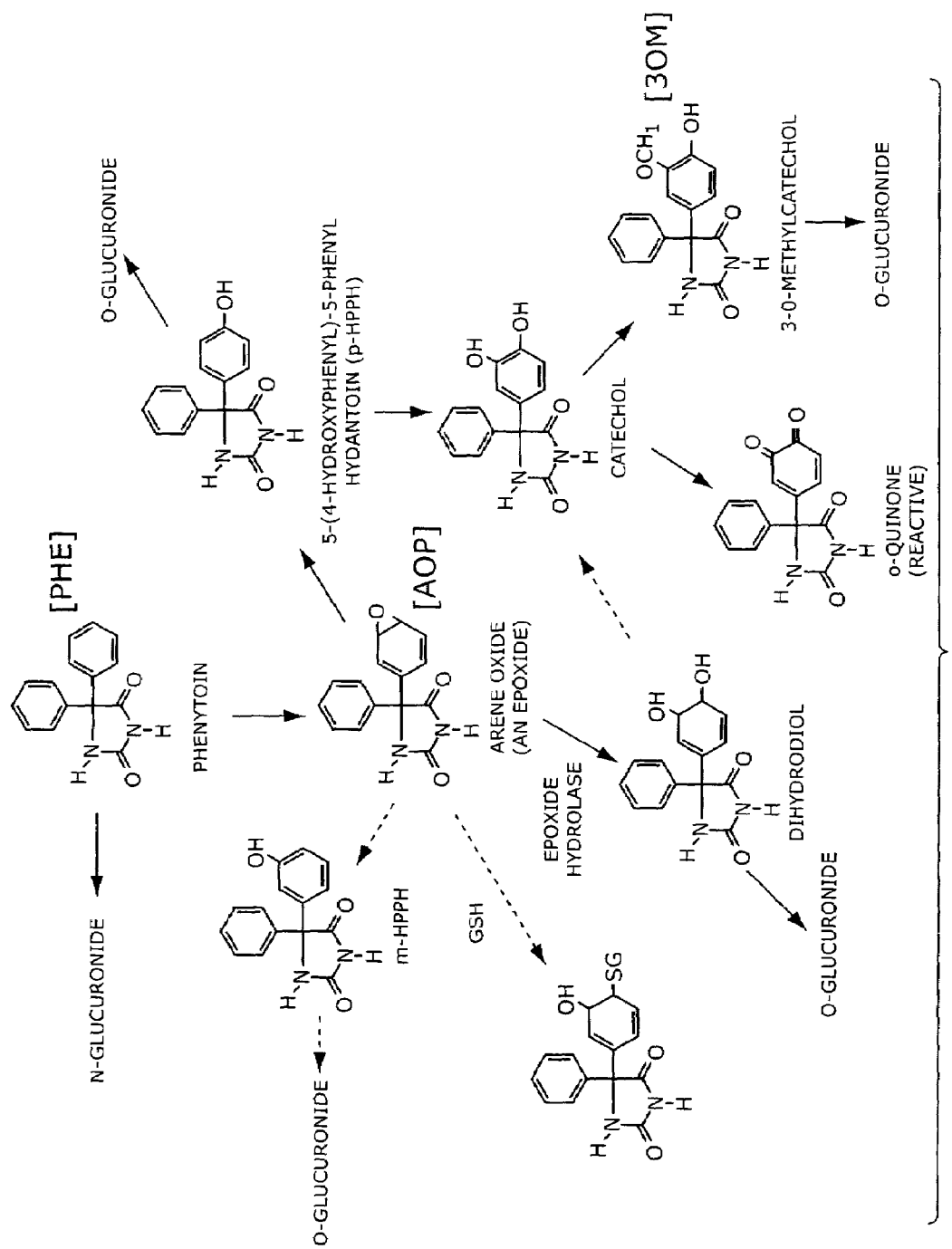
FIG. 9: depicts part of the metabolic pathway for the drug phenyloin in humans. As described in Example 9, the serum levels of the analytes phenyloin, one of its active metabolites, the arene oxide of phenyloin, and a possibly toxic metabolite, 3-O-methylcatechol (shown as [PHE], [AOP], and [3OM] in FIG. 9) can be measured using the present teachings.

In this exemplary embodiment, the analytes phenyloin, an anti-convulsant drug ("PHE" in this example); the arene oxide of phenyloin, an active intermediate ("AOP" in this example); and 3-O-methylcatechol, a possible toxic metabolite ("3OM" in this example); shown in FIG. 9, are identified using antibodies and aptamers.

The nucleotide sequences of several custom nucleic acid aptamers, each reactive with PHE, AOP, and 3OM, are obtained from a commercial source (e.g., RiNA GmbH, Berlin, Germany; SomaLogic, Boulder, Colo.). Alternatively, aptamers can be obtained, without undue experimentation, using the SELEX and anti-SELEX processes known in the art. Biotinylated aptamers are prepared using conventional solid-phase synthesis using an Applied Biosystems 3400 DNA Synthesizer, appropriate nucleotide phosphoramidites, and biotin phosphoramidite (Glen Research Cat. No. 10-1953-95) so that the aptamers are biotin labeled on their 3'-ends. The biotinylated aptamers are tested in a conventional binding assay to verify that they still bind to PHE, AOP, and 3OM after biotinylation. One reactive biotinylated aptamer is selected for use as a probe ("b-Apt" in this example).

Several monoclonal antibodies, each reactive with one of PHE, AOP, or 3OM, but not cross-reactive with either of the other two compounds, are generated by and purchased from a custom antibody supplier (e.g., Genemed Synthesis, Inc. So. San Francisco, Calif.; Biogenesis, Ltd., Poole, UK; Fusion Antibodies, Ltd., Belfast, Northern Ireland). The monoclonal antibodies are activated with the cleavable heterobifunctional crosslinker N-Succinimdyl 3-(2-pyridyidithio)propionate (SPDP; Pierce Biotechnology Cat. No. 21857), as described in Bioconjugate Techniques, particularly at page 232, protocol steps 1–5.

The 5' phosphate groups of three coded molecular tag species, each comprising a DNP capture ligand near the 3' end (Coded molecular tag 1, Coded molecular tag 2, and Coded molecular tag 3 in this example), are separately cystamine-modified using the crosslinker 1-Ethyl-3-[3-dimethylaminopropyl]carbodiimide hydrochloride (EDC; Pierce Biotechnology Cat. No. 77149), as described in Bioconjugate Techniques, particularly at pages 651–52. The cystamine-modified coded molecular tags are combined with the activated monoclonal antibodies as follows: Coded molecular tag 1 with each of the PHE monoclonal antibodies; Coded molecular tag 2 with each of the AOP monoclonal antibodies; and Coded molecular tag 3 with each of the 3OM monoclonal antibodies; and conjugated essentially as described in Bioconjugate Techniques, particularly at pages 663–64 and FIG. 407 (except that activated antibody molecules are substituted for activated alkaline phosphatase in the protocol) to assemble probes. Aliquots of the resulting coded molecular tag-monoclonal antibody probes are tested to verify that they retain immunoreactivity and appropriately reactive probes are selected ("Coded molecular tag 1-PHE", "Coded molecular tag 2-AOP", and "Coded molecular tag 3-3OM", respectively).

A whole blood sample is collected from a patient with epilepsy being medicated with Dilantin™ (phenyloin) and serum obtained using conventional methods. The serum is placed in a Centrifree® micropartition device (Cat. No. 4104, Millipore Corp., Bedford, Mass.) and processed, essentially as described in the manufacturer's instructions, to obtain an ultrafiltrate ("Ultrafiltrate" in this example).

Probe sets comprising b-Apt and Coded molecular tag 1-PHE; b-Apt and Coded molecular tag 2-AOP; and b-Apt Coded molecular tag 3-3OM; are combined with the Ultrafiltrate under conditions appropriate for molecular complex formation to occur. The reaction mixture comprising the molecular complexes is placed on a streptavidin-coated microscope slide (Greiner Bio-One) and incubated at room temperature for thirty minutes. The unbound material is removed and the slide is washed with PBS. The coded molecular tags are cleaved from the coded molecular tag-monoclonal antibody conjugates using dithiothreitol (DTT; Pierce Biotechnology Cat. No. 20290), as described in Bioconjugate Techniques, particularly at pages 79–80, and the cleavable components comprising the coded molecular tags are isolated. The isolated cleavable components are combined with a substrate comprising anti-DNP antibody capture moieties and the cleavable components become indirectly tethered to the substrate. The tethered cleavable components are individually detected using an appropriate single molecule detection technique and the order of reporter groups are identified and quantified. The quantity of each coded molecular tag species allows the concentration of each of the three analytes, i.e., PHE, AOP, and 3OM, to be determined.

EXAMPLE 10

Confocal Detection System

At least one molecular complex or at least part of a molecular complex, comprising a coded molecular tag in a low fluorescence buffer or solvent, such as phosphate buffered saline, pH 8.0, Tris-EDTA buffer (TE), pH 8.0, or distilled de-ionized water is placed on a substrate, in this example, a treated 1"×3" quartz microscope slide (Technical Glass Products, Inc., Painesville Twp., Ohio). At least one molecular complex or at least part of a molecular complex comprises a coded molecular tag comprising λ DNA comprising the fluorescent reporter group species FAM™ (488ex/520em), NED™ (488ex/570em) and Liz™ (488ex/660em). A treated 1"×1" quartz cover slip (Technical Glass Products, Inc.) coated with (3-aminopropyl)triethoxysilane (APTES) is placed over the slide so that the buffer comprising molecular complexes is between the slide and the APTES-coated cover slip and the molecular complexes indirectly attached to the slide. To further stretch or elongate the bound molecular complexes, the substrate can be placed in a directional flow or field, for example but not limited to a solution or agarose fluid flow, an electric or dielectric field, or the like, so that at least one molecular complex is stretched in the direction of flow or in the field (see, e.g., T. Perkins et al., Science 268:83–7 (1995); S. Matsuura et al., Nucl. Acids Res. 29(16):e79 (2001); D. Schwarz, U.S. Pat. No. 6,294,136; and V. Namasivayam et al., Anal. Chem. 74:3378–85 (2002)).

Prior to use, the quartz slides and cover slips can be treated by soaking in ethanol for 30 minutes with sonication, then water for 30 minutes with sonication, then ethanol for an additional 30 minutes with sonication. Following the second ethanol/sonication step, the treated slides and cover slips are ready for use or can be stored in distilled deionized water.

Figure 10:
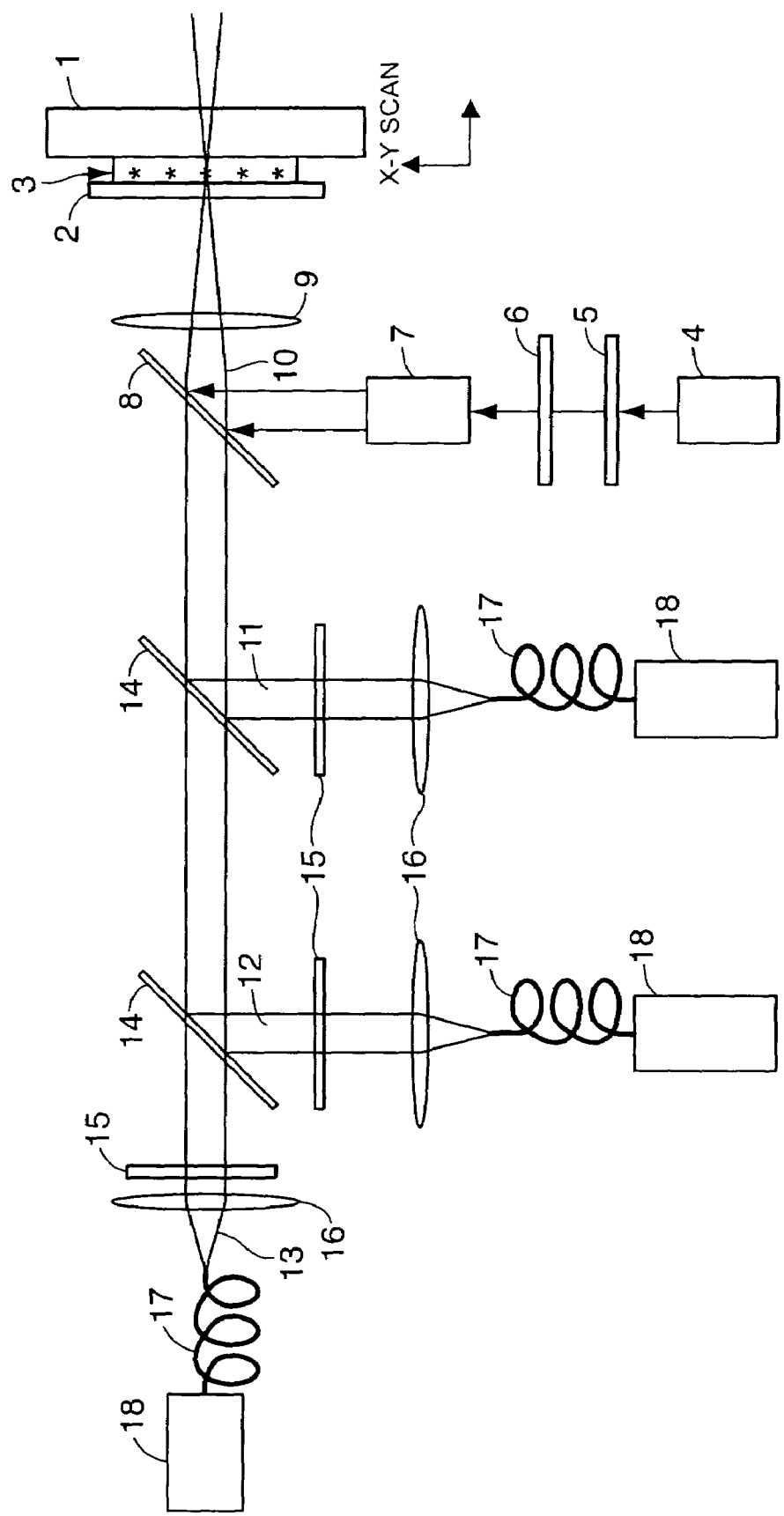
FIG. 10: schematically depicts an exemplary laser-confocal microscopy detection apparatus for individually detecting at least one molecular complex, at least one part of a molecular complex, or both, and identifying the order of fluorescent reporter group species in at least one identity portion, as described in Example 10.

As shown in FIG. 10, the slide (1) and cover slip (2) placed in a standard microscope slide holder mounted on a X-Y Piezo Flexure stage (P-517.2CL, Polytec PI, Germany). The stage is used for scanning the substrate and individually detecting the molecular complexes comprising fluorescence reporter groups (3). The slide (1) is placed in the holder with the cover slip (2) facing the illumination source. A multi-line argon-ion laser (4) beam (488 nm, 514 nm) is passed through a 488NB3/XLK06 laser line filter (5; Omega Optical Inc., Brattleboro, Vt.) to select the 488 nm line only, a neutral density filter to control the laser intensity (6; Omega Optical Inc., Brattleboro, Vt.), and a 15× Galilean beam expander (7; Edmund Scientific, Barrington, N.J.), then reflected towards the sample by an XF2037 (500DRLP)(Omega Optical Inc., Brattleboro, Vt.) or a 500DCLP (Chroma Technology Corp., Rockingham, Vt.) dichroic longpass beam splitter (8). The beam is focused onto at least one molecular complex (3) using a 40×/1.15NA (numerical aperture) water immersion objective lens (9; UAPO40XW3/340, Olympus Inc., Tokyo, Japan). The emitted fluorescence from the laser-illuminated molecular complexes on the substrate is collected by the objective lens (9), generating a collimated beam (10). The collimated beam (10) passes through the main dichroic longpass beam splitter (8), and is spectrally separated into three spectral channels (11, 12, 13) using two secondary dichroic filters (14; 540DRLP and 590DRLP, Omega Optical Inc., Brattleboro, Vt.). In each of the three spectral channels, a bandpass filter (15) is used to set the spectral range and further reduce the amount of laser light reaching the single photon counting detector (16). In this example, bandpass filters 520DF22, 570DF26, and 660DF14 (15; Omega Optical Inc., Brattleboro, Vt.) are used to produce spectral bands of 520 nm FWHM 22 nm, 570 nm FWHM 26 nm, and 660 nm FWHM 14 nm, respectively.

The collimated beam in each channel is then focused by a 01LAO119 Achromat 90 mm focal length tube lens (16; Melles Griot, Carlsbad, Calif.) onto a confocal pinhole comprising a SPCM-QC4 62.5 μm/0.27 NA core diameter fiber (17; PerkinElmer Optoelectronics, Canada). The light exiting the fiber in each channel is collected by a separate SPCM-AQR-14-FC single photon counting detector (18; PerkinElmer Optoelectronics, Canada). Alternatively, instead of using a separate detector for each spectral channel, an electron multiplying CCD camera mounted on a spectrograph can be used, for example but not limited to, a Sensovation SamBa SE-34 camera (Ludwigshafen, Germany), mounted on a Jobin-Yvon CP140-3301 spectrograph (Instruments SA, Inc. Edison N.J.). The detection system is controlled by and data collection performed using software based on LabVIEW software (National Instruments, Austin, Tex.). A TTL (transistor-transistor logic) finite pulse train at a user selectable rate and duty cycle triggers analog output of voltages to the X and Y axes of the stage which in turn sets the scanning of the molecular complexes. A second TTL pulse train synchronized to the first (also at a user selectable rate and duty cycle) triggers analog input of the actual X and Y location and gates the single photon detectors to integrate the photon count. The integrated photon signal from each of the three detectors is plotted against the actual X and Y locations for visualization. The signal from each of the detectors is used for determining the presence and identity of the fluorescent reporter groups. The order of fluorescent reporter group species in each individually detected molecular complex is identified and the presence of the corresponding analyte is determined.

The skilled artisan will appreciate that, while the confocal detection system described herein is appropriate for certain SMD techniques, a large number of detection systems can be used, as appropriate. Detailed descriptions of exemplary SMD detection devices can be found in, among other places, K. Weston et al., Anal. Chem. 74:5342–5349 (2002); H. Li et al., Anal. Chem. 75:1664–70 (2003); I. Braslavsky et al., Proc. Natl. Acad. Sci. 100:3960–64 (2003); N. Dovichi et al., Anal. Chem. 56:348–54 (1984); M. Medina et al., BioEssays 24:758–64 (2002); J. Kim et al., Anal. Chem. 73:5984–91 (2001); P. Tinnefeld et al., J. Phys. Chem. 105:1989–8003 (2001); Z. Foldes-Papp et al., Proc. Natl. Acad. Sci. 98:11509–14 (2001); Y. Ma et al., Electrophoresis 22:421–26 (2001); K. Swinney and D. Bornhop, Electrophoresis 21:1239–50 (2000); C. Seidel et al., U.S. Pat. No. 6,137,584; and D. Schwarz, U.S. Pat. No. 6,294,136.

EXAMPLE 11

Electrochemiluminescence Detection

Several probe species comprising reaction portions and cleavable components including at least one capture ligand and a coded molecular tag comprising $Ru(bpy)_3^{2+}$, $Os(phen)_2(dppene)^{2+}$, and/or $Al(HQS)_3^{3+}$ are synthesized. The illustrative coded molecular tags comprise three labeling positions, each occupied by. Probe sets are prepared comprising one electrochemiluminescent reporter group-labeled first probe and a corresponding second probe comprising an analytical portion including a mobility modifier (see, e.g., U.S. patent application Ser. No. 09/522,640). When these probe sets are combined with corresponding analytes, molecular complexes form.

Figure 11:
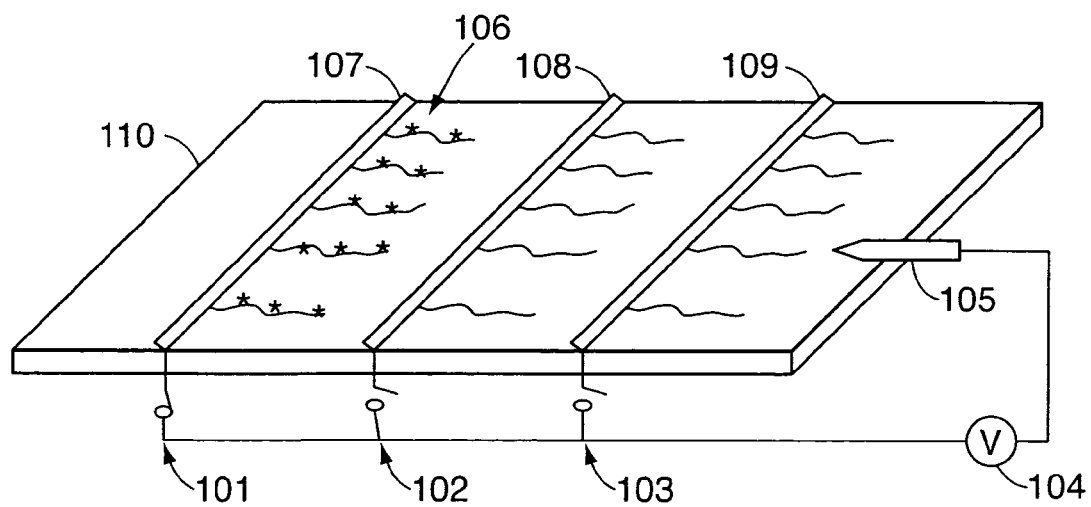
FIG. 11: schematically depicts a substrate comprising an illustrative electrogenerated chemiluminescence excitation apparatus for individually detecting at least one bound molecular complex or at least part of a molecular complex comprising at least one electrochemiluminescent reporter group, as described in Example 11.

The molecular complexes are separated using electrophoresis and isolated. The isolated molecular complexes are combined with an appropriate reagent to release the cleavable components, which are isolated. As shown in FIG. 11, the isolated cleavable components are combined with a substrate comprising a conductive surface (110) with a patterned surface comprising appropriate capture moieties and matched electrodes (107–109), and a Ag/AgCl reference electrode (105). The various electrodes can be selectively connected (101–103) to a power source (104), such as a potentiometer, as shown. The cleavable components are tethered to the surface of the substrate via capture ligand-capture moiety interactions. A fluid flow, comprising 0.05 M tripropylamine (TPA) in 0.1 M $KH_2PO_4$ is directed across the surface of the substrate, perpendicular to the electrode array, to elongate the bound cleavable components, as shown in FIG. 11 (fluid flow left to right). Typically, the pH of the solution is maintained between 6 and 12.

A potential of 1.1 V (vs. the Ag/AgCl reference electrode) is sequentially applied to the electrodes on the substrate, oxidizing the electrochemiluminescent labels together with the co-reactant TPA and initiating electrochemiluminescence. As each electrode is activated, a multi-channel SMD optical detection system comprising spectral channels for 620 nm, 584 nm, and 500 nm, is focused on a very small area of the electrode surface so that on average only one cleavable component is in the field of view (as shown in FIG. 11, switch 101 is closed, activating electrode 107, initiating ECL in the electrochemiluminescent reporter group species in the cleavable components 106 tethered adjacent to electrode 107). The order of the electrochemiluminescent reporter group species in each individually detected cleavable component is identified and the presence of the corresponding analyte is determined.

The skilled artisan understands that a variety of electrochemiluminescent reporter groups can be employed in the disclosed compositions, methods, and kits and individually detected as described. The skilled artisan also understands that other electrochemical generation techniques and detection apparati can be employed to individually detect electrochemiluminescent reporter groups in at least one molecular complex, at least part of a molecular complex, or both.

EXAMPLE 12

Tethering and Attaching Coded Molecular Tags

Full-length λ-DNA comprising a multiplicity of reporter group species in an ordered pattern is end-labeled with biotin using conventional methods ("b-λ" in this example). The b-λ is suspended in distilled de-ionized water at a final concentration of 0.01 to 0.1 µg/mL. A streptavidin coated glass slide (Greiner Bio-One) is soaked in phosphate-buffered saline, pH 7.2 ("PBS" in this example), then blocked using a 1% solution (weight/volume) of bovine serum albumin (BSA) in PBS. The blocked slide is washed three times with PBS, then a hybridization chamber is attached to the slide. The b-λ solution is introduced into the hybridization chamber and incubated for two hours at 4° C., allowing the b-λ barcodes to become tethered to the streptavidin-coated slide. After the incubation, the slide is washed three times with PBS and is ready for individual detection. The slide is then analyzed, using an appropriate SMD technique, to allow the attached λ-DNA molecules to be individually detected and the order of reporter group species in the corresponding coded molecular tags to be identified.

Alternatively, a glass cover slip (VWR Scientific Products) is silanated as follows. The glass slide is incubated in Piranha solution (70:30 concentrated $H_2SO_4$ to $H_2O_2$) for 12 hours at room temperature. The cover slip is rinsed with deionized water, then incubated in a solution of 3% APTES in 95% ethanol for 1 hour. The cover slip is dipped in absolute ethanol and cured for one hour at 115° C. Next, the silanated cover slip is cooled to room temperature, then washed with 95% ethanol.

A drop of water comprising full-length λ DNA comprising a coded molecular tag at a concentration of approximately 0.01–0.1 µg/mL is placed on the silanated glass cover slip. An untreated glass slide is floated on top, forcing the drop to spread to a thickness of a few microns. The λ-DNA molecules comprising the coded molecular tags attach to the silanated cover slip and, as the air-water interface recedes due to capillary action and evaporation, the λ-DNA molecules stretch and become elongated. The silanated cover slip is then analyzed, using an appropriate SMD technique, to allow the attached λ-DNA molecules to be individually detected and the order of reporter group species in the corresponding coded molecular tags to be identified.

In yet another alternate method, λ-DNA comprising a coded molecular tag is suspended in a polymer solution (1–4% polyacrylamide in deionized water) at a concentration of 0.01–0.1 µg/mL. A glass cover slip is placed in the holder and spun at 10,000–15,000 RPM. Alternately, a spin coating machine can be used. A small volume (0.5 µL) of the λ-DNA polymer solution is dropped onto the spinning cover slip and the solution flows very rapidly towards the edges of the cover slip due to centrifugal force. During this rapid radial flow, the λ-DNA in the polymer solution experiences high shear force and stretch, elongating the DNA molecule. The flowing polymer solution dries very rapidly, effectively attaching the elongated λ-DNA molecules to the cover slip. The attached λ-DNA molecules are individually detected and the order of reporter group species in the corresponding coded molecular tags identified using an appropriate SMD technique.

Detailed descriptions of additional molecular elongation methods can be found in, among other places, Yokota et al., Anal. Chem. 71:4418–22 (1999); Bensimon et al., Science 265:2096–98 (1994); Smith et al., Science 258:1122–26 (1992); and Perkins et al., Science 268:83–87 (1995).

Although the invention has been described with reference to various applications, methods, and compositions, it will be appreciated that various changes and modifications can be made without departing from the invention. The foregoing examples are provided to better illustrate the disclosed compositions, methods, and kits and are not intended to limit the scope of the teachings herein.

---

We claim:

1. A method for determining the presence of at least one analyte in a sample, comprising:
   forming at least one molecular complex comprising (a) the at least one analyte and (b) at least one first probe comprising at least one reaction portion and at least one identity portion comprising at least one coded molecular tag; and
   individually detecting the at least one molecular complex or at least part of the at least one molecular complex to determine the presence of the at least one analyte in the sample.

2. The method of claim 1, wherein the molecular complex further comprises at least one second probe comprising at least one reaction portion and at least one analytical portion.

3. The method of claim 1, wherein the at least one identity portion comprises a multiplicity of fluorescent reporter groups.

4. The method of claim 3, wherein the at least one identity portion comprises at least one peptide nucleic acid (PNA), at least one pseudocomplementary peptide nucleic acid (pcPNA), or combinations thereof.

5. The method of claim 1, wherein the at least one identity portion comprises at least one affinity tag, at least one mobility modifier, or at least one affinity tag and at least one mobility modifier.

6. The method of claim 1, wherein the at least one identity portion is within, coextensive with, or overlaps at least part of the reaction portion.

7. The method of claim 2, wherein the at least one analytical portion is within, coextensive with, or overlaps at least part of the reaction portion.

8. The method of claim 2, wherein the at least one analytical portion comprises at least one PNA, at least one pcPNA, at least one dendrimer, at least one reporter group, or combinations thereof.

9. The method of claim 2, wherein the at least one analytical portion comprises at least one fluorophore, at least one mobility modifier, at least affinity tag, or combinations thereof.

10. The method of claim 2, wherein at least part of the reaction portion of the at least one first probe and at least part of the reaction portion of the at least one second probe hybridize to complementary sequences on the same strand of the at least one analyte.

11. The method of claim 10, wherein the at least part of the reaction portion of the at least one first probe and the at least part of the reaction portion of the at least one second probe hybridize adjacent to one another.

12. The method of claim 11, further comprising at least one ligation agent.

13. The method of claim 12, wherein the at least one ligation agent comprises at least one DNA ligase, at least one RNA ligase, or combinations thereof.

14. The method of claim 13, wherein the at least one DNA ligase, the at least one RNA ligase, or both the at least one DNA ligase and the at least one RNA ligase comprises at least one thermostable ligase.

15. The method of claim 2, wherein the at least one analyte comprises at least one nucleic acid sequence comprising at least one ribonucleotide, at least one deoxyribonucleotide, or at least one ribonucleotide and at least one deoxyribonucleotide.

16. The method of claim 15, wherein the at least one analyte comprises at least one nucleic acid sequence comprising at least one heritable mutation, at least one somatic mutation, at least one single nucleotide polymorphism (SNP), at least one point mutation, at least one deletion mutation, at least one insertion mutation, at least one chromosomal translocation, or combinations thereof.

17. The method of claim 1, wherein the at least one analyte comprises at least one diagnostic indicator, at least one foreign antigen, at least one drug, at least one metabolite, at least one small molecule, at least one peptide, at least one nucleotide, at least one glycosidic bond, or combinations thereof.

18. The method of claim 2, wherein the at least one analyte comprises at least one diagnostic indicator, at least one foreign antigen, at least one drug, at least one metabolite, at least one small molecule, at least one peptide, at least one nucleotide, at least one glycosidic bond, or combinations thereof.

19. The method of claim 1, wherein the individually detecting comprises at least one scanning probe microscopy technique, at least one applied optical spectroscopy technique, or both at least one scanning probe microscopy technique and at least one applied optical spectroscopy technique.

20. The method of claim 2, wherein the individually detecting comprises at least one scanning probe microscopy technique, at least one applied optical spectroscopy technique, or both at least one scanning probe microscopy technique and at least one applied optical spectroscopy technique.

21. The method of claim 20, wherein the at least one scanning probe microscopy technique comprises atomic force microscopy (AFM), magnetic resonance force microscopy (MRFM), scanning electrochemical microscopy (SECM), scanning tunneling microscopy, or combinations thereof.

22. The method of claim 20, wherein at least one applied optical spectroscopy technique comprises fluorescence correlation spectroscopy (FCS), evanescent wave induced fluorescence spectroscopy (EWIFS), scanning near-field optical microscopy (SNOM), surface enhanced raman spectroscopy (SERS), surface enhanced resonant raman spectroscopy (SERRS), surface plasmon resonance (SPR), laser-confocal microscopy, or combinations thereof.

23. The method of claim 20, wherein the individually detecting comprises attaching at least one molecular complex or at least part of a molecular complex, tethering at least one molecular complex or at least part of a molecular complex, or both attaching and tethering at least one molecular complex or at least part of a molecular complex directly or indirectly to a substrate.

24. The method of claim 23, wherein the substrate comprises at least one capture moiety.

25. The method of claim 24, wherein the attaching, the tethering, or both the attaching and the tethering comprises at least one first capture moiety and at least one second capture moiety, wherein the at least one first capture moiety and the at least one second capture moiety are spatially separated from each other on the substrate.

26. The method of claim 3, wherein individually detecting comprises attaching at least one molecular complex or at least part of a molecular complex, tethering at least one molecular complex or at least part of a molecular complex, or both attaching and tethering at least one molecular complex or at least part of a molecular complex to a substrate and identifying the order of the fluorescent reporter groups using laser-confocal microscopy; and wherein the analyte comprises at least one nucleic acid sequence comprising at least one ribonucleotide, at least one deoxyribonucleotide, or at least one ribonucleotide and at least one deoxyribonucleotide; at least one heritable mutation, at least one somatic mutation, at least one diagnostic indicator, at least one foreign antigen, at least one drug, at least one metabolite, at least one small molecule, or combinations thereof.

27. The method of claim 3, wherein individually detecting comprises identifying the order of reporter group species in a molecular complex or at least part of a molecular complex in solution using laser-confocal microscopy; and wherein the analyte comprises at least one nucleic acid sequence comprising at least one ribonucleotide, at least one deoxyribonucleotide, or at least one ribonucleotide and at least one deoxyribonucleotide; at least one heritable mutation, at least one somatic mutation, at least one diagnostic indicator, at least one foreign antigen, at least one drug, at least one metabolite, at least one small molecule, or combinations thereof.

28. The method of claim 2, further comprising amplifying the molecular complex.

* * * * *